(12) United States Patent
Kim

(10) Patent No.: US 9,557,318 B2
(45) Date of Patent: Jan. 31, 2017

(54) ARRAY PLATES FOR WASHING SAMPLES

(71) Applicant: Curiox Biosystems Pte Ltd., Singapore (SG)

(72) Inventor: Namyong Kim, Palo Alto, CA (US)

(73) Assignee: Curiox Biosystems Pte Ltd., Singapore (SG)

( * ) Notice: Subject to any disclaimer, the term of this patent is extended or adjusted under 35 U.S.C. 154(b) by 0 days.

(21) Appl. No.: 14/326,780

(22) Filed: Jul. 9, 2014

(65) Prior Publication Data

US 2015/0018248 A1 Jan. 15, 2015

Related U.S. Application Data

(60) Provisional application No. 61/844,046, filed on Jul. 9, 2013, provisional application No. 61/968,249, filed on Mar. 20, 2014.

(51) Int. Cl.
*B01L 3/00* (2006.01)
*G01N 33/50* (2006.01)
(Continued)

(52) U.S. Cl.
CPC ......... *G01N 33/5005* (2013.01); *B01L 3/0248* (2013.01); *B01L 3/5085* (2013.01); *B01L 3/5088* (2013.01); *B29C 45/1671* (2013.01); *B01L 3/502792* (2013.01); *B01L 2200/026* (2013.01); *B01L 2200/0642* (2013.01); *B01L 2200/12* (2013.01); *B01L 2300/089* (2013.01);
(Continued)

(58) Field of Classification Search
CPC .............. B01L 3/5088; B01L 3/502792; B01L 2200/0642; B01L 2300/0829; B01L 2300/089; B01L 3/5085; B29K 2995/0092; B29K 2995/0093
See application file for complete search history.

(56) References Cited

U.S. PATENT DOCUMENTS 3,426,108 A 2/1969 Britten
3,754,872 A 8/1973 Zauft
(Continued)

FOREIGN PATENT DOCUMENTS

CN 1460723 A 12/2003
CN 1858593 A 11/2006
(Continued)

OTHER PUBLICATIONS

Curiox Biosystems PTE Ltd., International Search Report and Written Opinion, PCT/US2015/019760, Jun. 2, 2015, 12 pgs.
(Continued)

*Primary Examiner* — Brian R Gordon
(74) *Attorney, Agent, or Firm* — Morgan, Lewis & Bockius LLP

(57) ABSTRACT

Methods and systems for processing a first solution on a respective primary area of a device with a plurality of primary areas and a plurality of secondary areas are described. A method includes providing the device and dispensing a second solution to a respective secondary area of one or more secondary areas adjacent to the respective primary area, thereby mixing the first solution on the respective secondary area and the second solution on the respective primary area. The method also includes removing at least a portion of the mixed solution.

14 Claims, 59 Drawing Sheets

(51) Int. Cl.
*B01L 3/02* (2006.01)
*B29C 45/16* (2006.01)
*B29C 45/14* (2006.01)
*B29C 45/26* (2006.01)

(52) U.S. Cl.
CPC .................. *B01L 2300/0822* (2013.01); *B01L 2300/0829* (2013.01); *B01L 2400/0406* (2013.01); *B29C 45/14065* (2013.01); *B29C 45/14336* (2013.01); *B29C 45/14778* (2013.01); *B29C 45/2628* (2013.01); *B29C 2045/14122* (2013.01); *B29K 2995/0092* (2013.01); *B29K 2995/0093* (2013.01)

(56) References Cited

U.S. PATENT DOCUMENTS

| | | | |
|---|---|---|---|
| 5,041,266 A * | 8/1991 | Fox | B01L 3/50853 422/552 |
| 5,219,528 A | 6/1993 | Clark | |
| 5,229,163 A * | 7/1993 | Fox | B01L 3/50853 204/169 |
| 5,506,121 A | 4/1996 | Skerra et al. | |
| 5,560,811 A | 10/1996 | Briggs et al. | |
| 5,691,147 A * | 11/1997 | Draetta | C12N 9/1205 435/4 |
| RE35,894 E | 9/1998 | Ellison et al. | |
| 5,817,510 A | 10/1998 | Pandey et al. | |
| 6,048,908 A | 4/2000 | Kitagawa | |
| 6,086,825 A | 7/2000 | Sundberg et al. | |
| 6,103,493 A | 8/2000 | Skerra et al. | |
| 6,130,098 A | 10/2000 | Handique et al. | |
| 6,238,626 B1 | 5/2001 | Higuchi et al. | |
| 6,331,441 B1 | 12/2001 | Balch et al. | |
| 6,534,014 B1 | 3/2003 | Mainquist et al. | |
| 6,565,813 B1 * | 5/2003 | Garyantes | B01F 13/0071 422/553 |
| 6,578,952 B1 | 6/2003 | Sugiyama et al. | |
| 6,664,044 B1 | 12/2003 | Sato | |
| 6,699,437 B1 | 3/2004 | Astle | |
| 6,716,629 B2 | 4/2004 | Hess et al. | |
| 6,767,733 B1 | 7/2004 | Green | |
| 6,902,705 B1 * | 6/2005 | Caillat | G01N 33/5438 422/500 |
| 7,163,823 B2 | 1/2007 | Patno et al. | |
| 7,344,877 B1 | 3/2008 | Camacho et al. | |
| 7,439,056 B2 | 10/2008 | Duffy et al. | |
| 7,666,362 B2 | 2/2010 | Shanler | |
| 7,794,799 B1 | 9/2010 | Kim et al. | |
| 7,854,343 B2 | 12/2010 | Ellson et al. | |
| 8,221,697 B2 | 7/2012 | Nichols et al. | |
| 8,337,778 B2 | 12/2012 | Stone et al. | |
| 8,987,174 B2 * | 3/2015 | Routenberg | C40B 50/06 506/16 |
| 2002/0016009 A1 | 2/2002 | Ogura | |
| 2002/0094533 A1 | 7/2002 | Hess et al. | |
| 2003/0032046 A1 | 2/2003 | Duffy et al. | |
| 2003/0083474 A1 | 5/2003 | Schmidt | |
| 2003/0113813 A1 | 6/2003 | Heidaran et al. | |
| 2003/0124599 A1 | 7/2003 | Chen et al. | |
| 2003/0209560 A1 | 11/2003 | Hui et al. | |
| 2004/0106156 A1 | 6/2004 | Perez et al. | |
| 2004/0106191 A1 | 6/2004 | Muser | |
| 2004/0136876 A1 | 7/2004 | Fouillet et al. | |
| 2004/0142460 A1 | 7/2004 | Cima et al. | |
| 2004/0208792 A1 | 10/2004 | Linton et al. | |
| 2004/0234966 A1 | 11/2004 | Bryning et al. | |
| 2005/0045539 A1 | 3/2005 | Yu et al. | |
| 2005/0079105 A1 * | 4/2005 | Hunter | B01F 13/0071 506/40 |
| 2005/0084423 A1 | 4/2005 | Zarowitz et al. | |
| 2005/0186579 A1 | 8/2005 | Dellinger et al. | |
| 2006/0013031 A1 | 1/2006 | Ravkin et al. | |
| 2006/0051249 A1 * | 3/2006 | Knebel | B01L 3/5085 422/553 |
| 2006/0078893 A1 | 4/2006 | Griffiths et al. | |
| 2006/0105453 A1 * | 5/2006 | Brenan | B01L 3/50857 435/325 |
| 2006/0142468 A1 | 6/2006 | Downing, Jr. et al. | |
| 2007/0003448 A1 | 1/2007 | Kanigan et al. | |
| 2007/0077651 A1 | 4/2007 | Guarino et al. | |
| 2007/0099208 A1 | 5/2007 | Drmanac et al. | |
| 2007/0117765 A1 | 5/2007 | Sauve et al. | |
| 2008/0003671 A1 | 1/2008 | Martin | |
| 2008/0173544 A1 | 7/2008 | Seul et al. | |
| 2009/0142564 A1 | 6/2009 | Plissonnier et al. | |
| 2009/0148348 A1 | 6/2009 | Pettigrew et al. | |
| 2010/0000304 A1 * | 1/2010 | Kim | B01L 3/5085 73/64.56 |
| 2010/0167950 A1 | 7/2010 | Juang et al. | |
| 2012/0220497 A1 * | 8/2012 | Jacobson | B01J 19/0046 506/16 |

FOREIGN PATENT DOCUMENTS

| | | |
|---|---|---|
| CN | 101031363 A | 9/2007 |
| DE | 10043042 C2 | 6/2002 |
| EP | 0812693 A1 | 12/1997 |
| EP | 1348533 B1 | 7/2002 |
| EP | 1358939 A2 | 4/2003 |
| EP | 1316360 B1 | 6/2003 |
| EP | 1386657 A1 | 7/2003 |
| EP | 1473079 A1 | 2/2004 |
| EP | 1399263 B1 | 3/2004 |
| EP | 1788047 A1 | 8/2005 |
| EP | 1683571 A1 | 1/2006 |
| GB | 1291610 | 10/1972 |
| GB | 2332273 A | 6/1999 |
| GB | 2334954 A | 9/1999 |
| JP | 3120453 B2 | 12/2000 |
| JP | 2002-502955 A | 1/2002 |
| JP | 2003-033177 A | 2/2003 |
| JP | 2004-020280 A | 1/2004 |
| JP | 2004-077476 A | 3/2004 |
| JP | 2004-535176 A | 11/2004 |
| JP | 2005-003803 A | 1/2005 |
| JP | 2005-099004 A | 4/2005 |
| WO | WO 96-23879 | 8/1996 |
| WO | WO 98/47003 | 10/1998 |
| WO | WO 98-55852 | 12/1998 |
| WO | WO 99/39829 A1 | 8/1999 |
| WO | WO 99/55826 | 11/1999 |
| WO | WO 00-14311 | 3/2000 |
| WO | WO 00-58735 | 10/2000 |
| WO | WO 01-04144 A2 | 1/2001 |
| WO | WO 03-029462 A1 | 4/2003 |
| WO | WO 2004-030820 A2 | 4/2004 |
| WO | WO 2004-111610 A2 | 12/2004 |
| WO | WO 2005/019254 A1 | 3/2005 |
| WO | WO 2005/019255 A1 | 3/2005 |
| WO | WO 2005/019256 A2 | 3/2005 |
| WO | WO 2006/004739 A2 | 1/2006 |
| WO | WO 2006/046699 A1 | 5/2006 |
| WO | WO 2007/102785 A1 | 9/2007 |
| WO | WO 2008/063136 A1 | 5/2008 |
| WO | WO 2010/120249 A1 | 10/2010 |
| WO | WO 2012/011877 A2 | 1/2012 |

OTHER PUBLICATIONS

Agency for Science, Technology and Research, Decision to Grant, JP2012-196318, Sep. 12, 2014, 3 pgs.
Curiox Biosystems Pte Ltd, International Preliminary Report on Patentablity, PCT/IB2013/000623, Aug. 5, 2014, 7 pgs.
Agency for Science, Technology and Research, Communication Pursuant to Article 94, EP07835548-4, Jul. 17, 2015, 3 pgs.
Kim, Office Action, U.S. Appl. No. 13/811,638, Sep. 11, 2015, 29 pgs.
Kim, Office Action, U.S. Appl. No. 14/338,168, Nov. 6, 2015, 8 pgs.
Cheng, Office Action, U.S. Appl. No. 14/050,321, Feb. 26, 2016, 31 pgs.

(56) References Cited

OTHER PUBLICATIONS

Erfle et al., "Reverse Transfections on Cell Arrays for High Content Screening Microscopy," Nature Protocols, Mar. 1, 2007, vol. 2 No. 2, 8 pgs.
Kim, Office Action, U.S. Appl. No. 14/452,172, Oct. 23, 2015, 16 pgs.
Lowe et al., "Perfluorochemicals: Their Applications and Benefits to Cell Culture," Tibtech, Jun. 1998, vol. 16, 6 pgs.
Takahashi et al., Induction of Pluripotent Stem Cells from Mouse Embryonic and Adult Fibroblast Cultures by Defined Factors, Cell, Aug. 25, 2006, 126, 14 pgs.
Vancha et al., "Use of Polyethyleneimine Polymer in Cell Culture as Attachment Factor and Lipofection Enhancer," BMC Biotechnology, Oct. 15, 2004, 12 pgs.
Agency for Science, Technology and Research, International Preliminary Report on Patentability, PCT/SG2007/000393, May 26, 2009, 4 pgs.
Agency for Science, Technology and Research, International Search Report and Written Opinion of the ISA, PCT/SG2007/000393, Feb. 20, 2008, 7 pgs.
Agency for Science, Technology and Research, Notification of First Office Action, CN 201110401674.9, Dec. 30, 2013, 9 pgs.
Agency for Science, Technology and Research, Notification of Reasons for Refusal, JP 2009-538373, Nov. 10, 2011, 7 pgs.
Agency for Science, Technology and Research, Notification of Reasons for Refusal, JP 2012-196318, Dec. 10, 2013, 3 pgs.
Agency for Science, Technology and Research, Notification of the First Office Action, CN 200780048922.8, Nov. 12, 2010, 4 pgs (available in Chinese only).
Agency for Science, Technology and Research, Notification of the Second Office Action, CN 200780048922.8, May 17, 2011, 4 pgs.
Agency for Science, Technology and Research, Notification on the Grant of Patent Right for Invention, CN 200780048922.8, Sep, 22, 2011, 1 pg.
Agency for Science, Technology and Research, Supplementary Search Report, EP 07835548.4, Jun. 30, 2010, 4 pgs.
Asberg, Surgace Energy Modified Chips for Detection of Conformational States and Enzymatic Activity in Biomolecules, Langmuir, 2006, pp. 2205-2211.
Beck, Improving Stamps for 10 nm Level Wafer Scale Nanoimprint Lithography, Microelectron. Eng., 2002, pp. 61-62 and 441.
Benor, Microstructuring by Microcontact Printing and Selective Surface Dewetting, J. of Vacuum Science & Technology B, 2007, pp. 1321-1326.
Beste, Small Antibody-like Proteins with Prescrived Ligand Specificities Derived from Lipocalin Fold, Proc. Natl. Acad. Sci, USA, 1999, pp. 1898-1903.
Biffinger, The Polar Hydrophobicity of Cluorinated Compounds, ChemBioChem, 2004, pp. 622-627.
Burbulis, Quantifying Small Numbers of Antibodies with a 'Near-Universal' Protein-DNA Chimera, Nature Methods, 2007.
Chiriac, Magnetic GMI Sensor for Detection of Biomolecules, J. Magnetism and Magnetic Materials, 2005, pp. 671-676.
Churaev, Wetting of Low-Energy Surgfaces, Advances in Colloid and Interface Science, 2007, pp. 134-135, 15-23.
Curiox Biosystems Pte Ltd, International Preliminary Report on Patentability, PCT/SG2010/000153, Oct. 18, 2011, 15 pgs.
Curiox Biosystems Pte Ltd, International Preliminary Report on Patentability, PCT/SG2011/000263, Dec. 21, 2012, 7 pgs.
Curiox Biosystems Pte Ltd, International Search Report and Written Opinion, PCT/IB2013/000623, Jul. 10, 2013, 7 pgs.
Curiox Biosystems Pte Ltd, International Search Report and Written Opinion, PCT/SG2010/000153, Sep. 17, 2010, 20 pgs.
Curiox Biosystems Pte Ltd, International Search Report and Written Opinion, PCT/SG2011/000263, Feb. 29, 2012, 20 pgs.
Daniel, Vibration-Actuated Drop Motion on Surfaces bor Batch Microfluidic Processes, Langmuir, 2005, pp. 4220-4228.
Decision to Grant, Application No. CN201110401674.9, Aug. 7, 2014, 2 pgs.
Dill, Modeling Water, The Hydrophobic Effect and Ion Solvation, Annu. Rev. Bidphys. Biomol. Struc, 2005, pp. 173-199.
Gao, A Commercially Available Perfectly Hydrophobic Material, Langmuir, 2007, pp. 9125-9127.
Gascoyne, Dielectrophoresis-based Programmable Fluidic Processors, Lab-on-a-Chip, 2004, pp. 299-309.
Genua, Functional Patterns Obtained by Nanoimprinting Lithography and Subsequent Growth of Polymer Brushes, Nanotechnology, 2007, 215301, 7 pgs.
Gill, Pharmaceutical Drug Discovery Using Novel Protein Scaffolds, Current Opinion in Biotechnology, 2006, 653-658.
Giovambattista, Effect of Surface Polarity on Water Contact Angle and Interfacial Hydration Structure, J. Phys. Chem., 2007, pp. 9581-9587.
Goddard, Polymer Surface Modification for the Attachment of Bioactive Compounds, Progress in Polymer Science, 2007, pp. 698-725.
Griffiths, Miniaturising the Laboratory in Emulsion Droplets, Trends in Biotechnology, 2006, pp. 395-402.
Herrmann, Enxymatically-Generated Fluorescent Detection in Micro-Channels with Internal Magnetic Mixing for the Development of Parallel Miicrofluidic ELISA, Lab-on-a-Chip, 2006, pp. 555-560.
Holt, Domain Antibodies: Proteins for Therapy, Trends Biotechnol, 2003, pp. 484-490.
Hutten, New Magnetic Nanoparticles for Biotechnology, J. Biotech., 2004, pp. 47-63.
Iliades, Triabodies: Single Chain Fv Fragments without a Linker Form Trivalent Trimers, FEBS Lett, 1997, pp. 437-441.
Jakobs, Micrometer Scale Gel Patterns, Colloids & Surfaces A: PhysioChem. Eng. Aspects, 2006, pp. 33-40.
Jung, Wetting Transition of Water Droplets on Superhydrophobic Patterned Surfaces, Scripta Materialia, 2007, pp. 1057-1060.
Kanta, Preparation of Silica-on-Titania Patterns with a Wettability Contrast, Langmuir, 2005, 5790-5794.
Kim, Final Office Action, U.S. Appl. No. 13/264,913, Jun. 21, 2013, 11 pgs.
Kim, Notice of Allowance, U.S. Appl. No. 12/282,162, May 14, 2012, 7 pgs.
Kim, Office Action, U.S. Appl. No. 12/282,162, Jun. 27, 2011, 8 pgs.
Kim, Office Action, U.S. Appl. No. 13/264,913, Nov. 7, 2012, 9 pgs.
Kim, Office Action, U.S. Appl. No. 13/264,913, Sep. 26, 2013, 10 pgs.
Kusumaatmaja, Controlling Drop Size and Polydispersity Using Chemically Patterned Surfaces, Langmuir, 2007, pp. 956-959.
Kwon, Quantitative Evaluation of the Relative Cell Permeability of Peptoids and Peptides, J. AM. Chem. Soc., 2007, pp. 1508-1509.
Leck, Final Office Action, U.S. Appl. No. 11/984,197, May 8, 2012, 10 pgs.
Leck, Office Action, U.S. Appl. No. 11/984,197, Mar. 14, 2013, 11 pgs.
Leck, Office Action, U.S. Appl. No. 11/984,197, May 26, 2011, 11 pgs.
Leck, Office Action, U.S. Appl. No. 11/984,197, Jul. 31, 2013, 12 pgs.
Li, What Do We Need for a Superhydrophobic surface? A review on the recent progress in the preparation of superhydrophobic surfaces, Chem. Soc. Rev, 2007, pp. 1350-1368.
Luca, Preparation of TIOx Thin Films by Reactive Pulsed-Laser Ablation, J. Optoelectronics and Adv. Materials, Apr. 2005, pp. 625-630.
Lundgren, Modeling of Wetting: A Study of Nanowetting at Rough and Heterogeneous Surfaces, Langmuir, 2007, pp. 1187-1194.
Ma, Superhydrophobic Surfaces, Current Opinion in Colloid & Interface Science, 2006, pp. 193-202.
Mardare, Microelectrochemical Lithography: A method for Direct Writing of Surface Oxides, Electrochimica Acta, 2007, pp. 7865-7869.
Matsuda, Phosphorylcholine-Endcapped Oligomer and Block Co-Oligomer and Surface Biological Reactivity, Biomaterials, 2003, pp. 4517-4527.

(56) References Cited

OTHER PUBLICATIONS

Meyer, Recent Progress in Understanding Hydrophobic Interactions, Proc. Netl. Acad. Sci USA, 2006, pp. 15739-15746.
Mosavi, The Ankyrin Repeat as Molecular Architecture for Protein Recognition, Protein Science, 2004, pp. 1435-1448.
Opdahl, Polymer Surface Science, The Chemical Record, 2001, pp. 101-122.
Pollack, Electrowetting-based Actuation of Liquid Droplets for Microfluidic Applications, Appl. Phys. Lett., 2000, pp. 1725-1726.
Popp, Sortagging: A versatile Method for Protein Labeling, Nature Chemical Biology, 2007, pp. 707-708.
Rastogi, Development and Evaluation of Realistic Microbioassys in Freely Suspended Droplets on a Chip, Biomicrofludics, 2007, 014107-1-014107-17.
Roach, Controllling Nonspecific Protein Adsorption in a Plug-Based Microfluidic System by Controlling Interfacial Chemistry Using Fluorous-Phase Surfactants, Analytical Chemistry, vol. 77, No. 3, Feb. 1, 2005, pp. 785-796.
Ronaghi, Pyrosequestering Sheds Light on DNA Sequestering, Genome Research, 2001, pp. 3-11.
Rose, Microdispensing Technologies in Drug Discovery, Drug Discovery Today, 1999, pp. 411-419.
Satriano, Bacterial Adhesion Onto Nanopatterned Polymer Surfaces, Materials Science & Engineering C, 2006, pp. 942-946.
Silverman, Multivalent Avimer Proteins Evolved by Exon Shuffling of a Family of Human Receptor Domains, Nature Biotechnology, 2005, pp. 1556-1561.
Skerra, Engineered Protein Scaffolds for Molecular Recognition, J. Mol. Recognit., 2000, pp. 167-187.
Song, Miniature Biochip System for Detection of Sscherichi coli O157:H7 Based on Antibody-Immobilized Capillary Reactors and Enzyme-linked Immunosorbent Assay, Analytica Chimica Acta, 2004, pp. 115-121.
Stephenson, Quantifying the Hydrophobic Effect: A Computer Simulation-Molecular-Thermodynamic Model for the Self-Assembly of Hydrophibic and Amphiphilic Solutes in Aqueous Solution, Jp. Phys. Chem. B, 2007, 1025-1044.
Stone, The Assembly of Single Domain Antibodies into Bispecific Decavalent Molecules, J. Immunological Methods, 2007, pp. 88-94.
Sundberg, Contact Angle Measurements by Confocal Microscopy for Non-Destructive Microscale Surface Characterization, J. Colloid and Interface Science, 2007, pp. 454-460.
Van Oss, Long-Rage and Short-Range Mechanisms of Hydrophobic Attraction and Hydrophilic Repulsion in Specific and Aspecific Interactions, J. Mol. Recognit., 2003, pp. 177-190.
Wang, Flow-Focusing Generation of Monodisperse Water Droplets Wrapped by Ionic Liquid on Microfluidic Chips: From Plug to Sphere, langmuir, 2007, pp. 11924-11931.
Wang, In-Situ Wilhelmy Balance Surface Energy Determination of Poly(3-hexylthiophere) and Poly(3,4-ethylenedioxythiophere) during Electrochemical Doping-Dedoping, Langmuir, 2006, pp. 9287-9294.
Washizu, Elecrostatic Actuation of Liquid Droplets for Microreactor Applications, IEEE Transactions on Industry Applications, vol. 34, No. 4, Jul.-Aug. 1998.
West, Microplasma Writing for Surface-Directed Millifludics, Lab-on-a-Chip, 2007, pp. 981-983.
Widom, The Hydrophobic Effect, Phys. Chem. Chem. Phys., 2003, pp. 3085-3093.
Wixforth, Flatland Fluidics, mstnews, 2002, pp. 42-43.
Curiox Biosystems Pte Ltd, International Search Report and Written Opinion, PCT/SG2006/000050, May 8, 2006, 6 pgs.
Perfulorodecalin-FluoroMed, downloaded on Sep. 5, 2013, from http://fluoromed.com/products/perfluorodecalin.html, 1 pg.

* cited by examiner

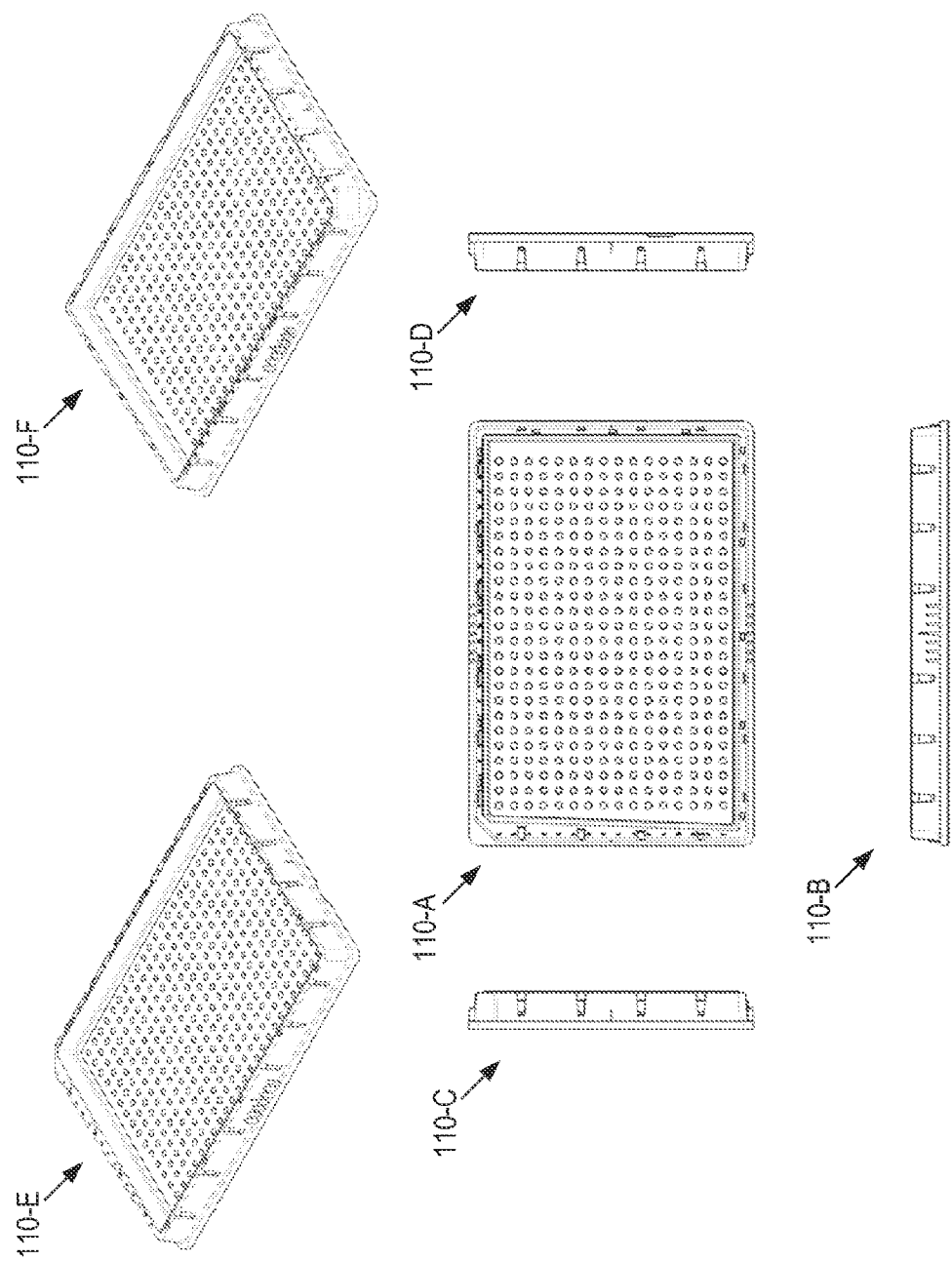

(A)

↓

620 Cool the plastic material to form a second structure so that the first structure and the second structure are coupled, the second structure including a base layer and one or more vertical structures along a periphery of the base layer, adjacent a first surface of the base layer. At least a portion of a first surface of the sheet layer of the first structure is exposed from the second structure, and a second surface of the sheet layer, opposite to the first surface of the sheet layer, is embedded in the base layer of the second structure adjacent the first surface of the base layer.

622 The plastic material of the second structure is optically transparent

624 Couple a third structure with at least the second structure over at least a portion of the one or more vertical structures, the third structure including one or more side walls

626 The one or more vertical structures of the second structure include a plurality of pins vertically protruding from the rest of the one or more vertical structures

628 Mold the third structure over at least a portion of the one or more vertical structures with a second mold so as to couple the second structure and the third structure, and remove a combination of the second structure and the third structure from the second mold by pushing respective locations on the third structure that correspond to the plurality of pins of the second structure.

630 The one or more side walls are made of a plastic material that has a glass transition temperature lower than the glass transition temperature of the second structure

632 The one or more vertical structures include one or more side walls

634 The one or more side walls are made of a material that has Shore A hardness of 85 or less 636 The one or more side walls each have an inner surface, an outer surface, a bottom adjacent the sheet layer of the first structure, and a top surface opposite the bottom, and a respective side wall of the one or more side walls includes one or more lips on the top surface, at least one of the one or more lips aligned with the inner surface of the respective side wall 638 The one or more side walls each have an inner surface, an outer surface, a bottom adjacent the sheet layer of the first structure, and a top surface opposite the bottom, and a respective side wall of the one or more side walls includes one or more vertical indentations along the outer surface of the respective side wall 640 The one or more side walls are made of a hydrophobic material of a surface tension lower than 35 dynes/cm 642 The one or more side walls each have an inner surface, an outer surface, a bottom adjacent the sheet layer of the first structure, and a top surface opposite the bottom, and the inner surface of a respective side wall of the one or more side walls is coated to expose a hydrophobic surface of a surface tension lower than 35 dynes/cm 644 The second structure includes a plurality of holding locations, the method comprising aligning the first structure and the second structure so that the plurality of discrete through holes defined in the sheet layer of the first structure is offset from the plurality of holding locations in the second structure

Figure 6C

646 The mold is configured so that a top surface of the sheet layer of the first structure is aligned with a top surface of the base layer of the second structure 648 The mold is configured so that a top surface of the sheet layer of the first structure is above a top surface of the base layer of the second structure 650 The mold is configured so that a top surface of the sheet layer of the first structure is below a top surface of the base layer of the second structure 652 The first surface of the mold has one or more of: a plurality of indentations and a plurality of protrusions corresponding to the plurality of discrete through holes defined in the sheet layer 654 At least one of the side walls include one or more handles, each handle comprising a plurality of parallel fins

Figure 6D

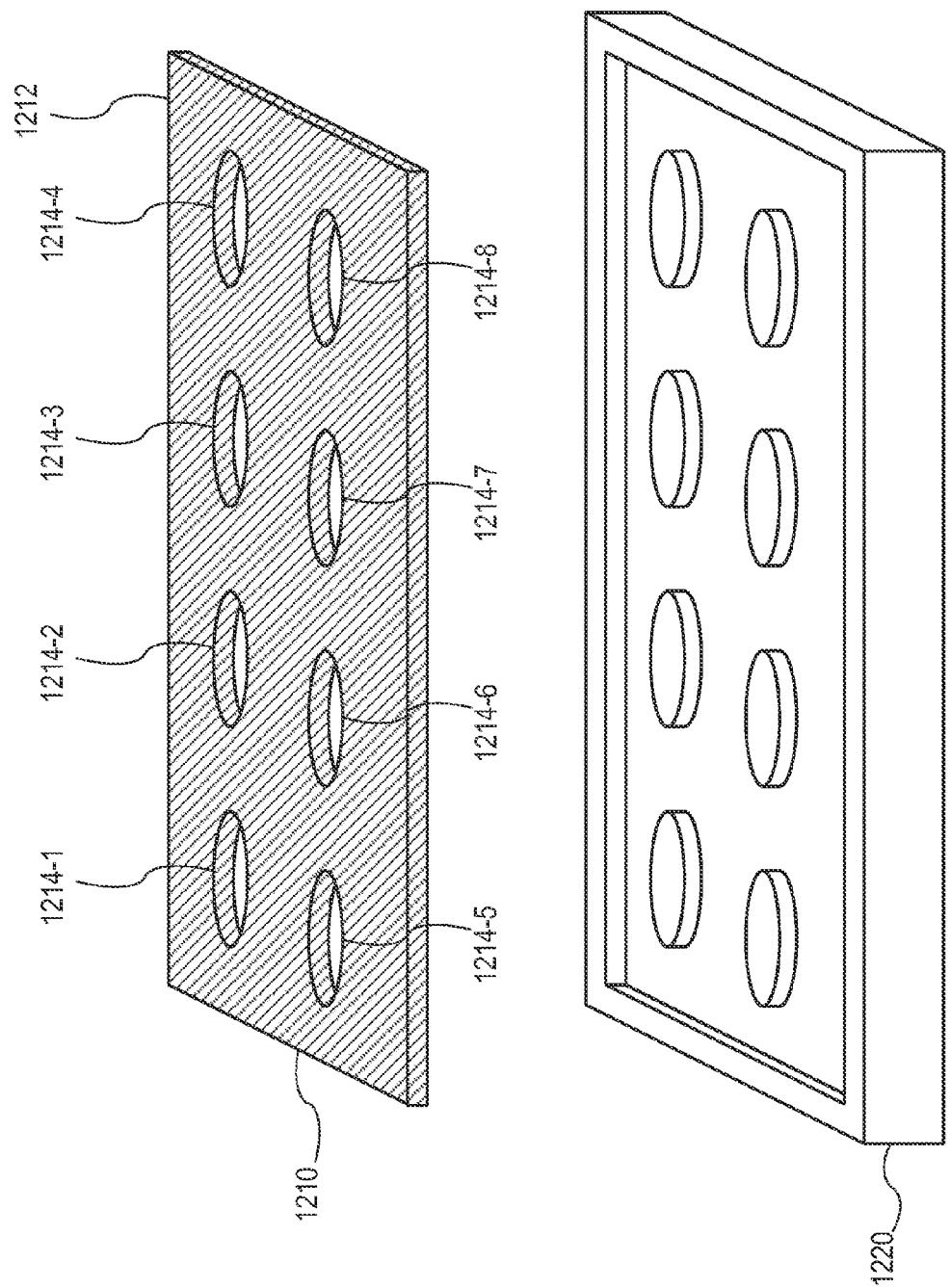

700

- 702 Provide a first structure in a mold. The first structure includes a sheet layer with a plurality of discrete through-holes.
  - 704 The sheet layer includes at least 50% of fluorocarbon by weight
  - 706 The sheet layer includes at least 90% of fluorocarbon by weight
  - 708 The sheet layer includes at least 95% of fluorocarbon by weight
  - 710 The sheet layer includes at least 99% of fluorocarbon by weight
  - 712 The sheet layer includes at least 90% of polytetrafluoroethylene by weight
  - 714 The sheet layer includes at least 95% of polytetrafluoroethylene by weight
  - 716 The sheet layer includes at least 99% of polytetrafluoroethylene by weight

- 718 Press the first structure against a first surface of a mold
  - 720 Pressing the first structure against the first surface of the mold includes pressing the first surface of the sheet layer against the first surface of the mold with a plurality of pins at least on the second surface of the sheet layer
  - 722 Provide vacuum suction on the first surface of the sheet layer

Figure 12A

736 At least a portion of a first surface of the sheet layer of the first structure is exposed from the second structure, and a second surface of the sheet layer, opposite to the first surface of the sheet layer, is embedded in the second structure

746 At least 90% of the exposed portion of the first surface is covered by fluorocarbon

748 At least 95% of the exposed portion of the first surface is covered by fluorocarbon

750 At least 99% of the exposed portion of the first surface is covered by fluorocarbon

752 At least 90% of the exposed portion of the first surface is covered by polytetrafluoroethylene

754 At least 95% of the exposed portion of the first surface is covered by polytetrafluoroethylene

756 At least 99% of the exposed portion of the first surface is covered by polytetrafluoroethylene

758 The exposed portion of the first surface is characterized (758) by advancing and receding contact angles, for a liquid selected from a group including water, ethanol, and isopropanol, that are similar to advancing and receding contact angles, for the selected liquid, on polytetrafluoroethylene

760 The second structure includes a plurality of holding locations. Align the first structure and the second structure so that the plurality of discrete through-holes defined in the sheet layer of the first structure is offset from the plurality of holding locations in the second structure.

Figure 12C

762 The mold is configured so that a top surface of the sheet layer of the first structure is aligned with a top surface of a base layer of the second structure 764 The mold is configured so that a top surface of the sheet layer of the first structure is above a top surface of a base layer of the second structure 766 The mold is configured so that a top surface of the sheet layer of the first structure is below a top surface of a base layer of the second structure 768 The first surface of the mold has one or more of: a plurality of indentations and a plurality of protrusions corresponding to the plurality of discrete through-holes defined in the sheet layer 770 At least a portion of the first surface of the sheet layer is embedded in the second structure 772 The first structure includes one or more connectors coupled to one or more sides of the sheet layer 774 The one or more connectors are embedded in the second structure 776 At least a portion of the sides of the sheet layer is angled 778 An inner wall of at least one discrete through-hole of the sheet layer is angled 780 The second surface of the sheet layer has a larger area than the first surface of the sheet layer 782 Coat a portion of the second structure with oil 784 Coat a portion of the first surface of the sheet layer of the first structure with the oil 786 The oil is selected from the group consisting of a mineral oil, a silicone oil, a hydrocarbon compound, a hydrofluorocarbon compound and a perfluorocarbon compound

Figure 12D

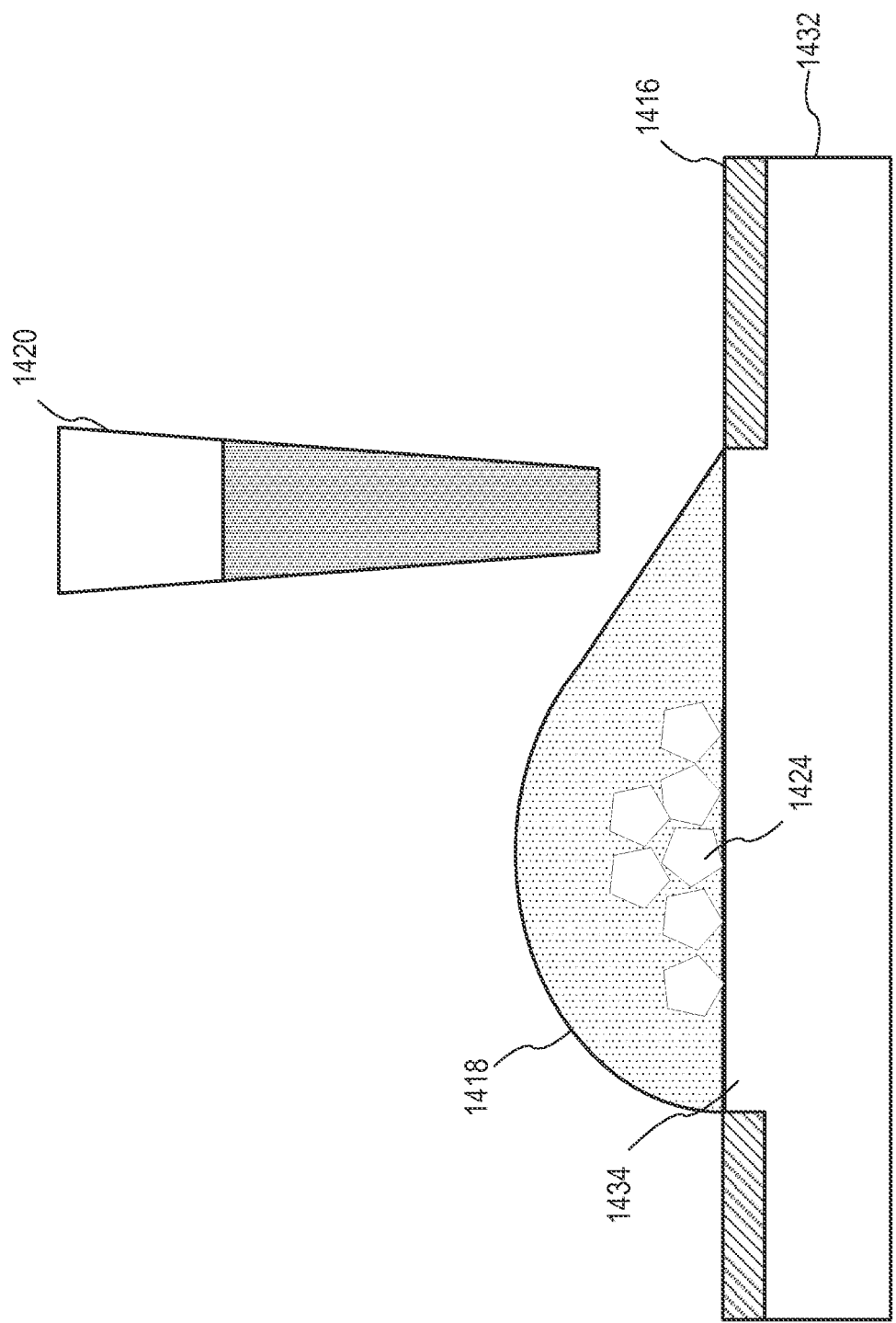

ARRAY PLATES FOR WASHING SAMPLES

RELATED APPLICATIONS

This application claims priority to U.S. Provisional Patent Application Ser. No. 61/844,046, filed Jul. 9, 2013 and U.S. Provisional Patent Application Ser. No. 61/968,249, filed Mar. 20, 2014, both of which are incorporated by reference herein in their entirety.

This application is related to the following applications: (1) U.S. patent application Ser. No. 11/984,197, filed Nov. 14, 2007, which is a continuation-in-part of Patent Cooperation Treaty Application Serial No. PCT/SG2006/000363, filed Nov. 24, 2006 and issued as U.S. Pat. No. 8,691,147; (2) U.S. patent application Ser. No. 12/282,162, filed Jan. 22, 2009, which is a national phase application of Patent Cooperation Treaty Application Serial No. PCT/SG06/00050, filed Mar. 9, 2006 and issued as U.S. Pat. No. 8,261,598; (3) U.S. patent application Ser. No. 13/264,913, filed Oct. 17, 2011, which issued as U.S. Pat. No. 8,784,752 and is a national phase application of Patent Cooperation Treaty Application Serial No. PCT/SG2010/000153, filed Apr. 16, 2010, which claims priority to U.S. Provisional Patent Application Ser. No. 61/170,201, filed Apr. 17, 2009; (4) U.S. patent application Ser. No. 13/811,638, filed Jan. 22, 2013, which is a national phase application of Patent Cooperation Treaty Application Serial No. PCT/SG2011/000263, filed Jul. 25, 2011, which claims priority to U.S. Provisional Patent Application Ser. No. 61/367,049, filed Jul. 23, 2010; (5) U.S. Provisional Application Ser. No. 61/711,725, filed Oct. 9, 2012; and (6) Patent Cooperation Treaty Application Serial No. PCT/US2013/024783, filed Feb. 5, 2013, which claims priority to U.S. Provisional Patent Application Ser. No. 61/595,131, filed Feb. 5, 2012 and U.S. Provisional Patent Application Ser. No. 61/711,127, filed Oct. 8, 2012. All of these applications are incorporated by reference herein in their entirety.

TECHNICAL FIELD

The disclosed embodiments relate generally to array plates and slides, and methods for making and using the same. More particularly, the disclosed embodiments relate to array plates and slides for biological and/or chemical reactions, and methods for making and using the same.

BACKGROUND

An array plate is also called a microtiter plate, microplate, or microwell plate. Array plates are typically used to hold respective liquid droplets separately for biological and/or chemical reaction. For example, a well-type array plate includes a plurality of wells so that each liquid droplet or each sample may be dispensed into a separate well for further processing. Typically, the number of wells is selected from 6, 24, 96, 384, 1536, 3456, and 9600.

Alternatively, hydrophobic material-coated slides have been used for holding larger volumes of droplets on a microscope slide surface. For example, the PTFE matrix is patterned on a glass slide (e.g., a microscope slide) so that the PTFE matrix covers portions of the glass microscope slide and the remaining portions of the glass microscope slide are not covered by the PTFE matrix. The PTFE matrix has hydrophobic characteristics and the portions of the glass microscope slide that are not covered by the PTFE matrix have hydrophilic characteristics. Aqueous solutions that include samples (e.g., cells) are typically placed on hydrophilic areas of the slide.

Samples (e.g., cells) are frequently washed. Washing typically involves adding a wash solution to a sample solution, including samples (e.g., cells), on the slide and removing the mixture of the wash solution and the sample solution. However, certain cells (e.g., suspension cells, non-adherent cells, and weakly adherent cells) do not strongly adhere to the slide. Thus, during removal of the mixture, cells may be removed along with the mixture, thereby reducing the number of cells that remain on the hydrophilic area of the slide after the washing. Because a reliability of cell-based reactions typically requires a sufficient number of cells, the loss of cells during washing negatively affects cell-based reactions.

SUMMARY

Accordingly, there is need for slides and plates that better retain cells during washing. Such slides and plates may replace the conventional slides and plates in washing cells. Such slides and methods reduce or eliminate the loss of cells during washing, thereby improving the reliability of cell-based reactions. Similarly, such slides and plates may be used in washing other types of samples, such as beads or particles conjugated with target molecules.

A number of embodiments that overcome the limitations and disadvantages of existing array plates and slides are presented in more detail below. These embodiments provide array plates and slides for washing a sample in a sample solution and methods for making and using the same.

As described in more detail below, in accordance with some embodiments, a device includes a first structure that includes a sheet layer with a plurality of discrete through holes; and a second structure coupled to the first structure, the second structure including a base layer and one or more vertical structures along a periphery of the base layer, adjacent to a first surface of the base layer. At least a portion of a first surface of the sheet layer of the first structure is exposed from the second structure. A second surface of the sheet layer, opposite to the first surface of the sheet layer, is embedded in the base layer of the second structure adjacent to the first surface of the base layer. At least some of the plurality of discrete through holes define a plurality of primary areas and a plurality of secondary areas on the base layer of the second structure, one or more secondary areas adjacent to a respective primary area.

In some embodiments, a device includes a first structure that includes a sheet layer; and a second structure coupled to the first structure. At least a portion of a first surface of the sheet layer of the first structure is exposed from the second structure, and the sheet layer defines a plurality of primary areas and a plurality of secondary areas, one or more secondary areas adjacent to a respective primary area.

In some embodiments, a respective primary area of the above-described device is covered with a sample solution. A method for washing a sample in the sample solution includes dispensing a wash solution to a respective secondary area of the one or more secondary areas, thereby mixing the wash solution and the sample solution; and removing at least a portion of the mixed solution. In some embodiments, removing at least the portion of the mixed solution includes removing at least the portion of the mixed solution without removing the sample.

In some embodiments, a device includes a first structure including a sheet layer with a plurality of discrete through holes; and a second structure coupled to the first structure. At least a portion of a first surface of the sheet layer of the first structure is exposed from the second structure. A second surface of the sheet layer, opposite to the first surface of the sheet layer, is embedded in the second structure. At least a portion of the second structure is exposed through at least some of the plurality of discrete through holes. The exposed portion of the second structure includes a plurality of primary areas and a plurality of second areas, one or more secondary areas adjacent to a respective primary area.

In some embodiments, a respective primary area, on the second structure of the above-described device is covered with a sample solution. A method for washing a sample in the sample solution includes dispensing a wash solution to a respective secondary area, thereby mixing the wash solution and the sample solution; and removing at least a portion of the mixed solution. In some embodiments, removing at least the portion of the mixed solution includes removing at least the portion of the mixed solution without removing the sample.

In some embodiments, a sample solution is located on a hydrophilic area of a respective area of an array plate and a remainder of the respective area includes a hydrophobic area. A method for washing a sample in the sample solution includes placing a pipette tip in proximity to the sample solution in accordance with predefined proximity criteria; dispensing a wash solution in accordance with predefined dispensing criteria, thereby mixing the wash solution and the sample solution; and removing at least a portion of the mixed solution. In some embodiments, removing at least the portion of the mixed solution includes removing at least the portion of the mixed solution without removing the sample.

In some embodiments, a method for manufacturing an array plate includes providing a first structure, the first structure including a sheet layer with a plurality of discrete through holes. The method includes pressing the first structure against a first surface of a mold, providing a heated plastic material into the mold, and cooling the plastic material to form a second structure so that the first structure and the second structure are coupled. The second structure includes a base layer and one or more vertical structures along a periphery of the base layer, adjacent to a first surface of the base layer. At least a portion of a first surface of the sheet layer of the first structure is exposed from the second structure, and a second surface of the sheet layer, opposite to the first surface of the sheet layer, is embedded in the base layer of the second structure adjacent to the first surface of the base layer.

In accordance with some embodiments, a device includes an array plate manufactured by the aforementioned method.

In accordance with some embodiments, a device includes a first structure, the first structure including a sheet layer with a plurality of discrete through holes. The device includes a second structure coupled to the first structure, the second structure including a base layer and one or more vertical structures along a periphery of the base layer, adjacent to a first surface of the base layer. At least a portion of a first surface of the sheet layer of the first structure is exposed from the second structure, and a second surface of the sheet layer, opposite to the first surface of the sheet layer, is embedded in the base layer of the second structure adjacent to the first surface of the base layer.

In accordance with some embodiments, a method includes providing a device of the aforementioned devices, the device defining a reservoir. The method includes storing a liquid medium in the reservoir of the device so that the first surface of the sheet layer is covered by the liquid medium, and dispensing respective liquid droplets on respective locations on the base layer. The respective locations correspond to locations of the plurality of discrete through holes defined in the sheet layer, and the respective liquid droplets are immiscible with the liquid medium. In some embodiments, the method includes adding one or more solutions to one or more liquid droplets of the respective liquid droplets. In some embodiments, the method includes performing an immunoassay by immobilizing one of one or more antibodies and one or more antigens in one or more respective liquid droplets to the base layer; adding one or more solutions to the one or more respective liquid droplets of the respective liquid droplets, at least one of the one or more solutions including the other of the one or more antibodies and the one or more antigens; and detecting a binding of the at least one antigen with at least one antibody in the one or more respective liquid droplets. In some embodiments, the method includes washing the respective liquid droplets on the device by: removing a portion of the liquid medium; adding a wash buffer to the reservoir; shaking the device so that the wash buffer and the respective liquid droplets are mixed; draining at least a portion of the wash buffer from the reservoir; and providing a liquid medium in the reservoir of the device so that the first surface of the sheet layer is covered by the liquid medium.

Some embodiments involve a method for manufacturing an array slide. The method includes providing a first structure in a mold. The first structure includes a sheet layer with a plurality of discrete through holes. The method also includes providing a heated plastic material into the mold and cooling the plastic material to form a second structure so that the first structure and the second structure are coupled. At least a portion of a first surface of the sheet layer of the first structure is exposed from the second structure, and a second surface of the sheet layer, opposite to the first surface of the sheet layer, is embedded in the second structure.

Some embodiments involve an array slide manufactured by the aforementioned method.

In accordance with some embodiments, an array slide includes a first structure including a sheet layer with a plurality of discrete through holes; and a second structure coupled to the first structure. At least a portion of a first surface of the sheet layer of the first structure is exposed from the second structure. A top portion of the sheet layer, including the exposed portion of the first surface of the sheet layer, includes at least 95% of fluorocarbon by weight. A second surface of the sheet layer, opposite to the first surface of the sheet layer, is embedded in the second structure.

In accordance with some embodiments, an array slide includes a plurality of primary areas and a plurality of secondary areas, one or more secondary areas adjacent to a respective primary area. In some embodiments, the plurality of primary areas are surrounded by one or more background areas and indented from the one or more background areas. In some embodiments, the plurality of primary areas includes hydrophilic areas. In some embodiments, the plurality of secondary areas includes hydrophilic areas. In some embodiments, the one or more background areas include hydrophobic areas.

In accordance with some embodiments, a method includes providing a device that includes a plurality of primary areas and a plurality of secondary areas. One or more secondary areas of the plurality of secondary areas are distinct and separate from a respective primary area. The one or more secondary areas of the plurality of secondary areas are adjacent to the respective primary area. The plurality of primary areas and the plurality of secondary areas are hydrophilic areas surrounded by hydrophobic areas. The respective primary area is covered with a first solution. The method also includes dispensing a second solution, distinct from the first solution, to a respective secondary area of the one or more secondary areas adjacent to the respective primary area, thereby mixing the first solution on the respective secondary area and the second solution on the respective primary area. A mixed solution is formed by mixing the first solution and the second solution.

In some embodiments, the method includes removing at least a portion of the mixed solution.

In some embodiments, dispensing the second solution includes dropping one or more droplets of the second solution to the respective secondary area.

In some embodiments, the method includes repeating dispensing the second solution to the respective secondary area and removing at least a portion of the mixed solution.

In some embodiments, the first solution is a sample solution that includes a sample and the second solution is a wash solution.

In some embodiments, the method includes removing at least a portion of the mixed solution from the respective secondary area.

In some embodiments, the method includes, while dispensing the second solution, concurrently removing at least a portion of the mixed solution from a secondary area distinct from the respective secondary area.

In some embodiments, the respective primary area is connected to the respective primary area with a dispensing channel, and the second solution has a dispensing velocity at a narrowest portion of the dispensing channel. A product of the dispensing velocity and a width of the dispensing channel at the narrowest portion divided by a kinematic viscosity of the second solution is not more than one.

In some embodiments, the mixed solution is removed at a removal velocity at a narrowest portion of a removal channel that connects the respective primary area and a secondary area from which the mixed solution is removed, a product of the removal velocity and a width of the removal channel divided by the kinematic viscosity of the mixed solution is not more than one.

In some embodiments, dispensing the wash solution includes dropping one or more droplets of the wash solution onto the respective secondary area.

In some embodiments, the respective primary area is indented from a surrounding hydrophobic area.

In some embodiments, the respective primary area is indented from a surrounding hydrophobic area by a first distance and the respective secondary area is indented from a surrounding hydrophobic area by a second distance that is distinct from the first distance.

In some embodiments, the respective secondary area is not indented from a surrounding hydrophobic area.

In some embodiments, dispensing the second solution includes placing a pipette tip in proximity to the first solution in accordance with predefined proximity criteria; and dispensing the second solution in accordance with predefined dispensing criteria, thereby mixing the first solution and the second solution.

In some embodiments, the respective primary area and the respective secondary area have distinct sizes.

In accordance with some embodiments, a system includes a device holder for holding a device that includes a plurality of primary areas and a plurality of secondary areas. One or more secondary areas of the plurality of secondary areas are distinct and separate from a respective primary area and adjacent to the respective primary area. The plurality of primary areas and the plurality of secondary areas are hydrophilic areas surrounded by hydrophobic areas. The respective primary area is covered with a first solution. One or more dispensers configured to dispense a second solution to the device. One or more dispenser actuators for positioning a respective dispenser above the respective secondary area of the device held in the device holder.

In some embodiments, one or more droplets are located on the device; the system includes one or more sensors to locate a meniscus of a respective droplet on the device; and the one or more dispenser actuators are configured to position the respective dispenser so that at least a tip of the respective dispenser is located within the respective droplet while dispensing at least a portion of the second solution.

In some embodiments, the system includes one or more aspirators configured to remove at least a portion of a solution located on the respective primary area; and one or more aspirator actuators for positioning a respective aspirator above a secondary area of the respective device held in the device holder.

In some embodiments, a respective dispenser is positioned above the respective secondary area while dispensing the second solution to the respective secondary area and a respective aspirator is positioned above the secondary area while removing at least a portion of the solution located on the respective primary area.

In some embodiments, the system is configured to concurrently dispense the second solution while removing at least a portion of the solution located on the respective primary area.

BRIEF DESCRIPTION OF THE DRAWINGS

For a better understanding of the aforementioned embodiments as well as additional embodiments, reference should be made to the Description of Embodiments below, in conjunction with the following drawings in which like reference numerals refer to corresponding parts throughout the figures.

FIG. 3C-1 is a partial sectional view of the exemplary array plate corresponding to a portion of the cross-sectional view illustrated in FIG. 3C in accordance with some embodiments.

FIG. 3E-1 is a partial sectional view of the exemplary array plate corresponding to a portion of the cross-sectional view illustrated in FIG. 3E in accordance with some embodiments.

FIG. 3G-1 is a partial sectional view of the exemplary array plate corresponding to a portion of the cross-sectional view illustrated in FIG. 3G in accordance with some embodiments.

FIGS. 6A-6D are flow charts representing a method of making an array plate in accordance with some embodiments.

FIG. 8C is an exploded view of an exemplary array slide in accordance with some embodiments.

FIGS. 12A-12D are flow charts representing a method of making an array slide in accordance with some embodiments.

FIGS. 14B-14D are cross-sectional views of exemplary array slides in accordance with some embodiments.

Like reference numerals refer to corresponding parts throughout the drawings.

DESCRIPTION OF EMBODIMENTS

Array plates and slides, and methods for making and using the array plates and slides, are described. Reference will be made to certain embodiments, examples of which are illustrated in the accompanying drawings. While the claims will be described in conjunction with the embodiments, it will be understood that it is not intended to limit the claims to these particular embodiments alone. On the contrary, the embodiments are intended to cover alternatives, modifications and equivalents that are within the spirit and scope of the appended claims.

Moreover, in the following description, numerous specific details are set forth to provide a thorough understanding of the embodiments. However, it will be apparent to one of ordinary skill in the art that the embodiments may be practiced without these particular details. In other instances, methods, procedures, components, and networks that are well-known to those of ordinary skill in the art are not described in detail to avoid obscuring aspects of the embodiments.

It will also be understood that, although the terms first, second, etc. may be used herein to describe various elements, these elements should not be limited by these terms. These terms are only used to distinguish one element from another. For example, a first surface could be termed a second surface, and, similarly, a second surface could be termed a first surface, without departing from the scope of the embodiments. The first surface and the second surface are both surfaces, but they are not the same surface.

The terminology used in the description of the embodiments herein is for the purpose of describing particular embodiments only and is not intended to be limiting of the invention. As used in the description of the embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, a liquid droplet refers to an aliquot of a liquid. A droplet may have any shape, and the term "droplet" is not used herein to describe a particular shape.

Array Plates and Methods for Making the Array Plates

Figure 3A:
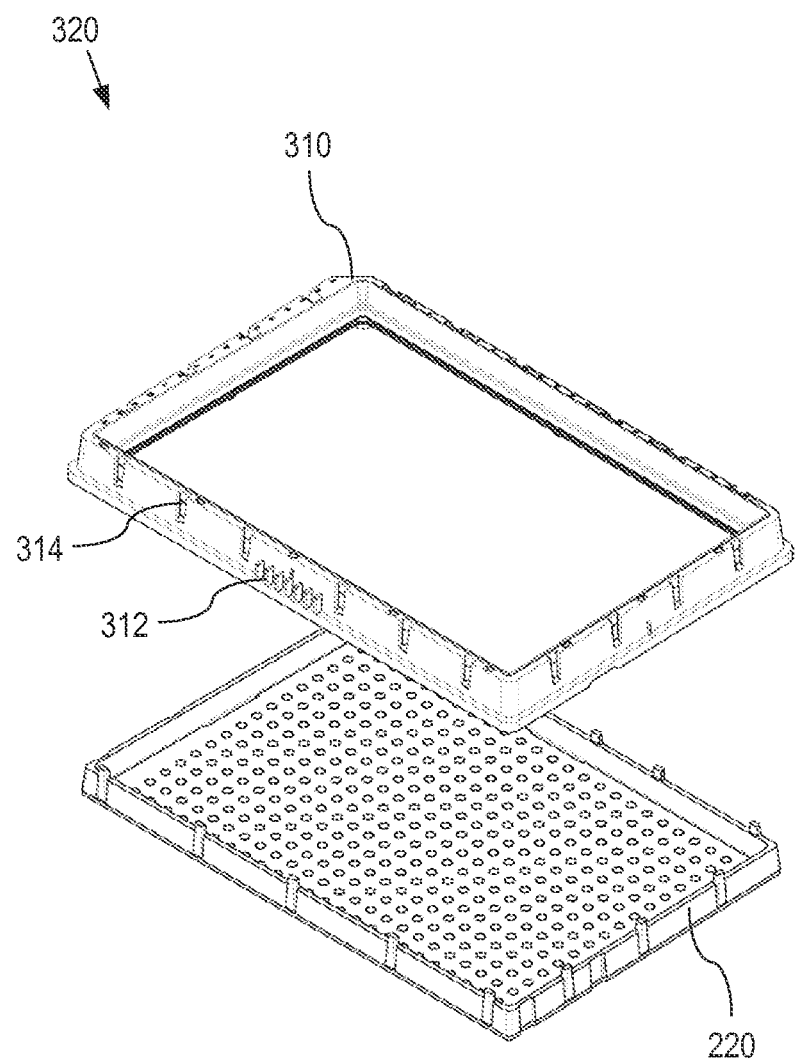
FIG. 3A is an exploded view of an exemplary array plate in accordance with some embodiments.
Figure 3B:
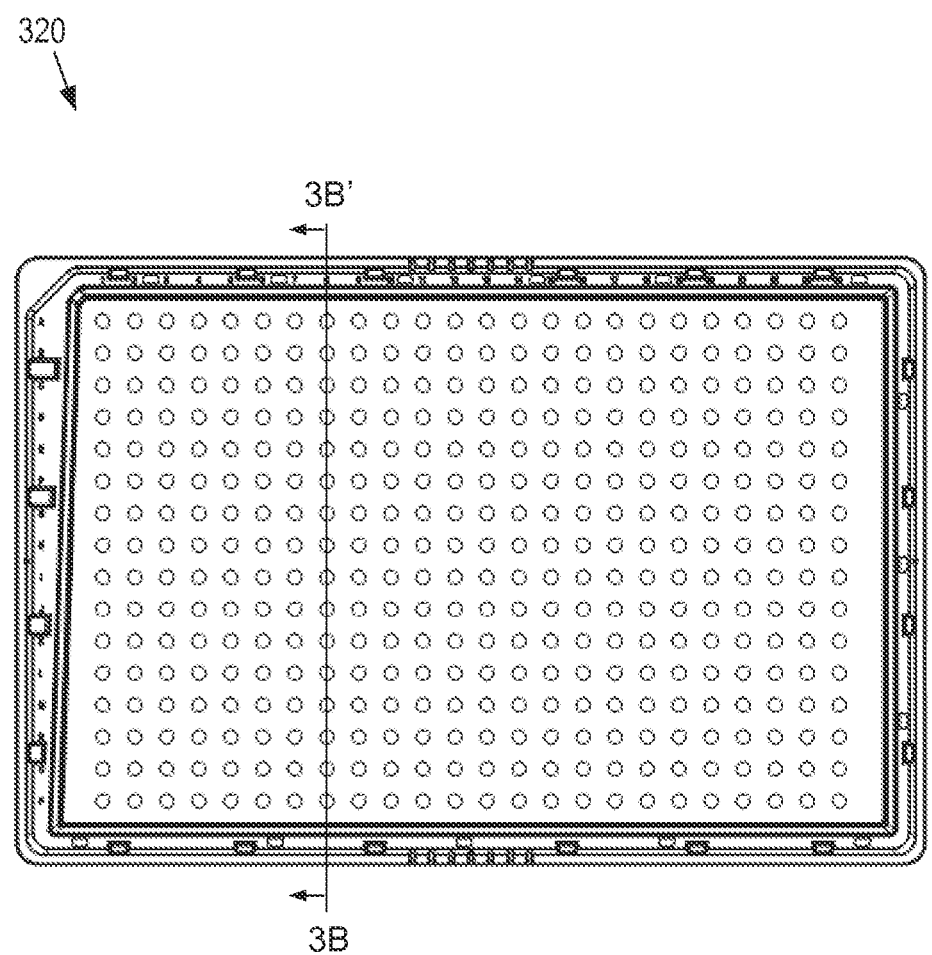
FIGS. 3B, 3D, and 3F are top perspective views of an exemplary array plate in accordance with some embodiments.
Figure 3C:
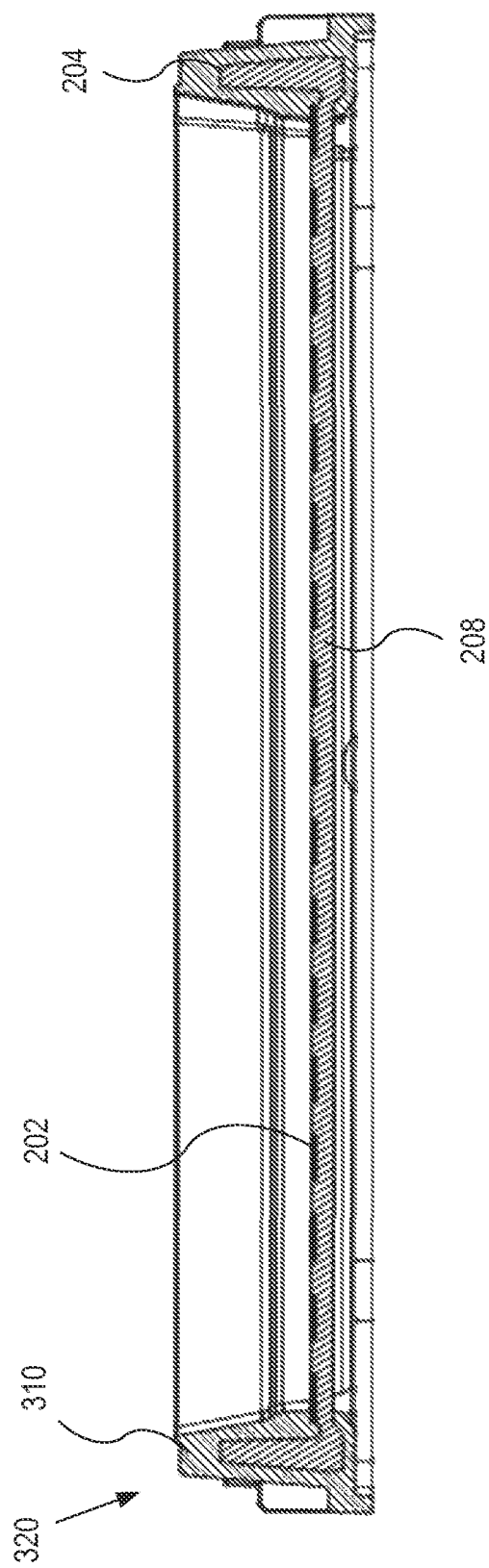
FIG. 3C is a cross-sectional view of the exemplary array plate corresponding to a section indicated in FIG. 3B in accordance with some embodiments.
Figures 1, 3C:
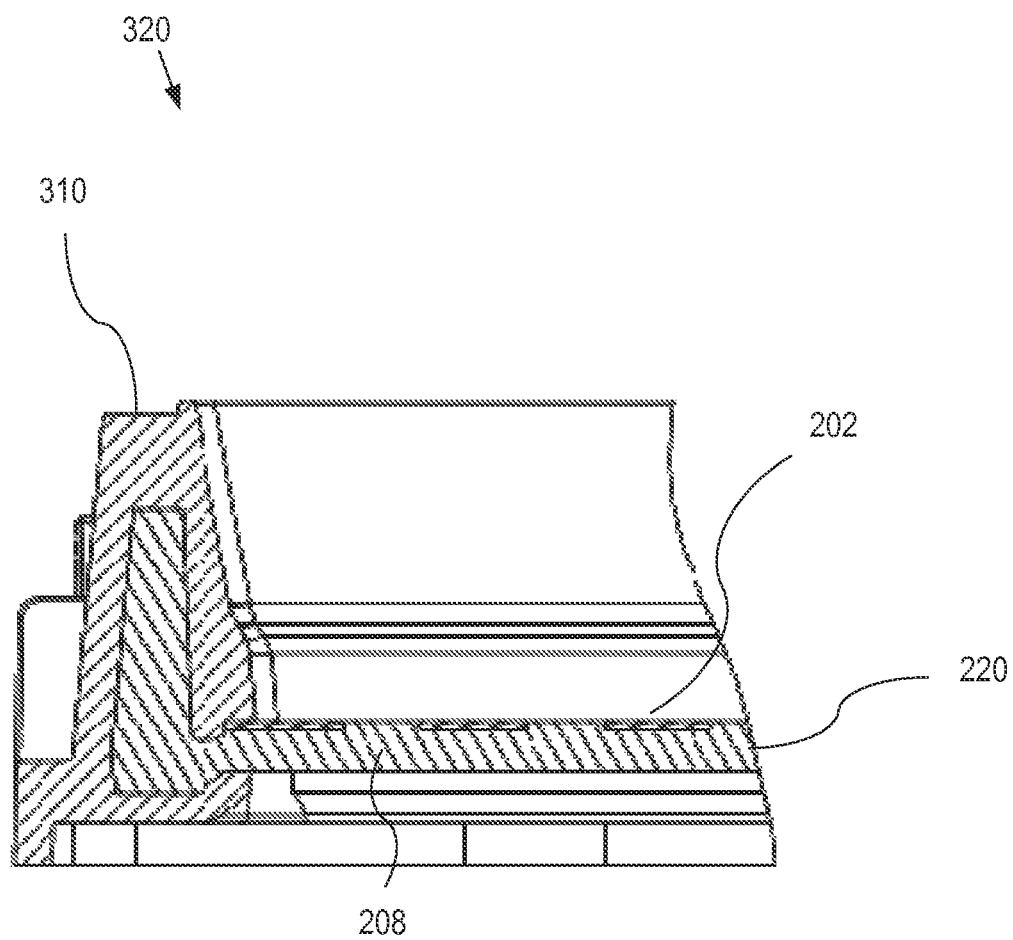
FIG. 1 is perspective views of an exemplary array plate in accordance with some embodiments.

FIG. 1 is perspective views of an exemplary array plate in accordance with some embodiments. In particular, FIG. 1 includes a top perspective view 110-A, a front perspective view 110-B, a left perspective view 110-C, a right perspective view 110-D, and oblique perspective views 110-E and 110-F of an exemplary array plate 110.

The exemplary array plate 110 includes at least a combination of a first structure (e.g., a plate) and a second structure (e.g., a frame). The details of the first structure and the second structure are described with respect to FIGS. 2A-2G below.

Figure 2A:
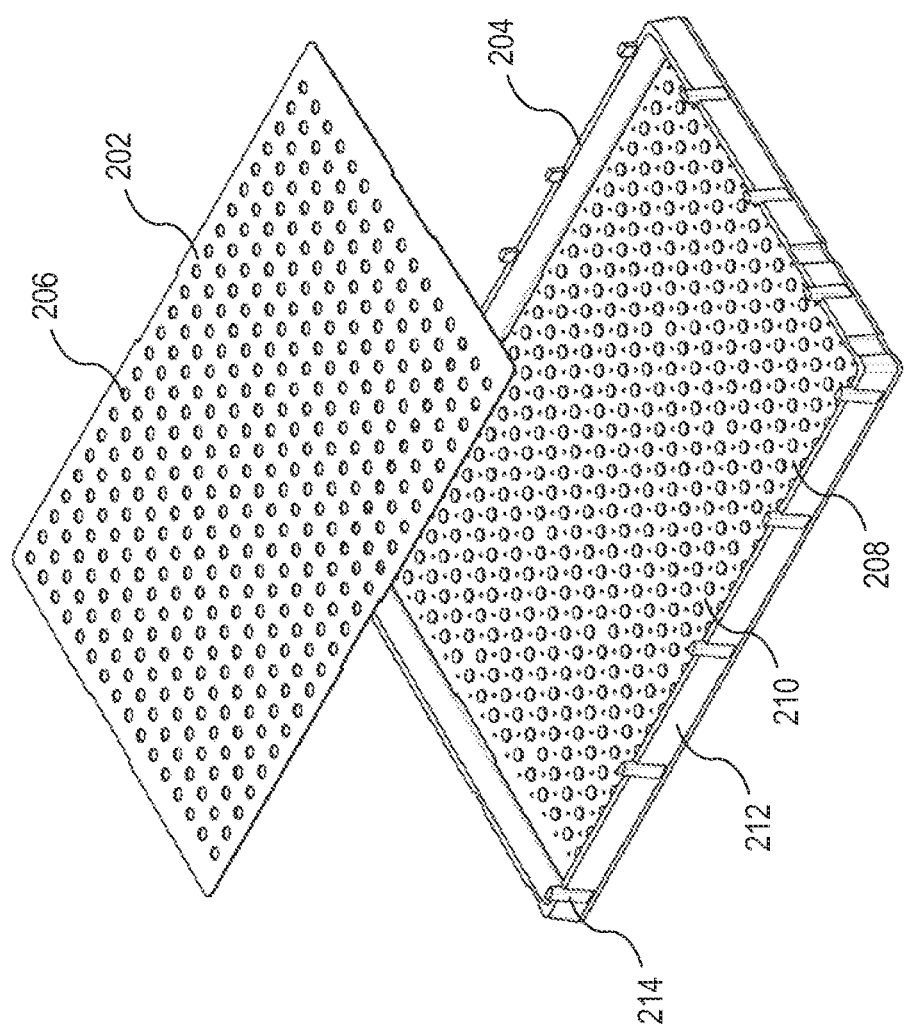
FIG. 2A is an exploded view of an exemplary combination of a first structure and a second structure in accordance with some embodiments.

FIG. 2A is an exploded view of an exemplary combination of a first structure 202 and a second structure 204 in accordance with some embodiments. The first structure 202 includes a sheet layer that typically has a square or rectangular planar shape. Alternatively, the sheet layer of the first structure 202 may have a round shape, such as a circle or an oval. Optionally, the first structure 202 may also include additional features, such as one or more vertical structures described below (e.g., the first structure 202 may be a tray including the sheet layer and one or more short sidewalls). In some embodiments, the sheet layer of the first structure 202 includes a sheet of a preselected material of a predefined thickness. The preselected material includes a polymer (e.g., polytetrafluoroethylene, any other perfluorocarbon polymer, or any other fluorocarbon polymer). The sheet layer has a thickness typically of 0.01-10 mm, 0.1-2 mm, 0.2-1 mm, or 1-2 mm.

A plurality of discrete through holes 206 are defined in the sheet layer of the first structure 202. The plurality of discrete through holes 206 are formed by punching holes through the sheet layer of the first structure 202 (which typically includes a polymer). In some embodiments, the plurality of discrete through holes have substantially the same diameter (e.g., with less than 50, 30, 20, 10, or 5% variation among the holes). In some embodiments, the plurality of discrete through holes have different diameters (e.g., a first group of discrete through holes have a first diameter and a second group of discrete through holes have a second diameter). In some embodiments, a respective through hole has a 1 mm-5 mm diameter, or 2 mm-3 mm diameter. In some embodiments, the discrete through holes are arranged in a predefined pattern. For example, when 96 discrete through holes are defined in the sheet layer of the first structure 202, the 96 discrete through holes are arranged in an 8×12 array. In some embodiments, the discrete through holes have a predefined spacing.

In some embodiments, the sheet layer of the first structure 202 includes at least 50% of fluorocarbon by weight. Alternatively, the sheet layer of the first structure 202 may include at least 60, 70, 80, 90, 95, or 99% of fluorocarbon by weight. In some embodiments, the sheet layer of the first structure 202 includes at least 90% of polytetrafluoroethylene by weight. Alternatively, the sheet layer of the first structure 202 may include at least 50, 60, 70, 80, 95, or 99% of polytetrafluoroethylene by weight.

In some embodiments, a first surface (e.g., a surface facing away from the second structure 204) of the first structure 202 is roughened to increase the hydrophobicity and/or oleophobicity.

In some embodiments, at least the first surface of the first structure 202 is coated with a material of at least 50% of fluorocarbon by weight. The thickness of the coated material may be as thin as 1 nm, 2 nm, 5 nm, or 10 nm.

The second structure 204 includes a base layer 208 and one or more vertical structures 212 along, or adjacent to, a periphery of the base layer 208, adjacent to a first surface of the base layer 208 (e.g., a top surface of the base layer 208 facing the first structure 202 as illustrated in FIG. 2A). As used herein, a vertical structure 212 refers to a structure protruding from a plane defined by the base layer 208. The vertical structure 212 typically defines a plane that is substantially perpendicular to the plane defined by the base layer 208 (e.g., the angle formed by the vertical structure 212 and the base layer 208 is 45° or less). In some embodiments, the one or more vertical structures 212 typically have at least 3 mm height. Alternatively, the one or more vertical structures 212 may have 1 mm, 2 mm, 4 mm, 5 mm, 6 mm, 8 mm, 10 mm, 12 mm, 14 mm, or 15 mm height. In some embodiments, the one or more vertical structures 212 have 0.1-5 mm width. Alternatively, the one or more vertical structures 212 may have 1-4 mm, 1-3 mm, 2-4 mm, 1-2 mm, or 2-3 mm width. In some embodiments, the one or more vertical structures 212 are configured to form a reservoir with the base layer 208. In other words, the reservoir is defined by the one or more vertical structures 212 and the base layer 208. In such embodiments, the reservoir formed by the one or more vertical structures of the second structure holds liquid without leaks. In some embodiments, the reservoir formed by the first structure and the second structure is configured to store at least a predefined volume of liquid (e.g., 1 ml, 5 ml, 10 ml, 20 ml, 50 ml, 100 ml, etc.).

In some embodiments, the base layer 208 of the second structure 204 includes a plurality of structures 210 that correspond to the plurality of discrete through holes in the first structure 202. In some embodiments, the second structure 204 is configured to mate with the first structure 202.

In some embodiments, the one or more vertical structures 212 include a plurality of pins 214. In some embodiments, the plurality of pins 214 vertically protrudes from the rest of the one or more vertical structures (e.g., a tip of a pin 214 is located further away from the rest of the one or more vertical structures). In some embodiments, the pins 214 provide additional stiffness for the one or more vertical structures 212. In some embodiments, the pins 214 also provide additional stiffness for the one or more side walls formed over the one or more vertical structures 212 so that the one or more side walls may maintain a flat top surface. In some embodiments, the pins 214 are used to remove an array plate from a mold, the process of which is described below with respect to FIG. 3J.

The second structure 204 typically includes a plastic material. In some embodiments, the plastic material includes polycarbonates. In some embodiments, the plastic material includes polystyrene. In some embodiments, the plastic material includes cyclic olefin polymer or copolymer.

In some embodiments, the plastic material of the second structure 204 is optically transparent. This allows the second structure 204 to be optically imaged from a bottom surface side of the base layer 208 facing away from the first structure 202. In order to obtain high quality images, it is important to keep the first structure and the second structure.

Figure 2B:
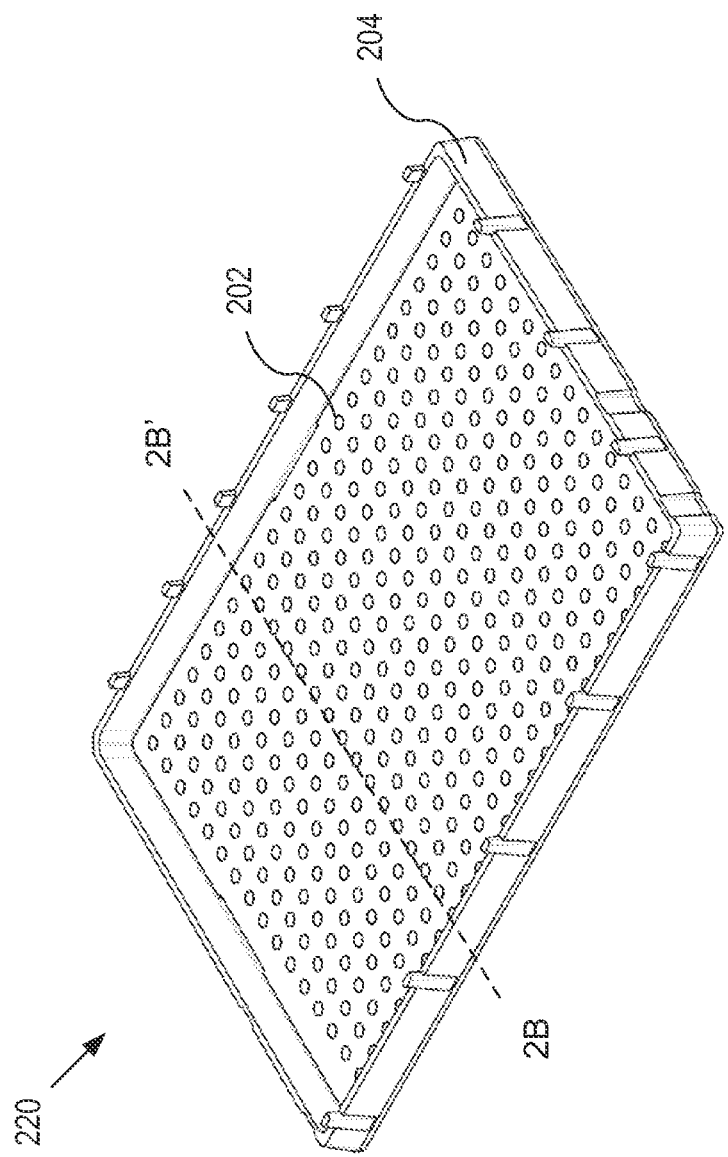
FIG. 2B is a perspective view of the exemplary combination of the first structure and the second structure in accordance with some embodiments.

FIG. 2B is a perspective view of the exemplary combination 220 of the first structure 202 and the second structure 204 in accordance with some embodiments.

In some embodiments, the combination 220 of the first structure 202 and the second structure 204 is made by forming the second structure 204 through a molding process while the first structure is placed in a mold. The details of the molding process are described with respect to FIGS. 2E-2H below. Alternatively, the first structure 202 and the second structure 204 may be separately manufactured and subsequently attached together. However, forming the second structure through the molding process provides several advantages, including a better seal between the first structure and the second structure, the absence of glue or adhesives in forming the combination 220 of the first structure 202 and the second structure 204, and also a reduced number of manufacturing steps. The absence of glue or adhesives reduces the interference on biological experiments on the plate.

FIG. 2B also indicates a line 2B-2B' across the combination 220 of the first structure 202 and the second structure 204. The line 2B-2B' corresponds to the cross-sectional view illustrated in FIG. 2C.

Figure 2C:
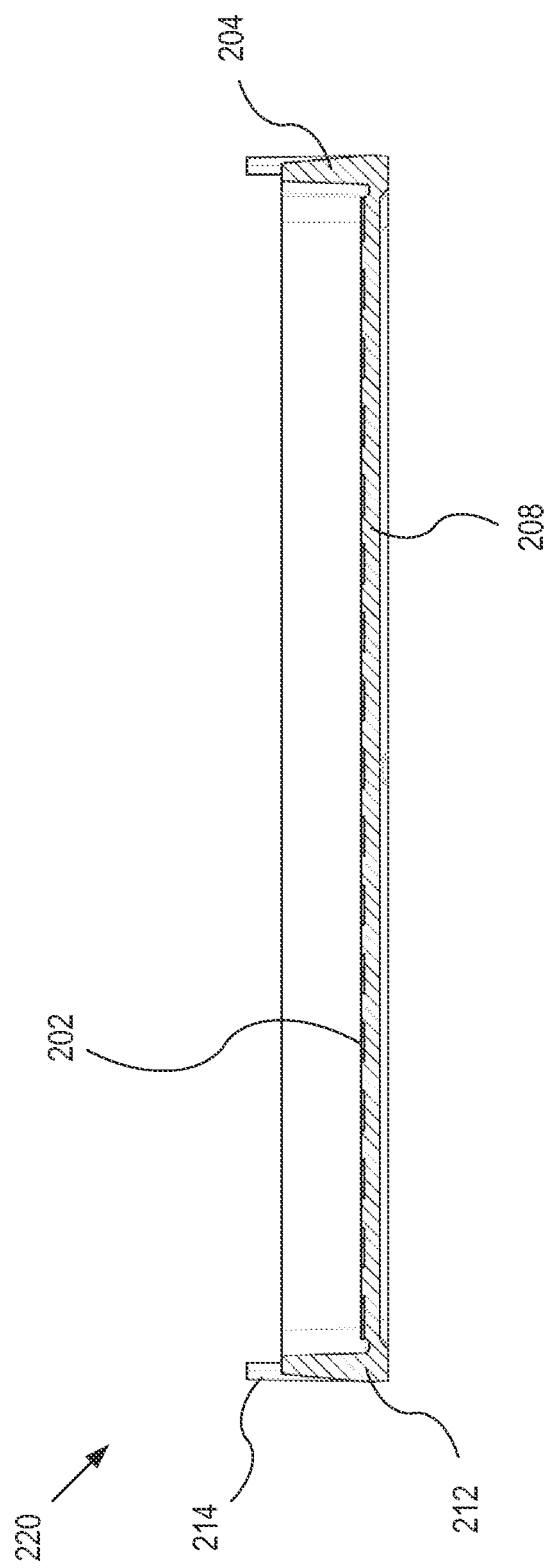
FIG. 2C is a cross-sectional view of the exemplary combination of the first structure and the second structure in accordance with some embodiments.

FIG. 2C is a cross-sectional view of the exemplary combination 220 of the first structure 202 and the second structure 204 in accordance with some embodiments. FIG. 2C also illustrates a pin 214 that vertically protrudes from the rest of the second structure 204 and a base layer 208.

Figure 2D:
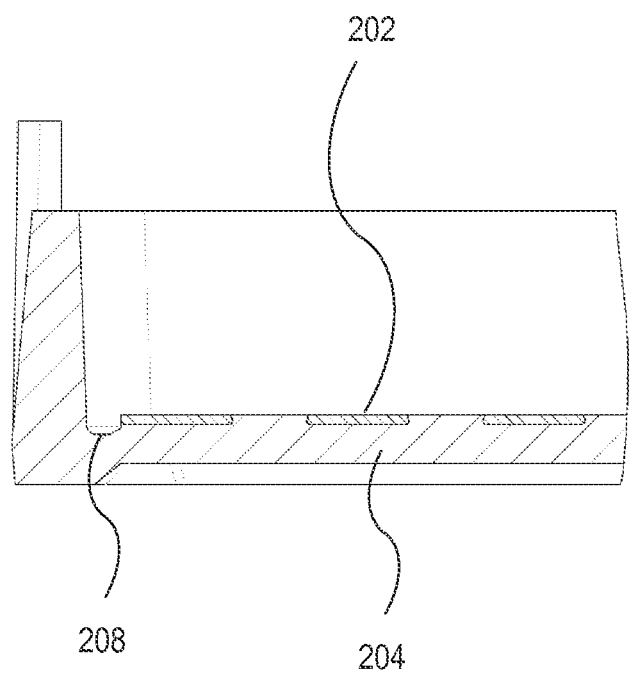
FIG. 2D is a partial sectional view of the exemplary combination illustrated in FIG. 2C in accordance with some embodiments.

FIG. 2D is a partial sectional view of the exemplary combination 220 illustrated in FIG. 2C, near the junction of the base layer 208 and the one or more vertical structures 212, in accordance with some embodiments. When the second structure 204 is formed by a molding process, the base layer 208 and the one or more vertical structures 212 are integrally formed so that there is no hole or gap through which liquids leak.

As shown in FIG. 2D, in the combination 220 of the first structure 202 and the second structure 204, at least a portion of a first surface of the sheet layer of the first structure 202 (e.g., a top surface of the sheet layer of the first structure 202 facing away from the second structure 204) is exposed from the second structure 204, and a second surface of the sheet layer, opposite to the first surface of the sheet layer, (e.g., a bottom surface of the sheet layer of the first structure 202 facing the base layer 208 of the second structure 204) is embedded in the base layer 208 of the second structure 204 adjacent to the first surface of the base layer 208. In other words, the top surface of the sheet layer of the first structure 202 is not entirely covered by the second structure 204. However, in some embodiments, a portion of the top surface of the sheet layer of the first structure 202 (e.g., along the periphery of the first structure) is covered by the second structure 204. The bottom surface of the sheet layer of the first structure 202 is in contact with the base layer 208 of the second structure 204.

In some embodiments, the first structure 202 and the second structure 204 have a surface tension difference of more than 10 dynes/cm. In some embodiments, the second structure 204 is more hydrophilic than the first structure 202, and the first structure 202 is more hydrophobic than the second structure 204.

FIGS. 2E-2H are schematic diagrams illustrating selected steps for manufacturing an exemplary combination 220 of a first structure 202 and a second structure 204 in accordance with some embodiments. The elements in FIGS. 2E-2H are not drawn to scale.

Figure 2E:
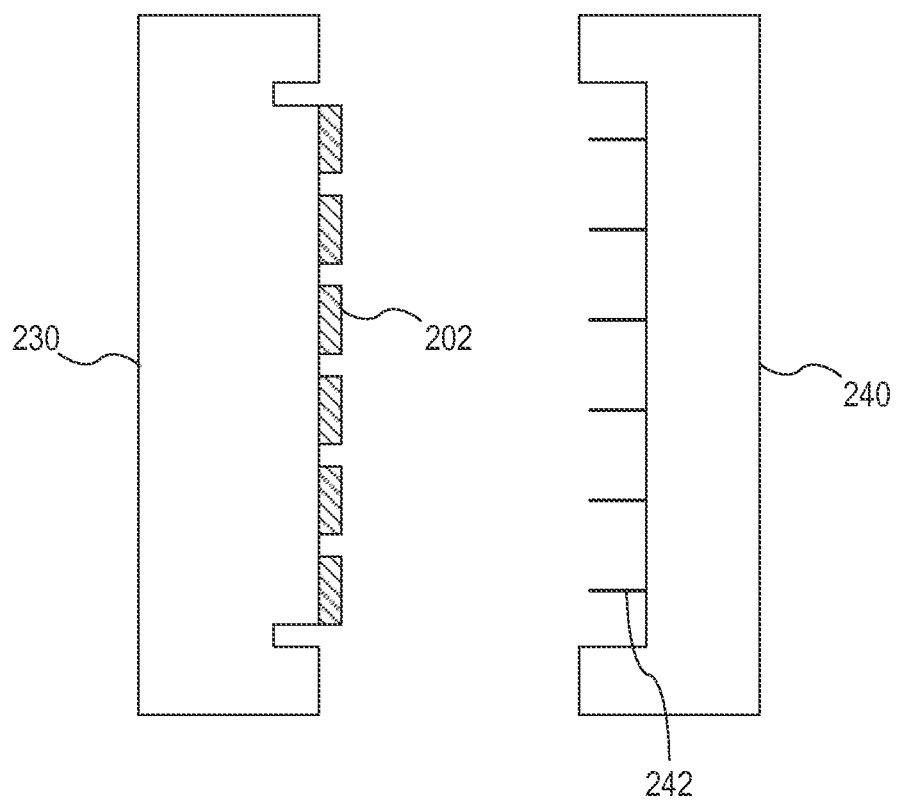
FIGS. 2E-2H are schematic diagrams illustrating selected steps for manufacturing an exemplary combination of a first structure and a second structure in accordance with some embodiments.

FIG. 2E illustrates that the first structure 202 is held in a first mold component 230 by vacuum suction. The vacuum suction pulls the first structure 202 toward the first mold component 230 so that the first structure 202 remains flat through the molding process. Typically, the vacuum suction is applied over a plurality of locations on the first structure 202. The vacuum suction typically leaves one or more indentations on the surface of the first structure 202 facing the first mold component 230. In some embodiments, the first mold component 230 includes a plurality of vacuum holes (not shown).

In some embodiments, a plurality of pins 242 coupled with the second mold component 240 are spring loaded so that the plurality of pins 242 are configured to apply force on the first structure 202 toward the first mold component 230 when the first mold component 230 and the second mold component 240 are assembled together.

In some embodiments, the bottom surface of the first structure 202 (e.g., the surface facing the second mold component 240) is treated, typically before the first structure 202 is held in the first mold component 230, to facilitate coupling with the second structure 204. In some embodiments, the bottom surface of the first structure 202 is treated to reduce the hydrophobicity (e.g., increase the surface tension) of the first structure 202. In some embodiments, the bottom surface of the first structure 202 is roughened to increate the contact area with the second structure 204.

In some embodiments, the first mold component 230 has a flat surface or a portion of the surface that is flat facing the first structure 202. In some embodiments, the portion of the surface has rough structure, for example of columnar pillars of 10 nm-100 um width and 10 nm-100 um height. The rough structure is transferred to the surface of the first structure 202 in contact during the molding process.

In some embodiments, the surface of the first mold component 230 has protrusions and/or indentations, the impact of which is described below with respect to FIGS. 5A-5C below.

Figure 2F:
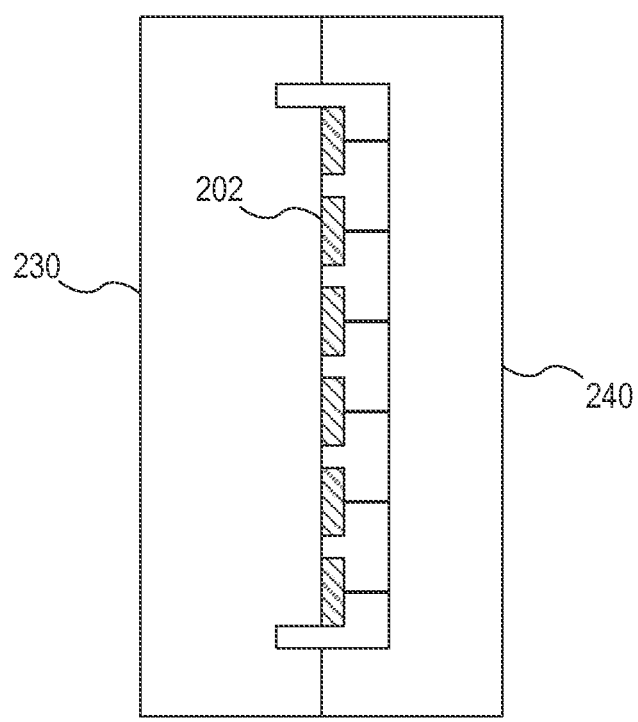

FIG. 2F illustrates that the first mold component 230 and the second mold component 240 are assembled, thereby forming a cavity inside, into which a heated plastic material is introduced for a molding process.

Figure 2G:
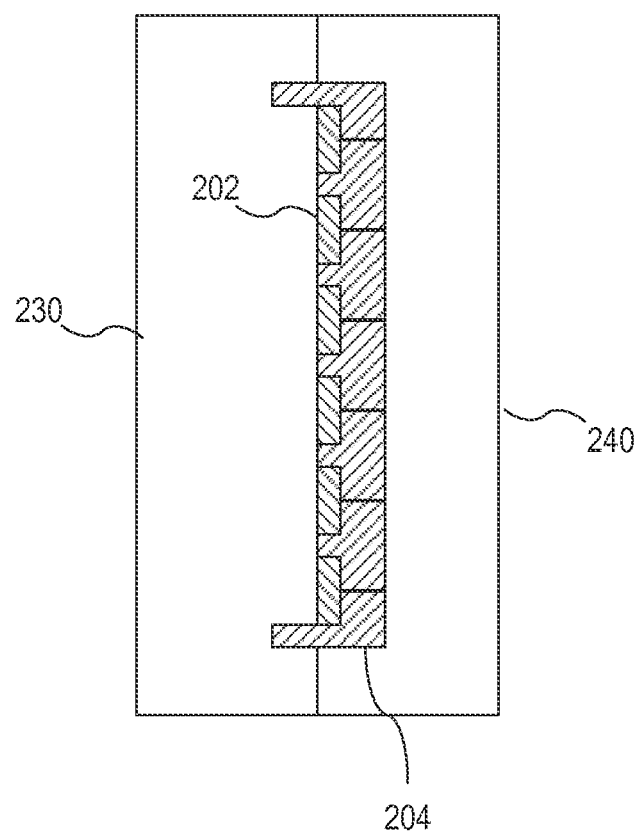

FIG. 2G illustrates that a heated plastic material is introduced into the cavity. In some embodiments, the plastic material includes polycarbonates. In some embodiments, the plastic material includes polystyrene. In some embodiments, the plastic material includes cyclic olefin polymer or copolymer.

Once the heated plastic material is cooled, the plastic material forms the second structure 204. When the second structure 204 is formed, the second structure 204 is coupled with the first structure 202 so as to form the combination 220 of the first structure 202 and the second structure 204.

In some embodiments, the first mold component 230 has a portion of the surface that is flat facing the first structure 202, and in contact with the second structure 204. In some embodiments, the portion of the surface has rough structure, for example of columnar pillars of 10 nm-100 um width and 10 nm-100 um height. The rough structure is transferred to the surface of the second structure 204 in contact during the molding process.

Figure 2H:
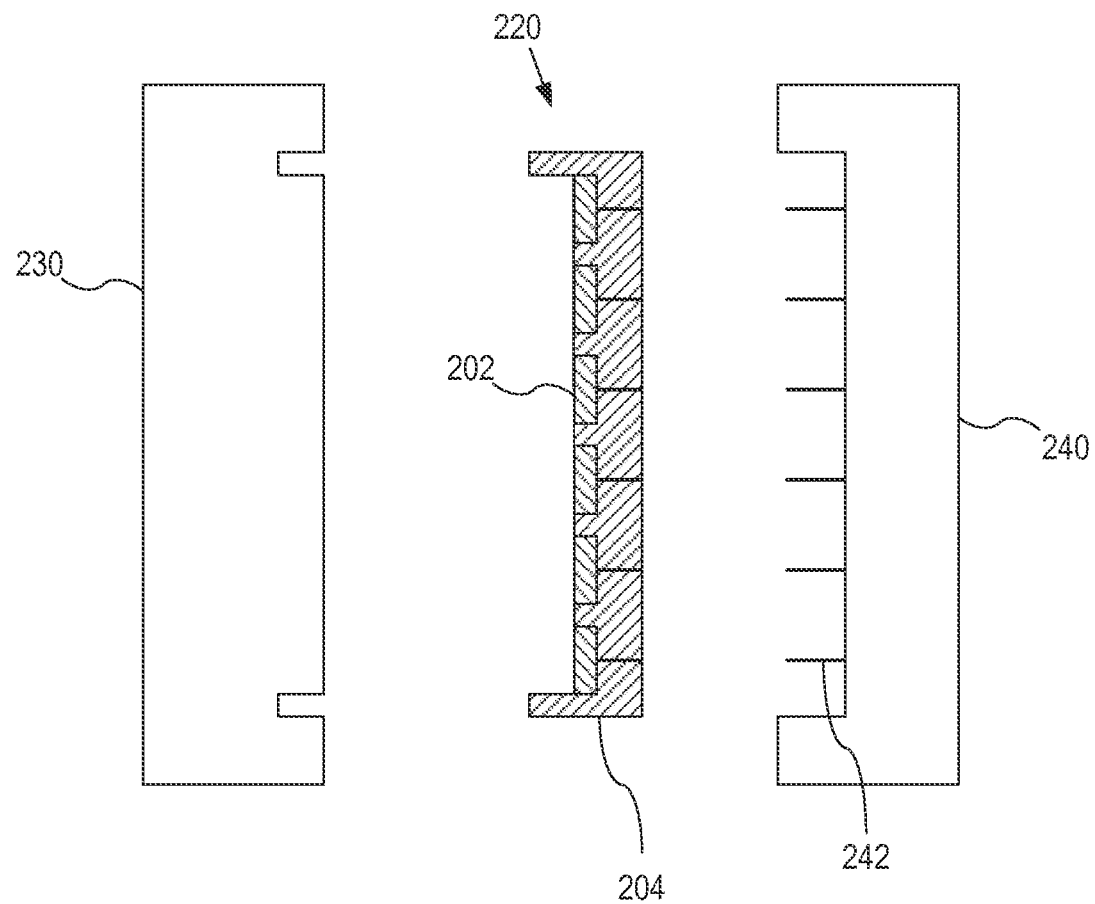

FIG. 2H illustrates that the combination 220 is removed from the first mold component 230 and the second mold component 240.

Note that the combination 220 removed from the first mold component 230 and the second mold component 240 has pin marks corresponding to the plurality of pins 242 coupled with the second mold component 240. When optical measurements (e.g., collection of optical images or optical signals) are performed through respective portions of the second structure 204 corresponding to the plurality of discrete through holes defined in the first structure 202, if the pin marks are located at the respective portions of the second structure 204 corresponding to the plurality of discrete through holes defined in the first structure 202, the pin marks interfere optical measurements. Thus, to avoid the interference by the pin marks, the plurality of pins 242 are located offset from the plurality of discrete through holes defined in the first structure 202. Alternatively, the first structure 202 and the second structure 204 are aligned so that the plurality of discrete through holes defined in the sheet layer of the first structure 202 is offset from the plurality of holding locations in the second structure 204.

Although FIGS. 2E-2H illustrate forming the combination 220 of the first structure 202 and the second structure 204 by a molding process, the combination 220 of the first structure 202 and the second structure 204 may be manufactured by attaching the first structure 202 to a preformed second structure 204.

FIG. 3A is an exploded view of an exemplary array plate 320 in accordance with some embodiments. The exemplary array plate 320 includes a third structure 310 and the combination 220 of the first structure 202 and the second structure 204 described above with respect to FIGS. 2E-2H.

In some embodiments, the third structure 310 includes a plurality of vertical indentations 314 along the outside of the third structure 310. In some embodiments, a respective side of the third structure 310 defines a longitudinal axis, and respective vertical indentations 314 located on the respective side of the third structure 310 are substantially perpendicular to the longitudinal axis formed by the respective side of the third structure 310 (e.g., a respective vertical indentation 314 forms 60-120° with the longitudinal axis of the respective portion of the third structure 310). In some embodiments, the vertical indentations 314 are substantially perpendicular to the plane defined by the base layer 208 of the second structure 202 of the combination 220 (e.g., a respective vertical indentation 314 forms 45° or less with a surface normal of the base layer 208 of the second structure 202 of the combination 220). In some embodiments, the plurality of vertical indentations 314 reduces distortion of the third structure 310, thereby maintaining a flatness of the top surface of the third structure 310.

In some embodiments, the third structure 310 includes one or more handles 312, each handle 312 including a plurality of fins.

Figure 3D:
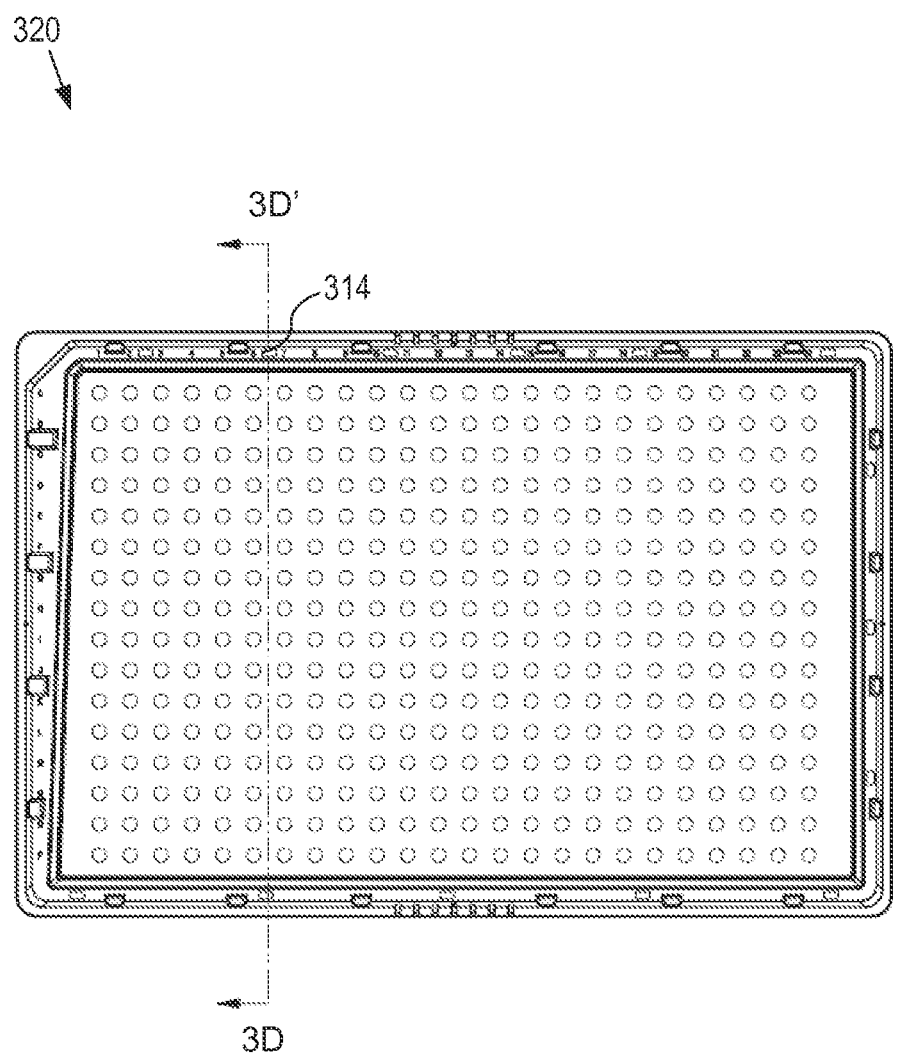
Figure 3E:
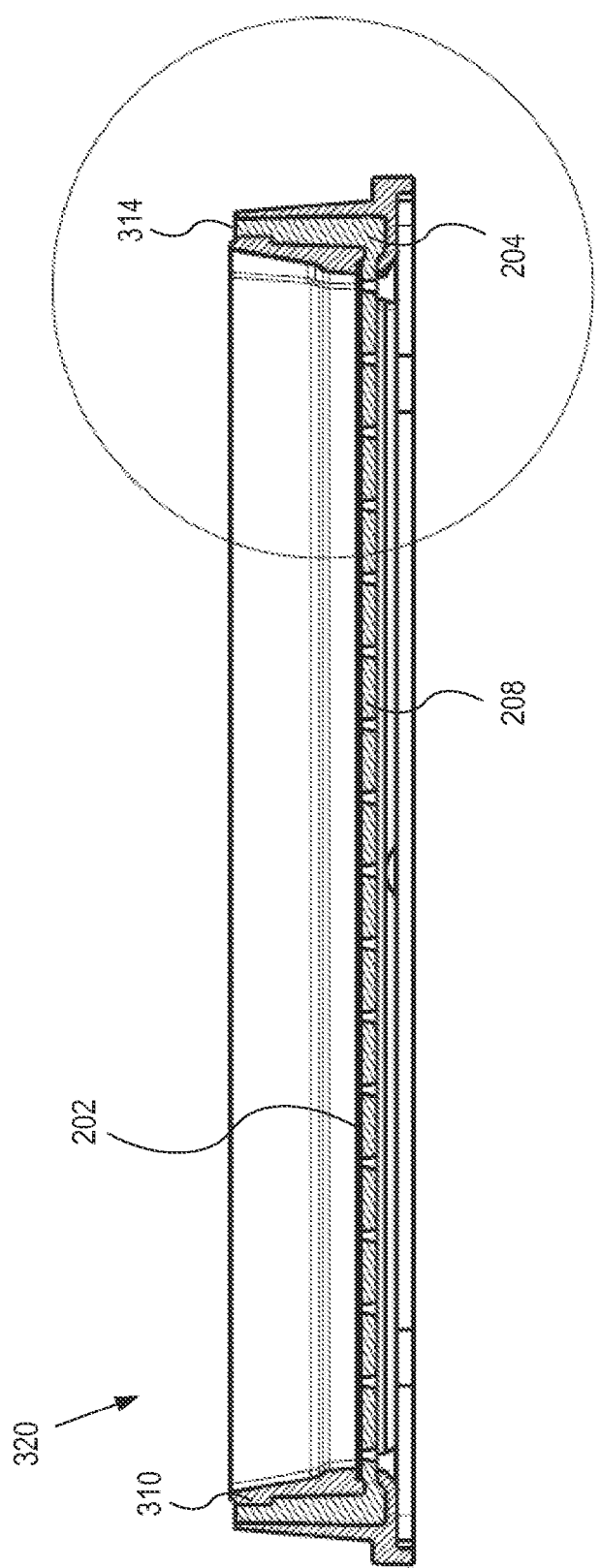
FIG. 3E is a cross-sectional view of the exemplary array plate corresponding to a section indicated in FIG. 3D in accordance with some embodiments.
Figures 1, 3E:
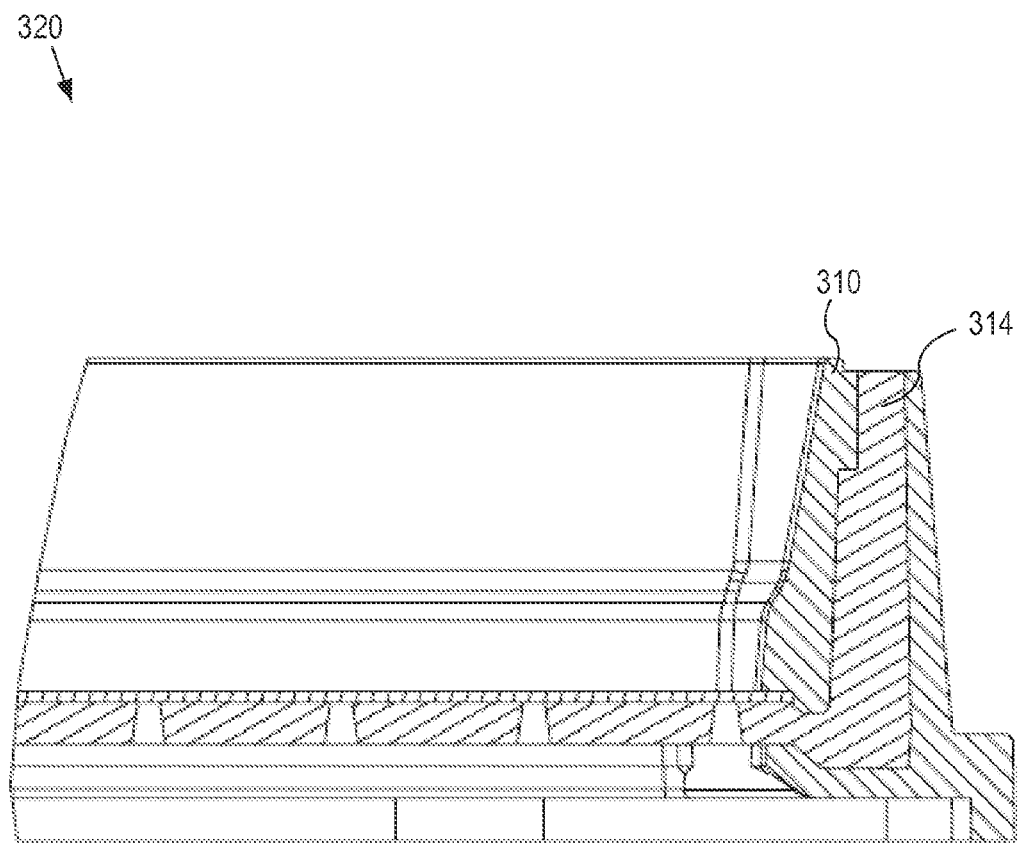
Figure 3F:
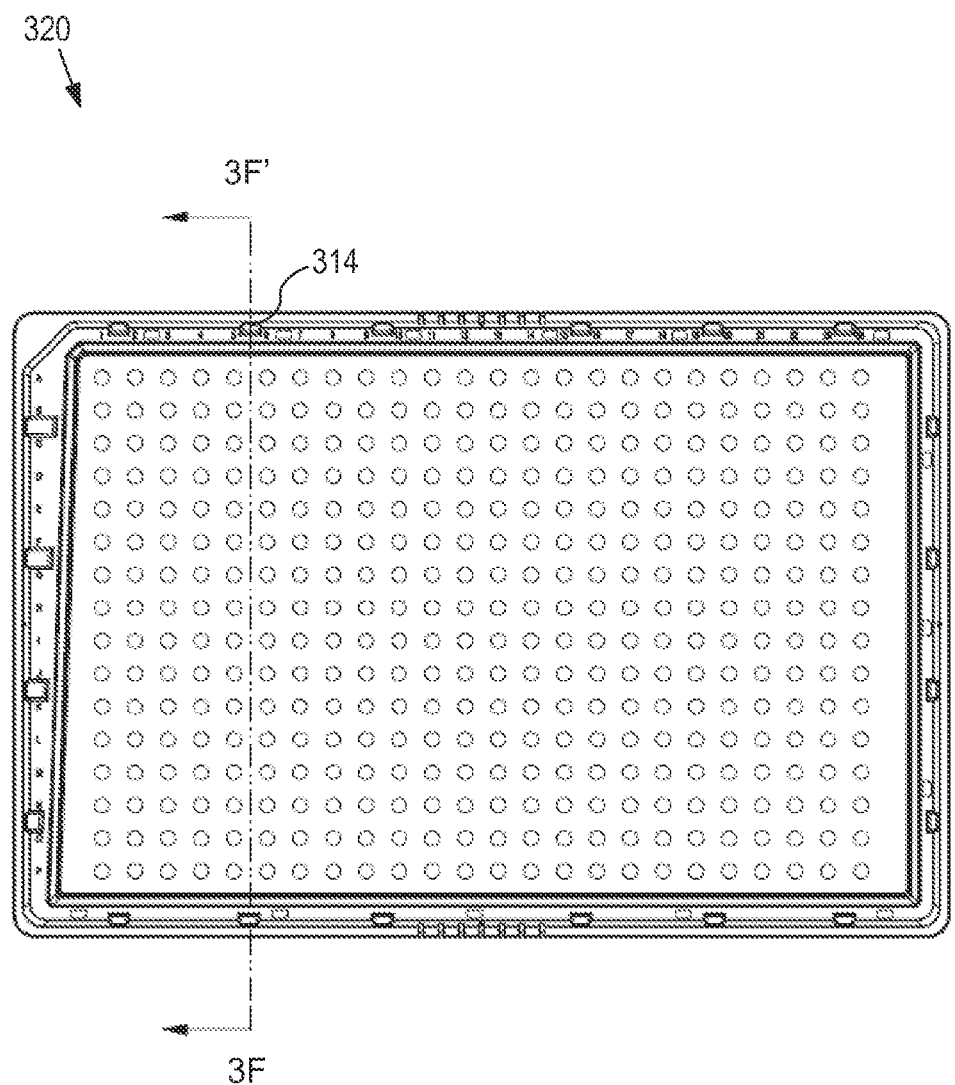

FIGS. 3B, 3D, and 3F are top perspective views of an exemplary array plate in accordance with some embodiments.

FIG. 3B also indicates a line 3B-3B' across the array plate 320. The line 3B-3B' traverses a plurality of the discrete through holes in the sheet layer of the first structure 202. The line 3B-3B' corresponds to the cross-sectional view illustrated in FIG. 3C.

FIG. 3C is a cross-sectional view of the exemplary array plate 320 corresponding to a section indicated in FIG. 3B in accordance with some embodiments. FIG. 3C-1 is a partial sectional view of a side wall region of the exemplary array plate 320 illustrated in FIG. 3C. FIGS. 3C and 3C-1 show that, in some embodiments, at least a portion of the first structure 202 is covered by the third structure 310 so that the first structure 202 is securely coupled, and any leak or retention of a liquid solution along the line between the first structure 202 and the third structure 310.

FIG. 3D also indicates a line 3D-3D' across the array plate 320. The line 3D-3D' corresponds to the cross-sectional view illustrated in FIG. 3E. The line 3D-3D' traverses the pins 314 in the vertical structures of the second structure 204. The line 3D-3D' corresponds to the cross-sectional view illustrated in FIG. 3E.

FIG. 3E is a cross-sectional view of the exemplary array plate 320 corresponding to a section indicated in FIG. 3D in accordance with some embodiments. FIG. 3E-1 is a partial sectional view of a side wall region (corresponding a circle illustrated in FIG. 3E) of the exemplary array plate 320 illustrated in FIG. 3E. As illustrated in FIG. 3E, in some embodiments, the pin 314 extends through the third structure 310 so that a top of the pin 314 is exposed.

FIG. 3F also indicates a line 3F-3F' across the array plate 320. The line 3F-3F' corresponds to the cross-sectional view illustrated in FIG. 3E. The line 3F-3F' traverses vertical indentations 314 on the side walls. The line 3F-3F' corresponds to the cross-sectional view illustrated in FIG. 3G.

Figure 3G:
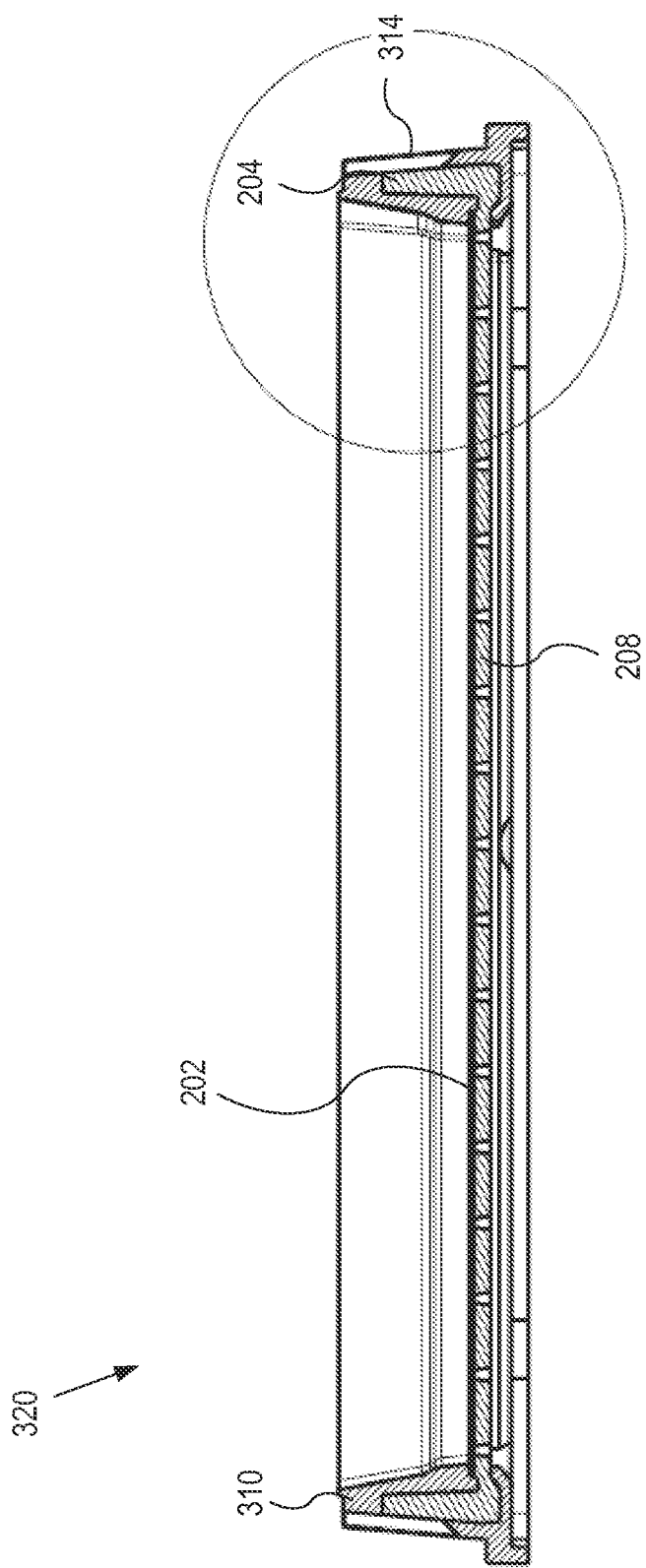
FIG. 3G is a cross-sectional view of the exemplary array plate corresponding to a section indicated in FIG. 3F in accordance with some embodiments.
Figures 1, 3G:
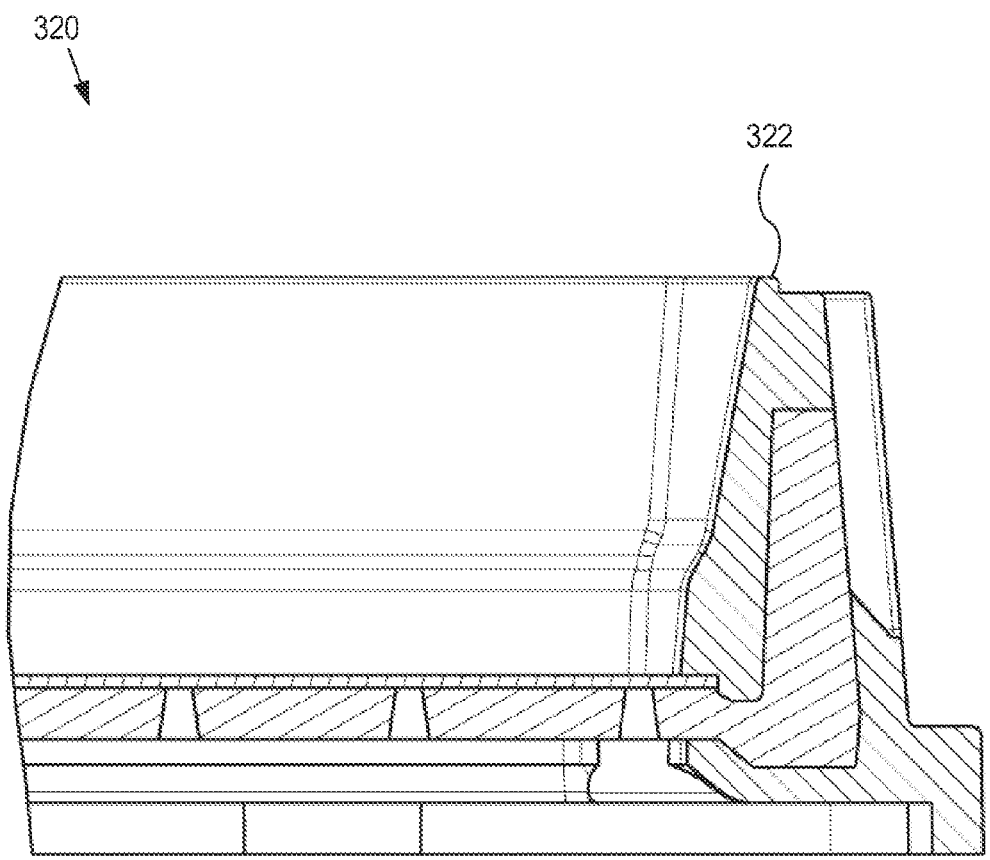

FIG. 3G is a cross-sectional view of the exemplary array plate corresponding to a section indicated in FIG. 3F in accordance with some embodiments. FIG. 3G-1 is a partial sectional view of a side wall region (corresponding to a circle illustrated in FIG. 3G) of the exemplary array plate 320 illustrated in FIG. 3G. In some embodiments, the one or more side walls each have an inner surface, an outer surface, a bottom adjacent to the sheet layer of the first structure 202, and a top surface opposite the bottom, and a respective side wall of the one or more side walls includes one or more lips 322 on the top surface, at least one of the one or more lips aligned with the inner surface of the respective side wall.

Figure 3H:
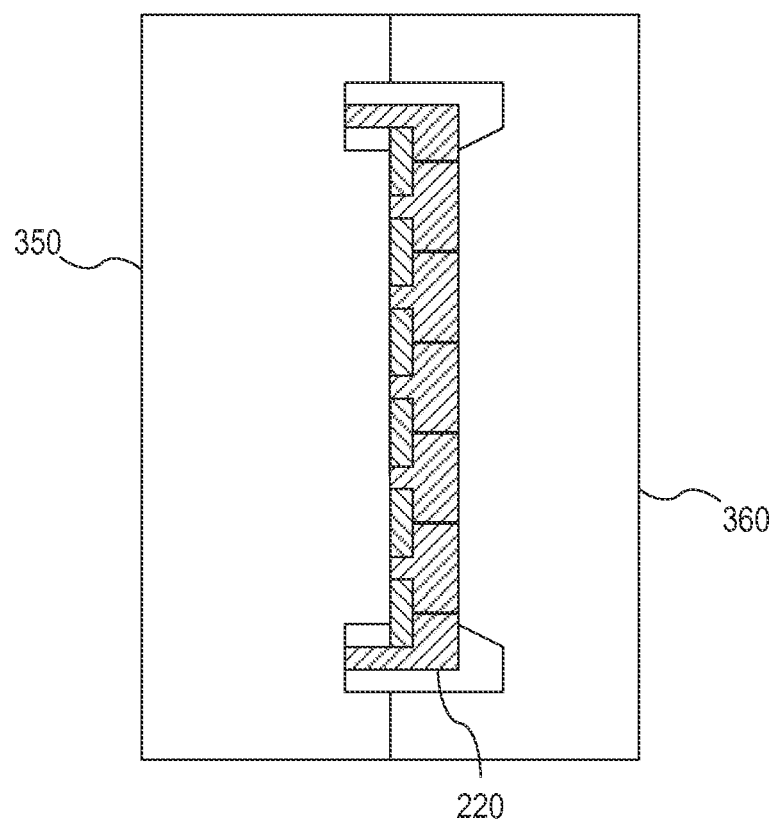
FIGS. 3H-3J are schematic diagrams illustrating selected steps for manufacturing an exemplary array plate in accordance with some embodiments.
Figure 3I:
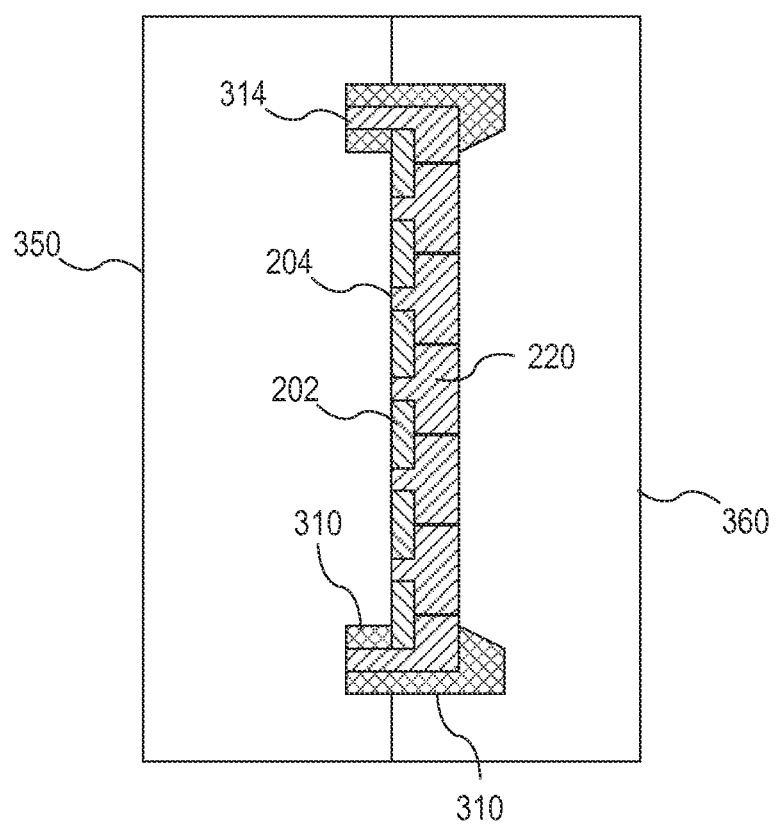
Figure 3J:
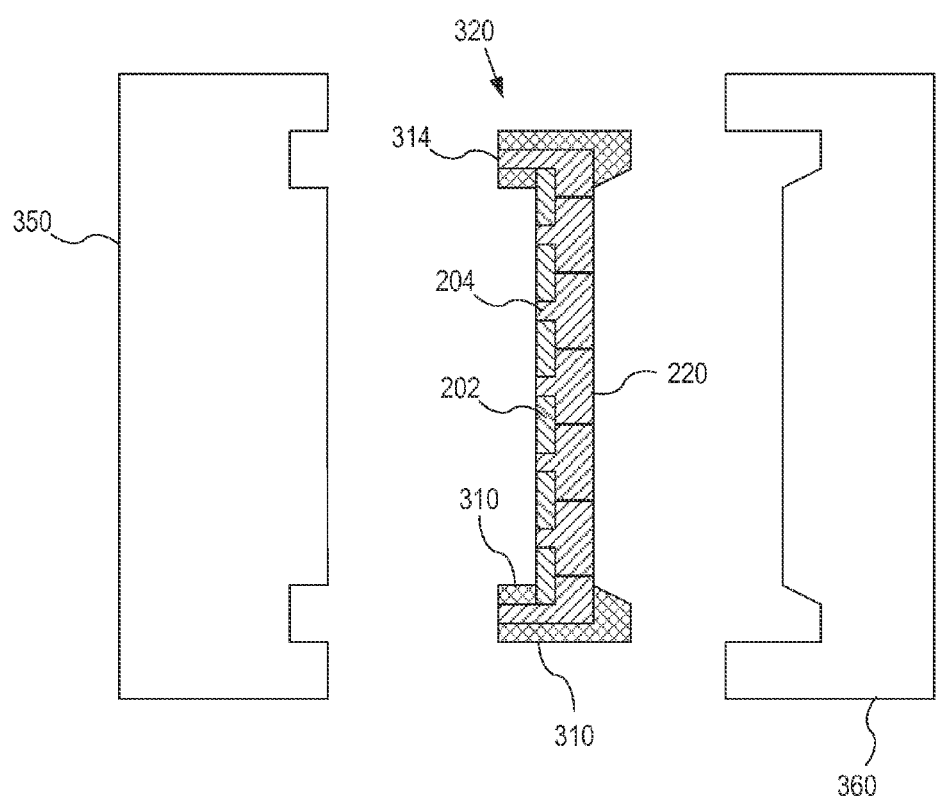

FIGS. 3H-3J are schematic diagrams illustrating selected steps for manufacturing an exemplary array plate with a second molding process in accordance with some embodiments. The elements in FIGS. 3H-3J are not drawn to scale.

FIG. 3H illustrates that the combination 220 of the first structure 202 and the second structure 204 is located in a cavity formed by a third mold component 350 and a fourth mold component 360.

FIG. 3I illustrates that the cavity formed by the third mold component 350 and the fourth mold component 360 is filled with a heated second plastic material. In some embodiments, the second plastic material is distinct from the plastic material used to form the second structure. In some embodiments, the second plastic material is identical to the plastic material used to form the second structure. In some embodiments, the second plastic material has a glass transition temperature lower than the glass transition temperature of the plastic material used for the second structure 204. This reduces the glass transition of the plastic material in the second structure 204 during the second molding process so that the second structure 204 maintains its shape and flatness during the second molding process. Exemplary glass transition temperatures are ~95° C. for polystyrene, ~130° C. for polyfluorotetraethylene, and 145-150° C. for polycarbonates. The glass transition temperature of cyclic olefin copolymer may exceed 150° C. In some embodiments, the melting temperature for the second plastic material is typically not higher than 200° C.

Once the second plastic material is cooled, the third structure 310 is formed. The third structure 310 is coupled with the combination 220 of the first structure 202 and the second structure 204. In some embodiments, the third structure 310 covers at least the one or more vertical structures of the second structure 204. In some embodiments, the third structure 310, when included, covers at least a portion of an inner surface of respective vertical structures 204, thereby forming one or more side walls. In other words, in such embodiments, the reservoir of the array plate 320 is defined by the third structure 310 on the sides, and the first structure 202 and the second structure 204 on the bottom. In some embodiments, a respective side wall of the one or more side walls has 1-8 mm, 2-5 mm, 2-4 mm, 2-3 mm, or 3-4 mm width. In some embodiments, a respective side wall of the one or more side walls has 1-10 mm, 2-9 mm, 3-8 mm, 4-7 mm, or 5-6 mm height.

In some embodiments, the one or more side walls each have an inner surface, an outer surface, a bottom adjacent to the sheet layer of the first structure 202, and a top surface opposite the bottom, and a respective side wall of the one or more side walls includes one or more vertical indentations 314 (FIG. 3G) along the outer surface of the respective side wall.

In some embodiments, the one or more side walls are made of a hydrophobic material of a surface tension lower than 35 dynes/cm (e.g., hydrocarbon polymer, polypropylene, polytetrafluoroethylene, and their derivative, etc.). In some embodiments, the one or more side walls are made of a hydrophobic material of a surface tension lower than 25 dynes/cm.

In some embodiments, the one or more side walls each have an inner surface, an outer surface, a bottom adjacent to the sheet layer of the first structure, and a top surface opposite the bottom, and the inner surface of a respective side wall of the one or more side walls is coated to expose a hydrophobic surface of a surface tension lower than 35 dynes/cm.

FIG. 3J illustrates that the array plate 320 is released from the third mold component 350 and the fourth mold component 360. In some embodiments, releasing the array plate 320 from the third mold component 350 includes pushing the plurality of pins 214 of the second structure 204. In some embodiments, the second structure 204 and the plurality of pins 214 of the second structure 204 are made of a stiffer material (e.g., a material with a higher elastic modulus, such as a spring constant, Young's modulus, etc.) than the third structure 310.

Although FIGS. 3H-3J illustrate forming the array plate 320 by a molding process, the array plate 320 may be manufactured by interposing the combination 220 of the first structure 202 and the second structure 204 between a top layer and a bottom layer, both of which are prefabricated, and attaching the top layer and the bottom layer to each other and/or to the combination 220 of the first structure 202 and the second structure 204.

Although FIGS. 2E-2H and FIGS. 3H-3J illustrate manufacturing an exemplary array plate using two-step molding processes, it is also possible to make an array plate with a single molding process.

In some embodiments, the one or more vertical structures formed during the first molding process may be configured to form one or more side walls, thereby eliminating the need for a second molding process to form one or more side walls over the one or more vertical structures.

Alternatively, in some embodiments, the first structure 202 includes one or more vertical structures (e.g., the first structure 202 includes a tray that has the sheet layer and one or more vertical structures, such as short walls, along the periphery of the sheet layer). In such embodiments, the molding step to form the vertical structures is skipped. In a molding step for forming one or more side walls, the first structure 202 is placed inside a mold, and a heated plastic is introduced to form one or more side walls over the one or more vertical structures of the first structure.

Figure 4A:
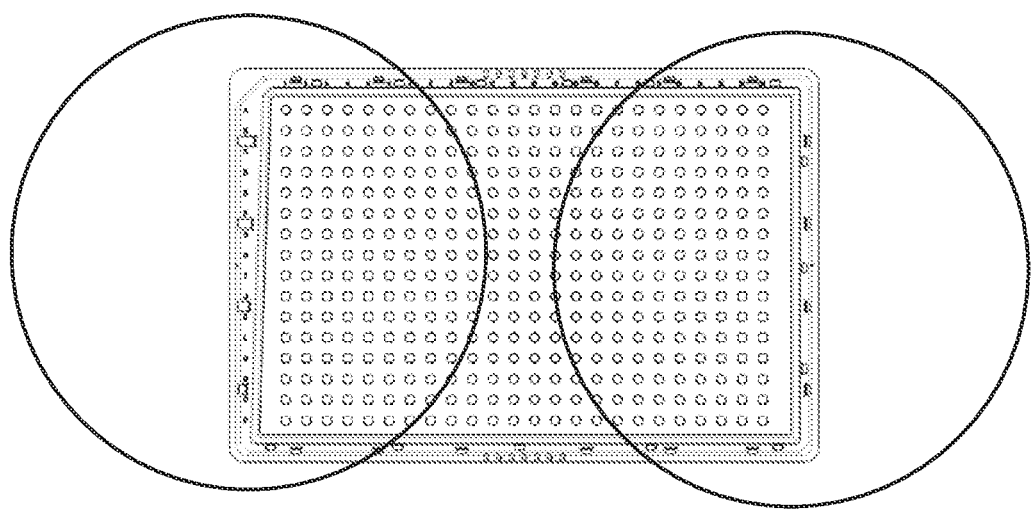
FIG. 4A is a top perspective view of an exemplary array plate in accordance with some embodiments.
Figure 4B:
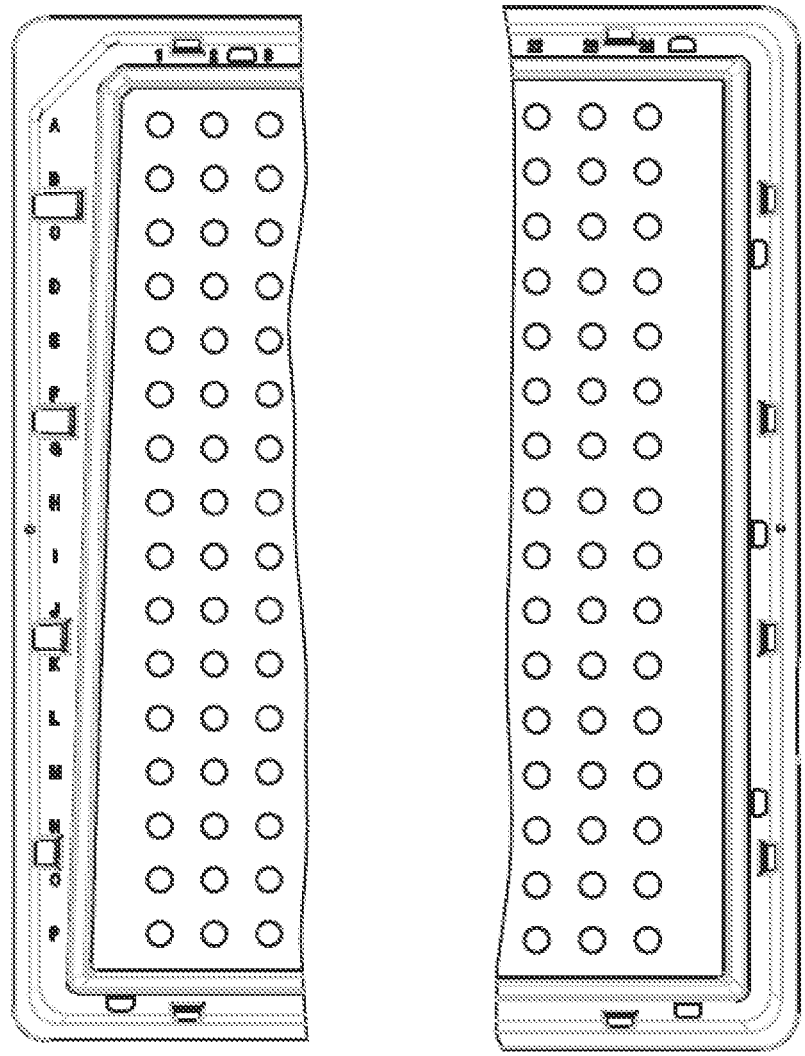
FIG. 4B are partial top views of an exemplary array plate in accordance with some embodiments.

FIG. 4A is a top perspective view of an exemplary array plate in accordance with some embodiments. FIG. 4B illustrates partial top views of an exemplary array plate, corresponding to regions indicated with circles in FIG. 4A, in accordance with some embodiments.

When the inner side walls and the base layer form sharp corners (e.g., the inner side walls and the base layer form 90 degree angle), the sharp corners hold more residual wash solution due to increased surface interaction, i.e. adhesion between the plastic surface and the solution. Therefore, in some embodiments, the contact lines between the inner side walls and the base layer of the second structure have a curved transition (e.g., rounded) as shown in FIG. 4. The rounded four corners of the circumferential wall reduce residual solution after a washing process.

FIGS. 4A-4B illustrate that, in some embodiments, at least one side wall is tilted outward an angle of 2-20 degrees so that the top of the side wall (e.g., the end of the side wall that is away from the base layer) is positioned outside the bottom of the side wall (e.g., the end of the side wall that is closer to the base layer). In some embodiments, all side walls are tilted by between 2-5 degrees.

Figure 5A:
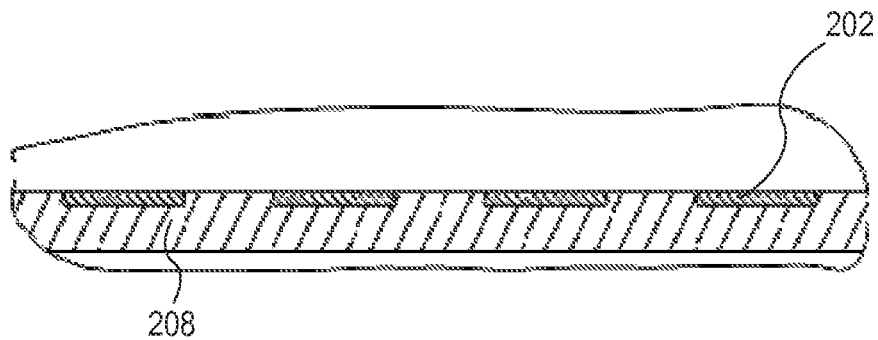
FIGS. 5A-5C are partial sectional views of exemplary array plates in accordance with various embodiments.
Figure 5B:
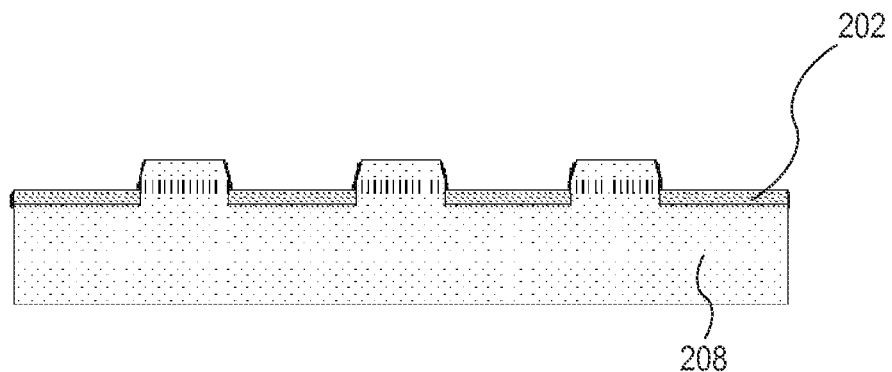
Figure 5C:
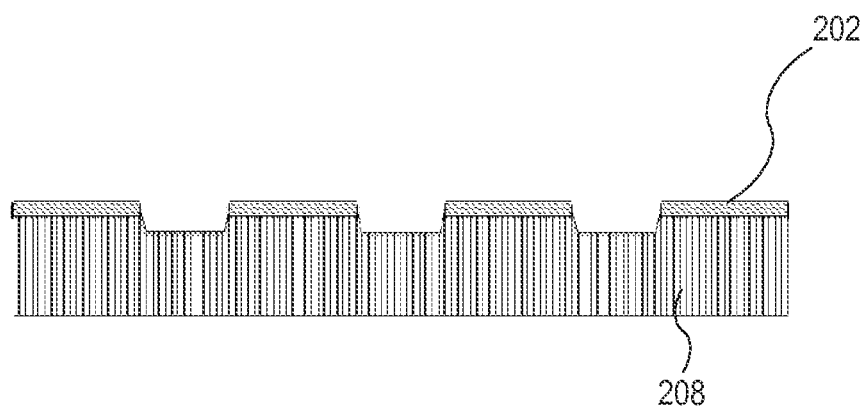
Figure 6A:
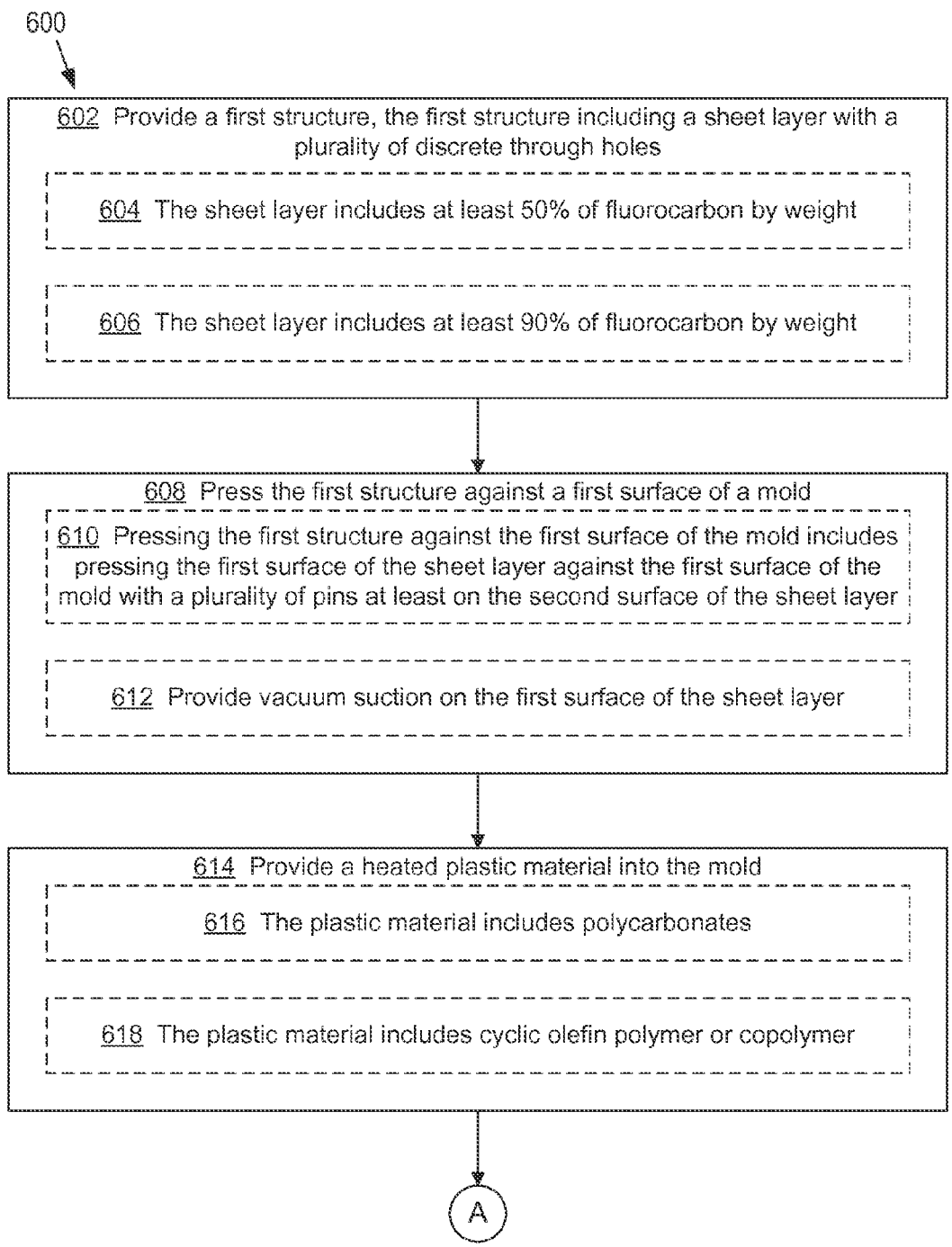

FIGS. 5A-5C are partial sectional views of exemplary array plates in accordance with various embodiments.

FIG. 5A illustrates that, in some embodiments, a top surface of the sheet layer of the first structure 202 is aligned with a top surface of the base layer 208 of the second structure 204. In some embodiments, the alignment of the top surface of the sheet layer of the first structure 202 and the top surface of the base layer 208 of the second structure 204 is achieved by using a mold component (e.g., the first mold component 230, FIG. 2E) that has a flat surface at least over a portion of the surface facing the top surface of the first structure 202. As shown in FIG. 2G, the heated plastic material fills up the plurality of discrete through holes defined in the first structure 202 up to the surface of the mold component 230 that faces the first structure 202, which is aligned with the top surface of the first structure 202.

In some embodiments, a mold surface that has indentations and/or protrusions is used. When the mold surface facing the top surface of the first structure 202 has indentations at locations corresponding to the plurality of discrete through holes defined in the first structure 202, the heated plastic material, when introduced into the cavity formed by mold components, fills the indentations. As a result, the top surface of the second structure is located above the top surface of the first structure as shown in FIG. 5B. Alternatively, when the mold surface facing the top surface of the first structure 202 has protrusions at locations corresponding to the plurality of discrete through holes defined in the first structure 202, the heated plastic material, when introduced into the cavity formed by mold components, underfills the discrete through holes defined in the first structure 202. As a result, the top surface of the second structure is located below the top surface of the first structure as shown in FIG. 5C. In some embodiments, the top surface of the second structure includes a plurality of concave surfaces. In some embodiments, a mold surface that has both indentations and protrusions is used. When the mold surface facing the top surface of the first structure 202 has indentations and protrusions at locations corresponding to the plurality of discrete through holes defined in the first structure 202, complex structures can be formed at the locations corresponding to the plurality of discrete through holes defined in the first structure 202.

FIGS. 6A-6D are flow charts representing a method 600 of making an array plate in accordance with some embodiments.

The method includes (602) providing a first structure. The first structure includes a sheet layer with a plurality of discrete through holes.

In some embodiments, the sheet layer includes (604) at least 50% of fluorocarbon by weight.

In some embodiments, the sheet layer includes (606) at least 90% of fluorocarbon by weight.

The method includes placing the first structure adjacent to a first surface of a mold. In some embodiments, the method includes (608) pressing the first structure against the first surface of the mold.

In some embodiments, includes placing the first structure adjacent to the first surface of the mold includes placing the first structure adjacent to the first surface of the mold with a plurality of pins. In some embodiments, pressing the first structure against the first surface of the mold includes pressing the first surface of the sheet layer against the first surface of the mold with a plurality of pins. In some embodiments, pressing the first structure against the first surface of the mold includes (610) pressing the first surface of the sheet layer against the first surface of the mold with a plurality of pins at least on the second surface of the sheet layer.

In some embodiments, the method includes (612) providing vacuum suction on the first surface of the sheet layer.

The method includes (614) providing a heated plastic material into the mold.

In some embodiments, the plastic material includes (616) polycarbonates. In some embodiments, the plastic material includes polystyrene.

In some embodiments, the plastic material includes (618) cyclic olefin polymer or copolymer.

The method includes cooling the plastic material to form a second structure. In some embodiments, the method includes (620, FIG. 6B) cooling the plastic material to form a second structure so that the first structure and the second structure are coupled. The second structure includes a base layer. In some embodiments, the second structure includes a base layer and one or more vertical structures along a periphery of the base layer, adjacent to a first surface of the base layer. At least a portion of a first surface of the sheet layer of the first structure is exposed from the second structure, and a second surface of the sheet layer, opposite to the first surface of the sheet layer, is embedded in the base layer of the second structure adjacent to the first surface of the base layer.

In some embodiments, the plastic material of the second structure is (622) optically transparent.

In some embodiments, the method includes (624) coupling a third structure with at least the second structure over at least a portion of the one or more vertical structures, the third structure including one or more side walls.

In some embodiments, the one or more vertical structures of the second structure include (626) a plurality of pins vertically protruding from the rest of the one or more vertical structures.

In some embodiments, the method includes (628) molding the third structure over at least a portion of the one or more vertical structures with a second mold so as to couple the second structure and the third structure, and removing a combination of the second structure and the third structure from the second mold by pushing respective locations on the third structure that correspond to the plurality of pins of the second structure.

In some embodiments, the one or more side walls are (630) made of a plastic material that has a glass transition temperature lower than the glass transition temperature of (the material for) the second structure.

In some embodiments, the one or more vertical structures include (632) one or more side walls.

In some embodiments, the one or more side walls are (634, FIG. 6C) made of a material that has Shore A hardness of 85 or less.

In some embodiments, the one or more side walls each have (636) an inner surface, an outer surface, a bottom adjacent to the sheet layer of the first structure, and a top surface opposite the bottom, and a respective side wall of the one or more side walls includes one or more lips on the top surface, at least one of the one or more lips aligned with the inner surface of the respective side wall.

In some embodiments, the one or more side walls each have (638) an inner surface, an outer surface, a bottom adjacent to the sheet layer of the first structure, and a top surface opposite the bottom, and a respective side wall of the one or more side walls includes one or more vertical indentations along the outer surface of the respective side wall.

In some embodiments, the one or more side walls are (640) made of a hydrophobic material of a surface tension lower than 35 dynes/cm.

In some embodiments, the one or more side walls each have (642) an inner surface, an outer surface, a bottom adjacent to the sheet layer of the first structure, and a top surface opposite the bottom, and the inner surface of a respective side wall of the one or more side walls is coated to expose a hydrophobic surface of a surface tension lower than 35 dynes/cm.

In some embodiments, the second structure includes (644) a plurality of holding locations, the method comprising aligning the first structure and the second structure so that the plurality of discrete through holes defined in the sheet layer of the first structure is offset from the plurality of holding locations in the second structure.

In some embodiments, the mold is configured (646, FIG. 6D) so that a top surface of the sheet layer of the first structure is aligned with a top surface of the base layer of the second structure.

In some embodiments, the mold is configured (648) so that a top surface of the sheet layer of the first structure is above a top surface of the base layer of the second structure.

In some embodiments, the mold is configured (650) so that a top surface of the sheet layer of the first structure is below a top surface of the base layer of the second structure.

In some embodiments, the first surface of the mold has (652) one or more of: a plurality of indentations and a plurality of protrusions corresponding to the plurality of discrete through holes defined in the sheet layer.

In some embodiments, at least one of the side walls includes (654) one or more handles, each handle comprising a plurality of parallel fins.

Many modifications and variations are possible in view of the above teachings. For example, in accordance with some embodiments, a method for making an array plate includes providing a first structure. The first structure including a sheet layer with a plurality of discrete through holes. The method includes pressing the first structure against a first surface of a mold, and providing a heated plastic material into the mold. The method includes cooling the plastic material to form a second structure so that the first structure and the second structure are coupled. The second structure includes a base layer and one or more side walls along a periphery of the base layer, adjacent to a first surface of the base layer. At least a portion of a first surface of the sheet layer of the first structure is exposed from the third structure, and a second surface of the sheet layer, opposite to the first surface of the sheet layer, is embedded in the base layer of the second structure adjacent to the first surface of the base layer.

In some embodiments, an array plate includes a first structure. The first structure including a sheet layer with a plurality of discrete through holes. The array plate also includes a second structure coupled to the first structure. The second structure including a base layer and one or more side walls along a periphery of the base layer, adjacent to a first surface of the base layer. At least a portion of a first surface of the sheet layer of the first structure is exposed from the second structure, and a second surface of the sheet layer, opposite to the first surface of the sheet layer, is embedded in the base layer of the second structure adjacent to the first surface of the base layer.

In accordance with some embodiments, a method for making an array plate includes providing a first structure. The first structure includes a sheet layer with a plurality of discrete through holes. The first structure also includes one or more vertical structures along a periphery of the sheet layer. The method includes pressing the first structure against a first surface of a mold, and providing a heated plastic material into the mold. The method includes cooling the plastic material to form a second structure so that the first structure and the second structure are coupled. The second structure includes a base layer and one or more side walls formed over the one or more vertical structures. At least a portion of a first surface of the sheet layer of the first structure is exposed from the third structure, and a second surface of the sheet layer, opposite to the first surface of the sheet layer, is embedded in the base layer of the second structure adjacent to the first surface of the base layer.

In some embodiments, an array plate includes a first structure. The first structure including a sheet layer with a plurality of discrete through holes. The first structure also includes one or more vertical structures along a periphery of the sheet layer. The array plate also includes a second structure coupled to the first structure. The second structure including a base layer and one or more side walls formed over the one or more vertical structures. At least a portion of a first surface of the sheet layer of the first structure is exposed from the second structure, and a second surface of the sheet layer, opposite to the first surface of the sheet layer, is embedded in the base layer of the second structure adjacent to the first surface of the base layer.

Operations and characteristics described above with respect to the method 600 are also applicable to these methods and devices. For brevity, such operations and characteristics are not repeated herein.

Methods for Using the Array Plates

In some embodiments, a method for using an array plate includes providing the array plate, wherein the array plate defines a reservoir. The method includes storing a liquid medium in the reservoir of the device so that the first surface of the sheet layer is covered by the liquid medium, and dispensing respective liquid droplets on respective locations on the base layer. The respective locations correspond to locations of the plurality of discrete through holes defined in the sheet layer, and the respective liquid droplets are immiscible with the liquid medium.

In some embodiments, the method also includes adding one or more solutions to one or more liquid droplets of the respective liquid droplets.

In some embodiments, the method also includes performing an immunoassay by: immobilizing one of one or more antibodies and one or more antigens in one or more respective liquid droplets to the base layer, and adding one or more solutions to the one or more respective liquid droplets of the respective liquid droplets. At least one of the one or more solutions includes the other of the one or more antibodies and the one or more antigens. The method also includes detecting a binding of the at least one antigen with at least one antibody in the one or more respective liquid droplets.

In some embodiments, the method includes washing the respective liquid droplets on the device by: removing a portion of the liquid medium, adding a wash buffer to the reservoir, shaking the device so that the wash buffer and the respective liquid droplets are mixed, draining at least a portion of the wash buffer from the reservoir, and providing a liquid medium in the reservoir of the device so that the first surface of the sheet layer is covered by the liquid medium.

Array Slides

Figure 7:
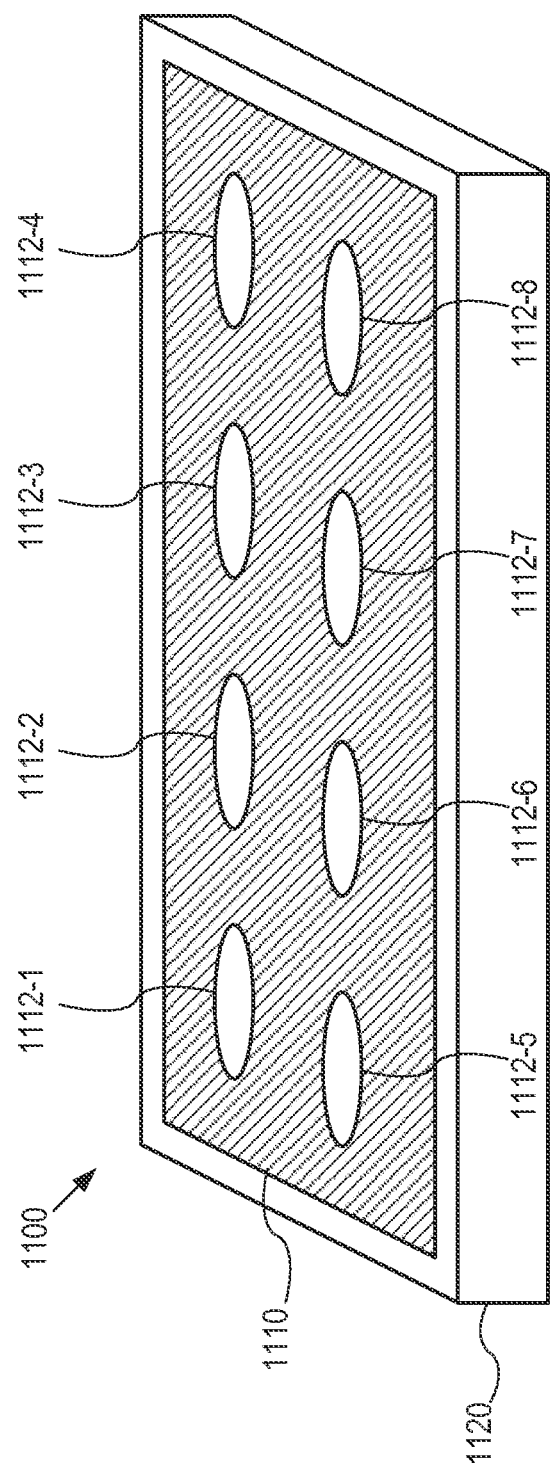
FIG. 7 is a perspective view of an exemplary array slide in accordance with some embodiments.

FIG. 7 is a perspective view of an exemplary array slide 1100 in accordance with some embodiments. The exemplary array slide 1100 includes at least a first structure 1110 (e.g., a sheet layer) and a second structure 1120 (e.g., a slide). The first structure 1110 includes fluorocarbon polymers. The first structure 1110 defines a plurality of discrete through holes (e.g., 1112-1 through 1112-8). The second structure 1120 includes a plastic material (e.g., polycarbonate, cyclic olefin polymer or copolymer, polystyrene, etc.). The first structure 1110 covers one or more portions of the second structure 1120. One or more portions of the second structure 1120 are not covered by the first structure 1110. Thus, one or more portions of the second structure 1120 are exposed through the plurality of discrete through holes 1112 defined by the first structure 1110. The details of the first structure and the second structure are described with respect to FIGS. 8A-8C, 10A-10C, and 11A-11B, below.

Figure 8A:
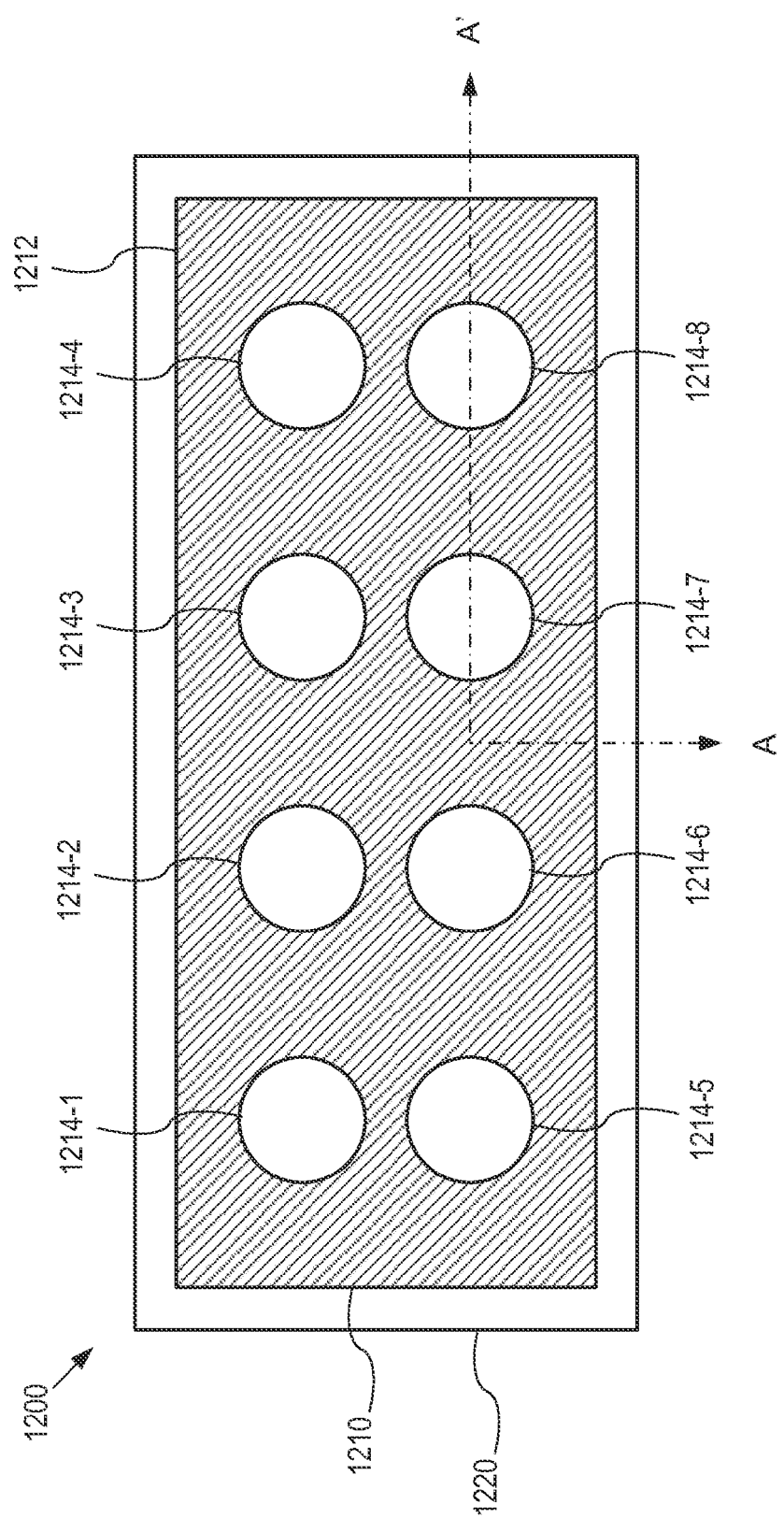
FIG. 8A is a top-down view of an exemplary array slide in accordance with some embodiments.

FIG. 8A is a top-down view of an exemplary array slide 1200 in accordance with some embodiments. The array slide 1200 includes a first structure 1210 and a second structure 1220. In some embodiments, the first structure 1210 has one or more characteristics of the first structure 1110 described above with respect to FIG. 7. In some embodiments, the second structure 1220 has one or more characteristics of the second structure 1120 described above with respect to FIG. 7. The descriptions of such characteristics are not repeated for brevity.

The first structure 1210 includes a sheet layer 1212 that typically has a square or rectangular shape (e.g., a sheet of PTFE cut into a rectangle). Alternatively, the sheet layer of the first structure 1210 may have a round shape, such as a disc, or any other shape (e.g., a generally rectangular shape with one or more chamfered corners).

The sheet layer 1212 defines a plurality of discrete through holes (e.g., 1214-1 through 1214-8). Typically, a discrete through hole 1214 has a round shape (e.g., a circle or an oval). Alternatively, the discrete through hole 1214 may have a non-round shape (e.g., a triangle, a square, a rectangle, a pentagon, a hexagon, an octagon, a star, a slit, etc.). In some embodiments, the plurality of discrete through holes 206 are formed by punching holes through the sheet layer 1212. Typically, the plurality of discrete through holes have substantially the same diameter (e.g., with less than 50, 30, 20, 10, or 5% variation among the holes). In some embodiments, a respective through hole has a 1 mm-5 mm diameter, or 2 mm-3 mm diameter. In some embodiments, the discrete through holes are arranged in a predefined pattern. For example, when 96 discrete through holes are defined in the sheet layer 1212, the 96 discrete through holes may be arranged in an 8×12 array. In another example, when 8 discrete through holes are arranged in the sheet layer 1212, the 8 discrete through holes may be arranged in a 2×4 array, as illustrated in FIG. 8A. In some embodiments, the discrete through holes have a predefined spacing.

The second structure 1220 typically has a rectangular shape. For example, the second structure 1220 may have a shape and size of a microscope slide. However, the second structure 1220 may have a larger or smaller size than a microscope slide. In some embodiments, the second structure 1220 has a square shape. In some embodiments, the second structure 1220 has a non-rectangular shape (e.g., a disc or a generally rectangular shape with one or more chamfered corners).

FIG. 8A also indicates a line A-A' across the array slide 1200. The line A-A' corresponds to the cross-sectional view illustrated in FIG. 8B.

Figure 8B:
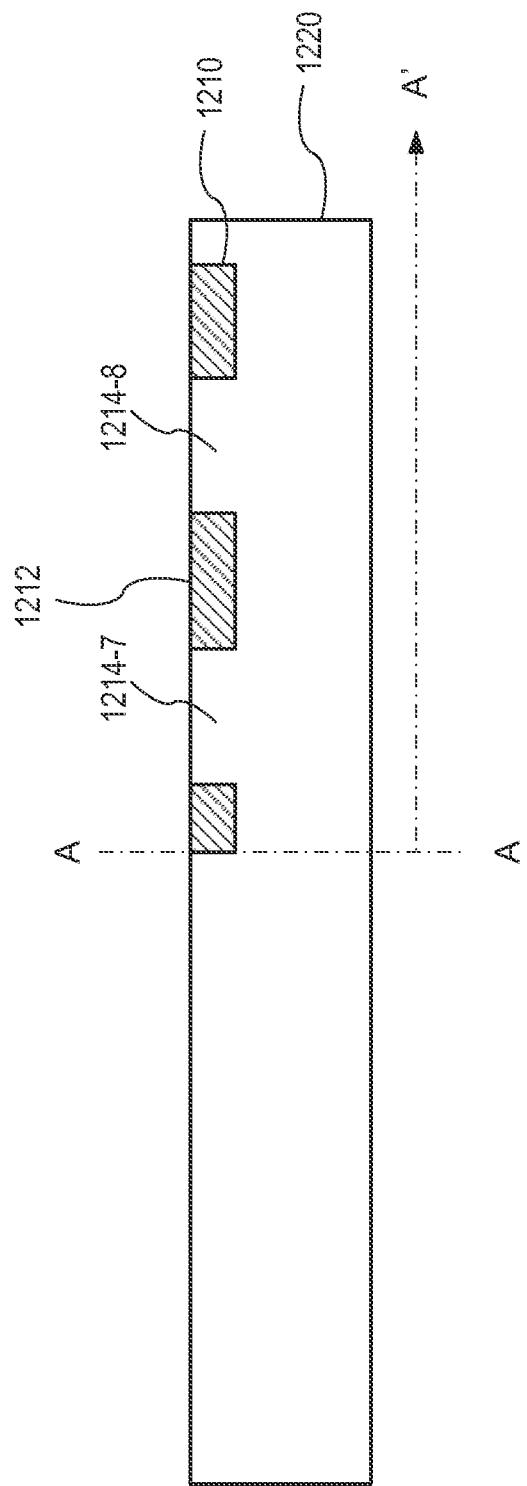
FIG. 8B is a partial cross-sectional view of an exemplary array slide in accordance with some embodiments.

FIG. 8B is a partial cross-sectional view of the exemplary array slide 1200 in accordance with some embodiments.

In some embodiments, the sheet layer 1212 solely constitutes the first structure 1210. In some other embodiments, the first structure 1210 includes additional features, such as one or more vertical structures (e.g., the first structure 1210 may be a tray including the sheet layer and one or more sidewalls) in addition to the sheet layer 1212.

In some embodiments, the sheet layer 1212 of the first structure 1210 has a uniform thickness across the sheet layer 1212. In some other embodiments, the sheet layer 1212 has a range of thicknesses across the sheet layer 1212. Typically, the thickness of the sheet layer 1212 is less than the width and length of the sheet layer 1212. In some embodiments, the thickness of the sheet layer 1212 is less than a predefined thickness. For example, the sheet layer has a thickness typically of 0.01-10 mm, 0.1-2 mm, 0.2-1 mm, or 1-2 mm.

In some embodiments, the sheet layer 1212 is a sheet of a preselected material. The preselected material typically includes a polymer (e.g., polytetrafluoroethylene, any other perfluorocarbon polymer, or any other fluorocarbon polymer). In some embodiments, the sheet layer 1212 includes a sheet of a preselected material. For example, the sheet layer 1212 may include multiple layers of different materials, wherein one of the multiple layers (e.g., typically a top layer) is a sheet of fluorocarbon (e.g., polytetrafluoroethylene). Alternatively, the sheet layer 1212 may include a core (e.g., a sheet metal) coated with fluorocarbon (e.g., polytetrafluoroethylene).

FIG. 8B also illustrates a cross-section of discrete through holes 1214-7 and 1214-8 defined by the sheet layer 1212. As shown in FIG. 8B, a discrete through hole has a first opening on a first planar surface of the sheet layer 1212 and a second opening on a second planar surface, opposite to the first planar surface, of the sheet layer 1212.

In some embodiments, the sheet layer 1212 includes at least 50% of fluorocarbon by weight. Alternatively, the sheet layer 1212 may include at least 80, 90, 95, or 99% of fluorocarbon by weight. In some embodiments, the sheet layer 1212 includes at least 90% of polytetrafluoroethylene by weight. Alternatively, the sheet layer 1212 may include at least 50, 80, 95, or 99% of polytetrafluoroethylene by weight.

In some embodiments, a top portion of the sheet layer 1212 includes at least 95% of fluorocarbon by weight. As used herein, a top portion of the sheet layer 1212 refers to a layer that is defined by an exposed surface of the sheet layer 1212 and a predefined thickness. Thus, the top portion includes the exposed surface of the sheet layer 1212 and has the predefined thickness. In some embodiments, a top surface of the top portion is the exposed surface of the sheet layer 1212 and the bottom surface of the top portion has the same shape and size as the top surface of the top portion. In some embodiments, the exposed surface of the sheet layer 1212 has a flatness of at most 400 μm. In some embodiments, the bottom surface of the sheet layer 1212 has a flatness of at most 400 μm. In some embodiments, the thickness of the top portion may be 1 μm or 100 nm. In some embodiments, the top portion of the sheet layer 1212 includes at least 99% of fluorocarbon by weight.

In some embodiments, at least 90% of the exposed portion of the first surface of the first structure 1210 (e.g., the surface of the sheet layer 1212 that faces away from the second structure) is covered by fluorocarbon. In some embodiments, at least 95% of the exposed surface is covered by fluorocarbon. In some embodiments, at least 99% of the exposed portion of the first surface is covered by fluorocarbon. The PTFE-matrix does not satisfy this requirement because the resin is included in the exposed portion of the first surface. In some embodiments, at least 90% of the exposed portion of the first surface is covered by PTFE. In some embodiments, at least 95% of the exposed portion of the first surface is covered by PTFE. In some embodiments, at least 99% of the exposed portion of the first surface is covered by PTFE.

In some embodiments, the exposed portion of the first surface is characterized by advancing and receding contact angles, for a liquid selected from a group including water, ethanol, and isopropanol. The advancing and receding contact angles for the selected liquid on the exposed portion of the first surface are substantially similar to advancing and receding contact angles for the selected liquid on PTFE (e.g., a PTFE sheet containing at least 99% PTFE by weight). For example, the difference between the advancing contact angle for the selected liquid on the exposed portion of the first surface and the advancing contact angle for the selected liquid on PTFE is less than 20% or 10% of the advancing and receding contact angles for the selected liquid on PTFE.

In some embodiments, a first surface (e.g., a surface facing away from the second structure 1220) of the first structure 1210 is roughened to increase the hydrophobicity and/or oleophobicity.

In some embodiments, the second structure 1220 includes a plurality of structures that correspond to the plurality of discrete through holes in the first structure 1210.

The second structure 1220 typically includes a plastic material. In some embodiments, the plastic material includes polycarbonates. In some embodiments, the plastic material includes polystyrene. In some embodiments, the plastic material includes cyclic olefin polymer or copolymer or polystyrene.

In some embodiments, the plastic material of the second structure 1220 is optically transparent. This allows the second structure 1220 to be optically imaged from a bottom surface side of the second structure 1220.

FIG. 8C is an exploded view of an exemplary array slide 1200 in accordance with some embodiments. In FIG. 8C, the plurality of discrete through holes 1214 defined by the sheet layer 1212 of the first structure 1210 are shown. FIG. 8C also illustrates a plurality of protrusions in the second structure 1220 that correspond to the plurality of discrete through holes 1214 defined by the sheet layer 1212.

Although the sheet layer 1212 is illustrated as having a width less than the width of the second structure 1220 and a length less than the length of the second structure 1220 in FIGS. 8A-8C, in some embodiments, the sheet layer 1212 has the same width and length as the second structure 1220. Thus, the sheet layer 1212 may run from one end of the second structure to the opposite end of the second structure 1220.

Methods for Making the Array Slides

FIGS. 9A-9D are schematic diagrams illustrating selected steps for manufacturing an exemplary array slide 1200 in accordance with some embodiments.

Figure 9A:
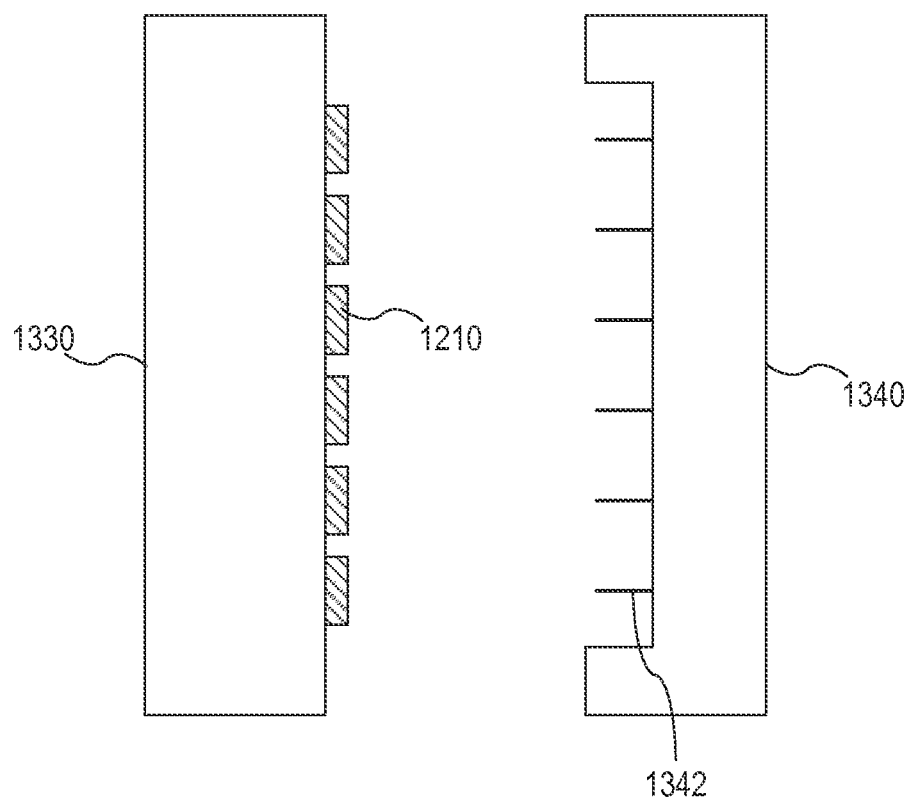
FIGS. 9A-9D are schematic diagrams illustrating selected steps for manufacturing an exemplary array slide in accordance with some embodiments.

FIG. 9A illustrates that the first structure 1210 is held in a first mold component 1330 by vacuum suction. The vacuum suction pulls the first structure 1210 toward the first mold component 1330 so that the first structure 1210 remains flat through the molding process. Typically, the vacuum suction is applied over a plurality of locations on the first structure 1210. The vacuum suction typically leaves one or more indentations on the surface of the first structure 1210 facing the first mold component 1330. In some embodiments, the first mold component 1330 includes a plurality of vacuum holes (not shown).

In some embodiments, a plurality of pins 1342 coupled with the second mold component 1340 are spring loaded so that the plurality of pins 1342 are configured to apply force on the first structure 1210 toward the first mold component 1330 when the first mold component 1330 and the second mold component 1340 are assembled together.

In some embodiments, the bottom surface of the first structure 1210 (e.g., the surface facing the second mold component 1340) is treated, typically before the first structure 1210 is held in the first mold component 1330, to facilitate coupling with the second structure 1220. In some embodiments, the bottom surface of the first structure 1210 is treated to reduce the hydrophobicity (e.g., increase the surface tension) of the first structure 1210. In some embodiments, the bottom surface of the first structure 1210 is roughened to increate the contact area with the second structure 1220.

In some embodiments, the first mold component 1330 has a flat surface or a portion of the surface that is flat facing the first structure 1210. In some embodiments, the surface of the first mold component 1330 has protrusions and/or indentations, the impact of which is described above with respect to FIGS. 5A-5C. For brevity, these descriptions are not repeated herein.

Figure 9B:
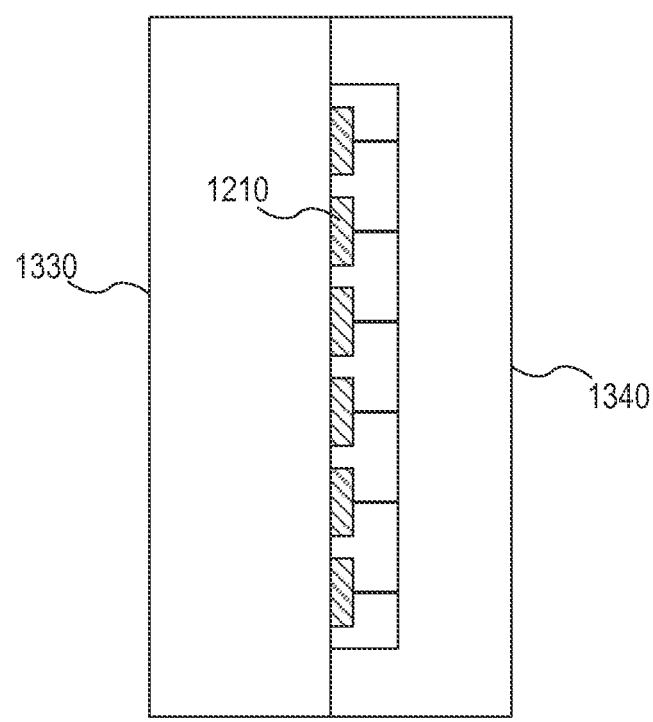

FIG. 9B illustrates that the first mold component 1330 and the second mold component 1340 are assembled, thereby forming a cavity inside, into which a heated plastic material is introduced for a molding process.

Figure 9C:
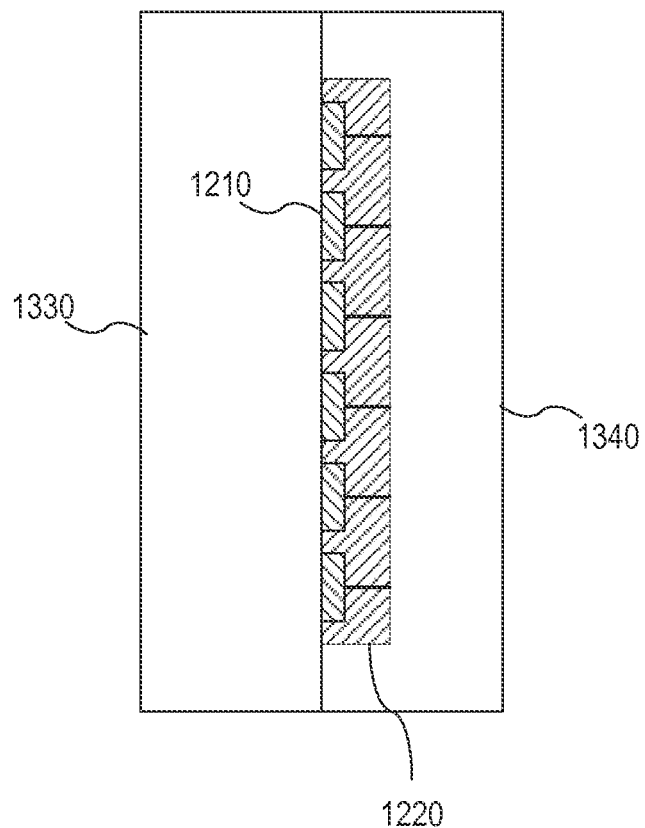

FIG. 9C illustrates that a heated plastic material is introduced into the cavity. In some embodiments, the plastic material includes polycarbonates. In some embodiments, the plastic material includes polystyrene. In some embodiments, the plastic material includes cyclic olefin polymer or copolymer or polystyrene. The heated plastic material fills the cavity.

Once the heated plastic material is cooled, the plastic material forms the second structure 1220. When the second structure 1220 is formed, the second structure 1220 is coupled with the first structure 1210 so as to form the array slide 1200.

Figure 9D:
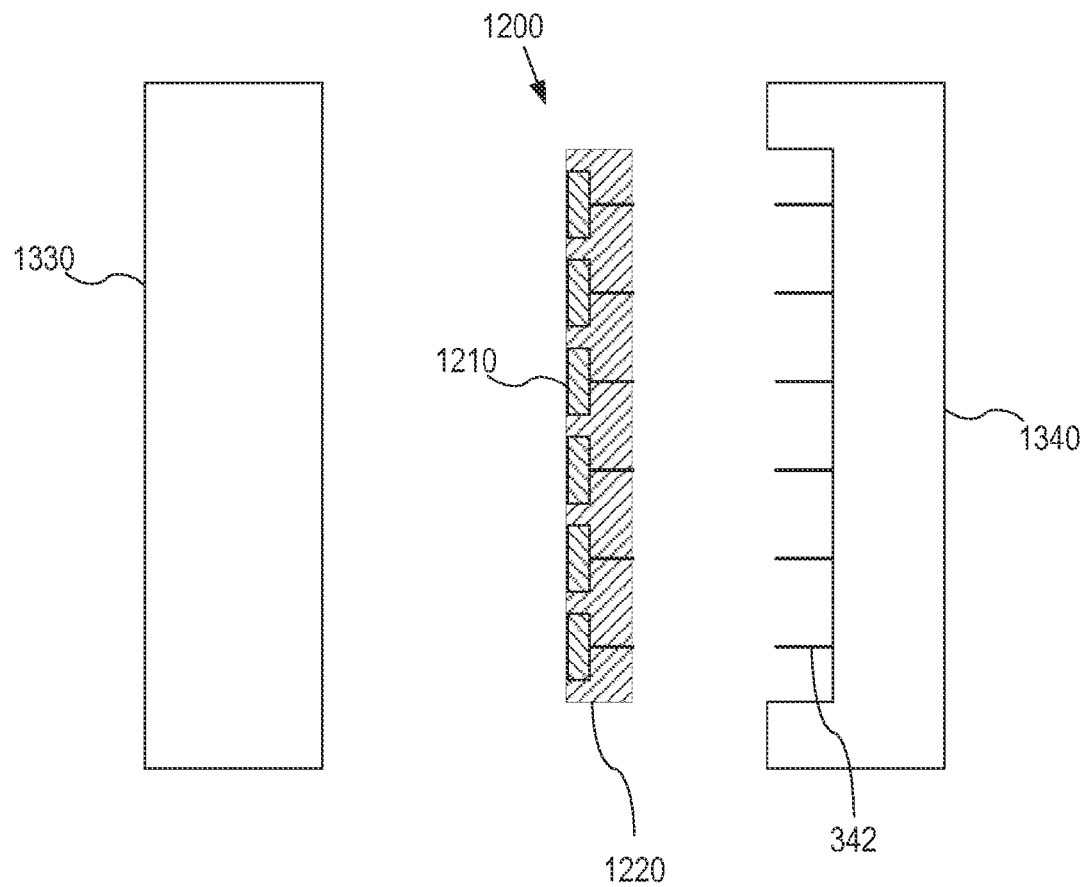

FIG. 9D illustrates that the array slide 1200 is removed from the first mold component 1330 and the second mold component 1340.

Note that the array slide 1200 removed from the first mold component 1330 and the second mold component 1340 has pin marks corresponding to the plurality of pins 1342 coupled with the second mold component 1340. When optical measurements (e.g., collection of optical images or optical signals) are performed through respective portions of the second structure 1220 corresponding to the plurality of discrete through holes defined in the first structure 1210, if the pin marks are located at the respective portions of the second structure 1220 corresponding to the plurality of discrete through holes defined in the first structure 1210, the pin marks interfere optical measurements. Thus, to avoid the interference by the pin marks, the plurality of pins 1342 are located offset from the plurality of discrete through holes defined in the first structure 1210.

Although FIGS. 9A-9D illustrate forming the array slide 1200 by using both the vacuum suction and the plurality of pins 1342, in some embodiments, only one of the vacuum suction and the plurality of pins 1342 is used. For example, the vacuum suction may be used without using the plurality of pins 1342. Alternatively, the plurality of pins 1342 may be used without the vacuum suction.

Additional Features of Array Slides

Figure 10A:
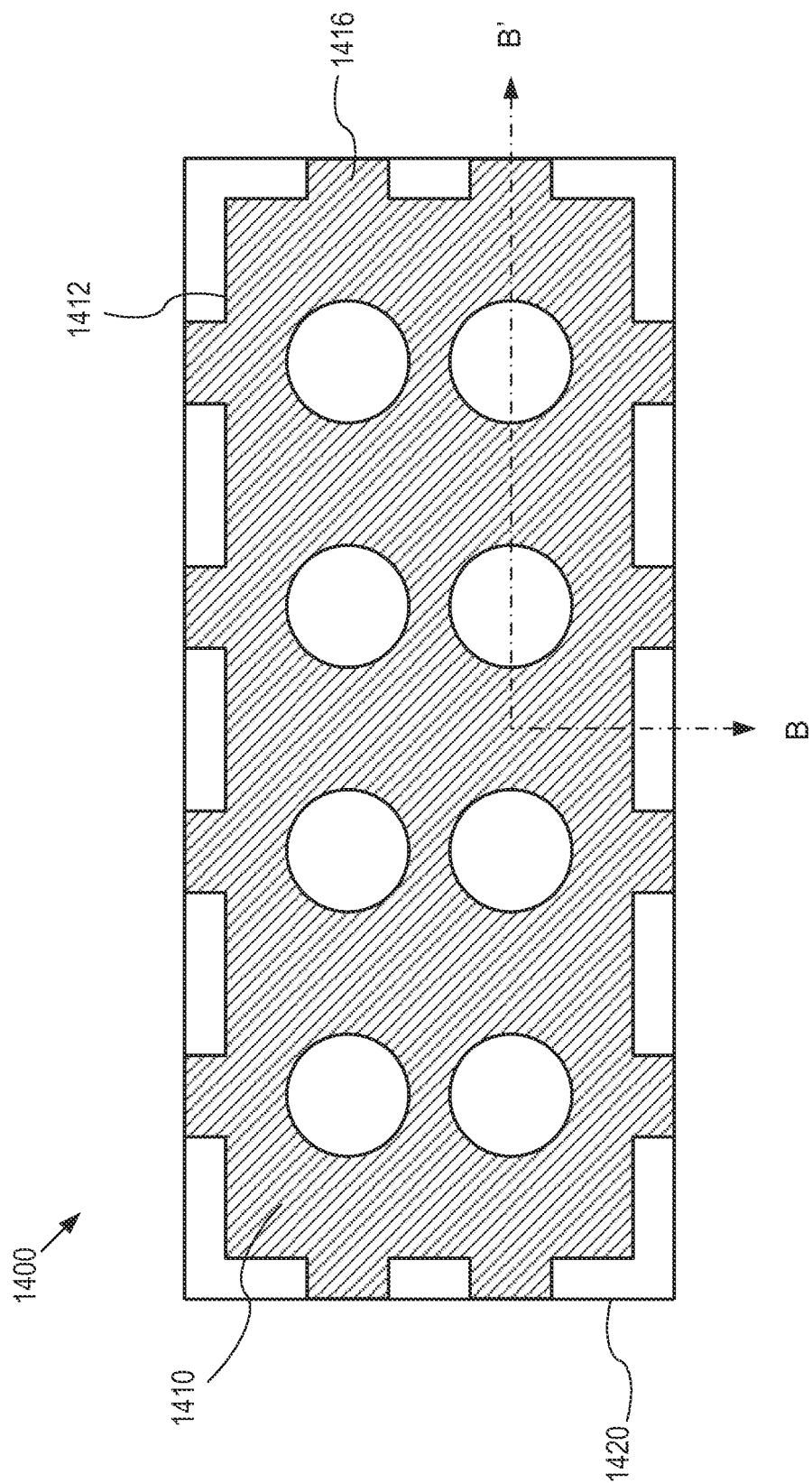
FIG. 10A is a top-down view of an exemplary array slide in accordance with some embodiments.

FIG. 10A is a top-down view of an exemplary array slide 1400 in accordance with some embodiments. The array slide 1400 has one or more characteristics of the array slide 1200 described above with respect to FIGS. 8A-8C. The descriptions of such characteristics are not repeated for brevity.

The array slide 1400 has a first structure 1410 and a second structure 1420. The first structure 1410 includes a sheet layer 1412 and one or more connectors 1416. In some embodiments, the one or more connectors 1416 are integrated in the sheet layer 1412.

FIG. 10A also indicates a line B-B' across the array slide 1400. The line B-B' corresponds to the cross-sectional view illustrated in FIG. 10B.

Figure 10B:
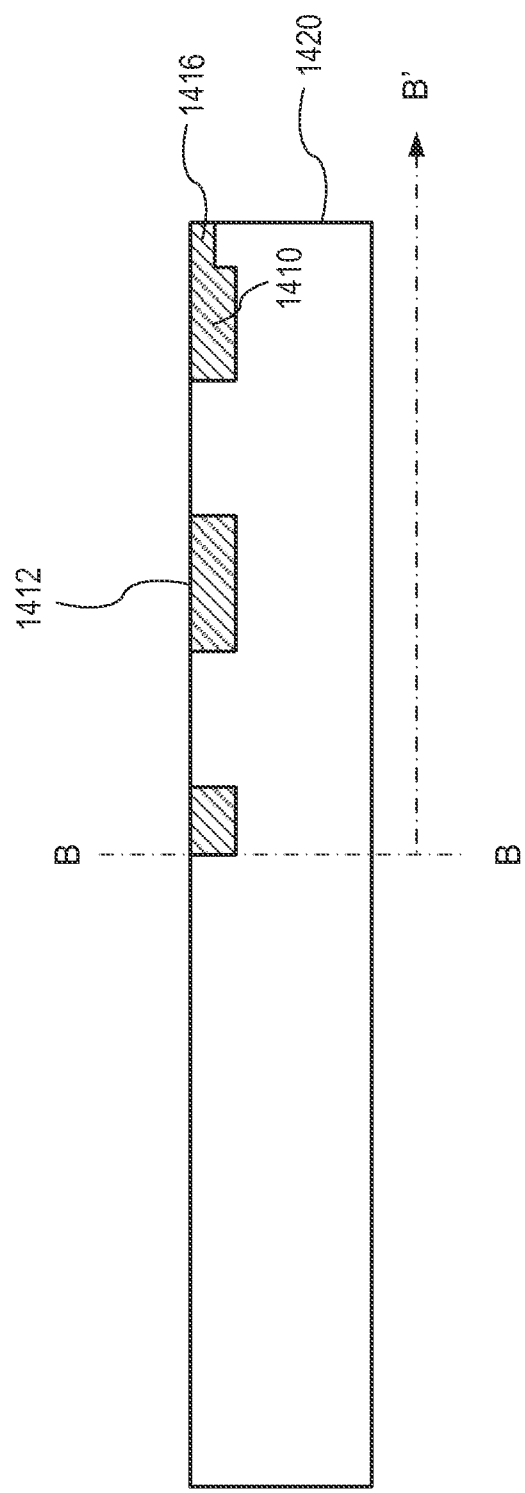
FIG. 10B is a partial cross-sectional view of an exemplary array slide in accordance with some embodiments.

FIG. 10B is a partial cross-sectional view of the exemplary array slide 1400 in accordance with some embodiments. The partial cross-sectional view shown in FIG. 10B has one or more characteristics of the partial cross-sectional view shown in FIG. 8B. The descriptions of such characteristics are not repeated for brevity.

The first structure 1410 includes one or more connectors 1416. In some embodiments, at least one of the connectors 1416 is positioned so that its top surface is aligned with the top surface of the sheet layer 1412. However, as explained below with respect to FIG. 11B, at least one of the connectors 1416 may be positioned that its top surface is positioned below the top surface of the second structure 1412 (e.g., the top surface of the connectors 1416 is embedded in the second structure 1420).

The one or more connectors 1416 serve multiple functions. For example, the one or more connectors 1416, in particular when the one or more connectors 1416 are embedded in the second structure 1420, prevents the peeling of the first structure 1410 from the second structure 1420. The one or more connectors 1416 also allow first structures for multiple array slides to be held together in the molding cavity. This facilitates the manufacturing of multiple array slides.

Figure 10C:
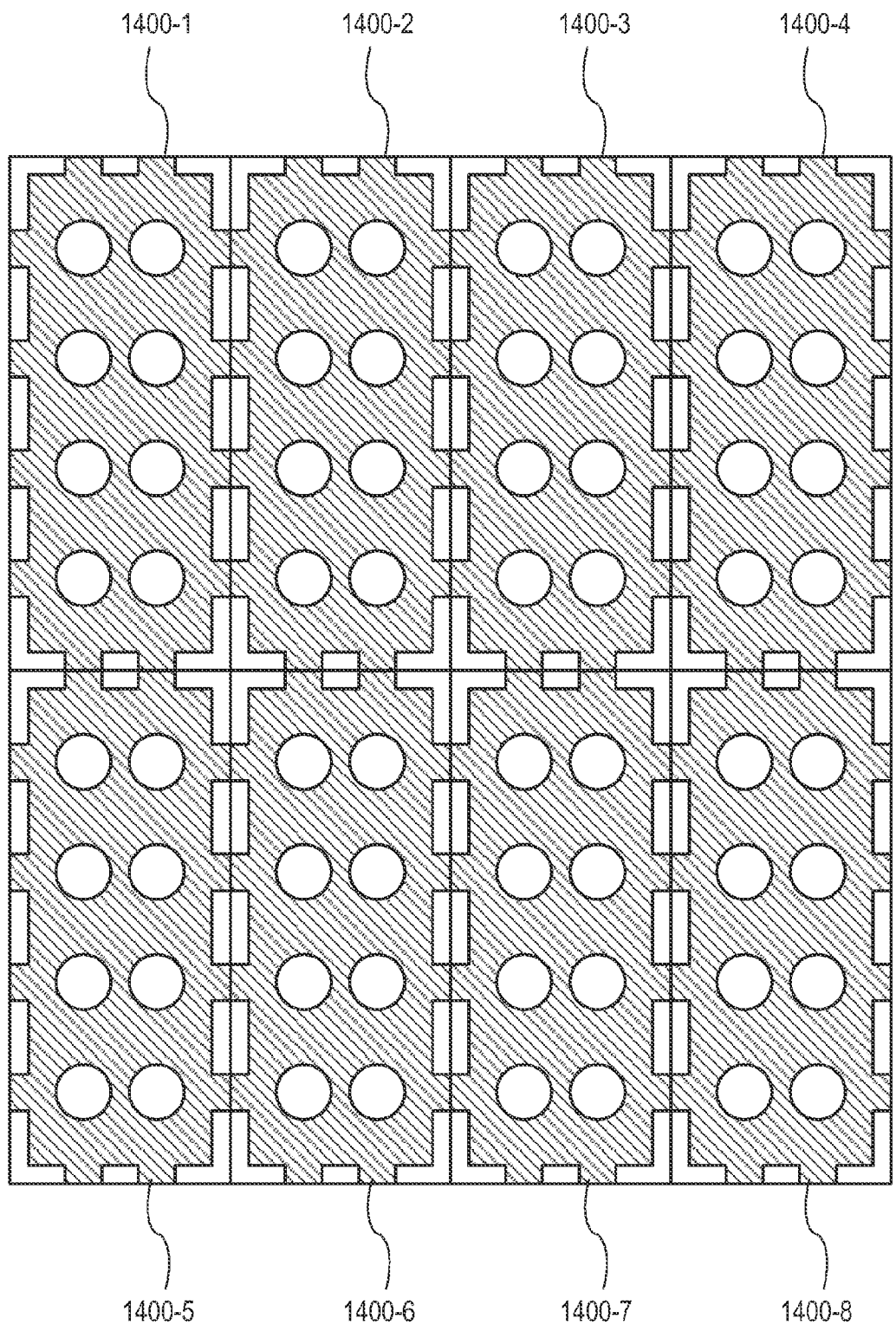
FIG. 10C is a top-down view of exemplary array slides in accordance with some embodiments.

FIG. 10C is a top-down view of exemplary array slides (1400-1 through 1400-8) in accordance with some embodiments. The array slides (1400-1 through 1400-8) shown in FIG. 10C can be formed in a single molding process. For example, in some embodiments, instead of placing a single first structure in a molding cavity as illustrated in FIGS. 9A-9D, an array of first structures is placed in a molding cavity, and the molding steps (e.g., filling the cavity with heated plastic material and cooling the plastic material to form second structures). After the array of array slides (1400-1 through 1400-8) is formed, the array slides may be separated (e.g., by cutting the array along boundary lines between array slides).

Figure 11A:
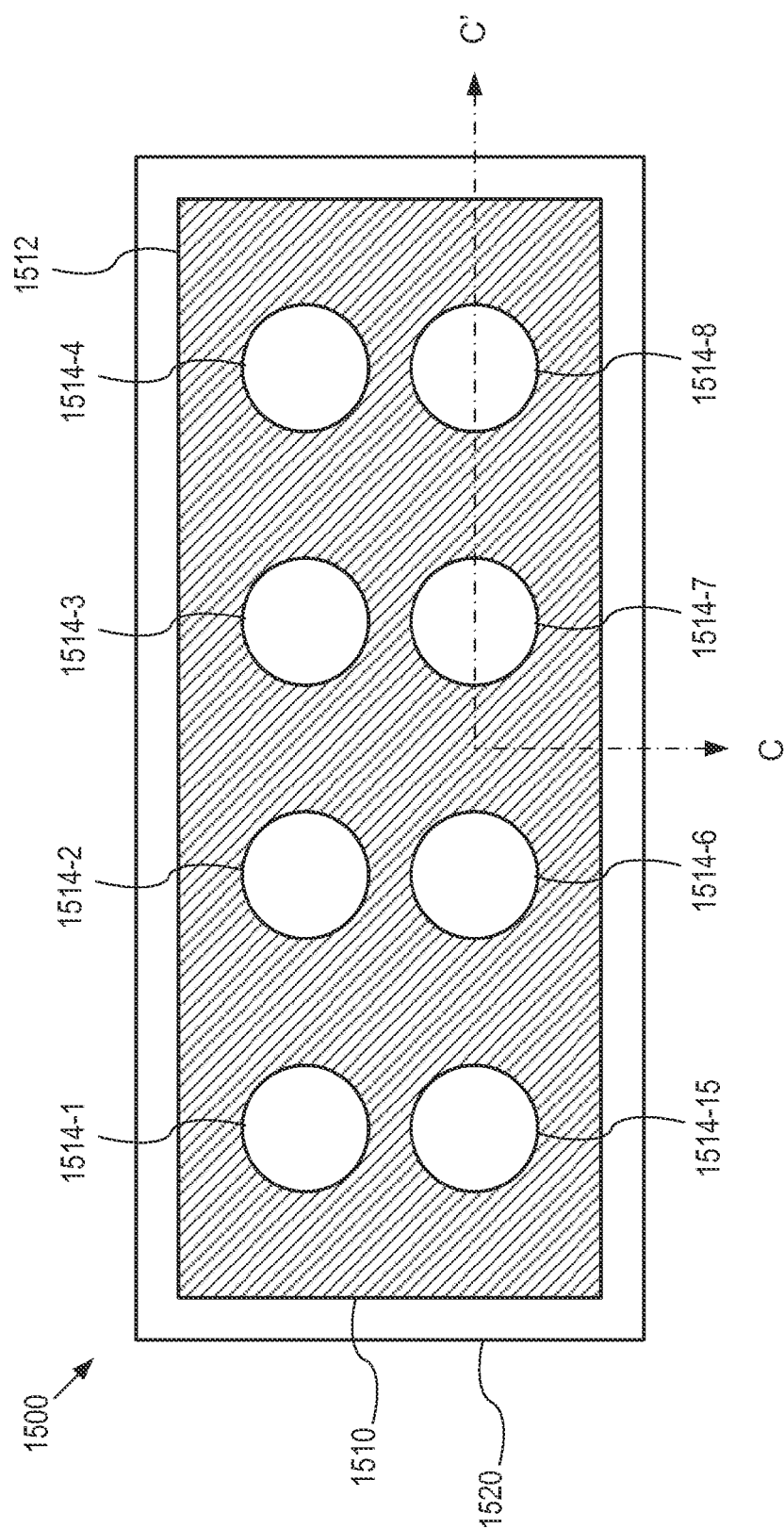
FIG. 11A is a top-down view of an exemplary array slide in accordance with some embodiments.

FIG. 11A is a top-down view of an exemplary array slide 1500 in accordance with some embodiments. The array slide 1500 has one or more characteristics of the array slides 1200 and 1400 described above with respect to FIGS. 8A-8C and FIGS. 10A-10C. The descriptions of such characteristics are not repeated for brevity.

The array slide 1500 has a first structure 1510 and a second structure 1520. The first structure 1510 includes a sheet layer 1512 and one or more connectors (not shown). The sheet layer 1512 defines a plurality of discrete through holes (1514-1 through 1514-8).

FIG. 11A also indicates a line C-C' across the array slide 1500. The line C-C' corresponds to the cross-sectional view illustrated in FIG. 11B.

Figure 11B:
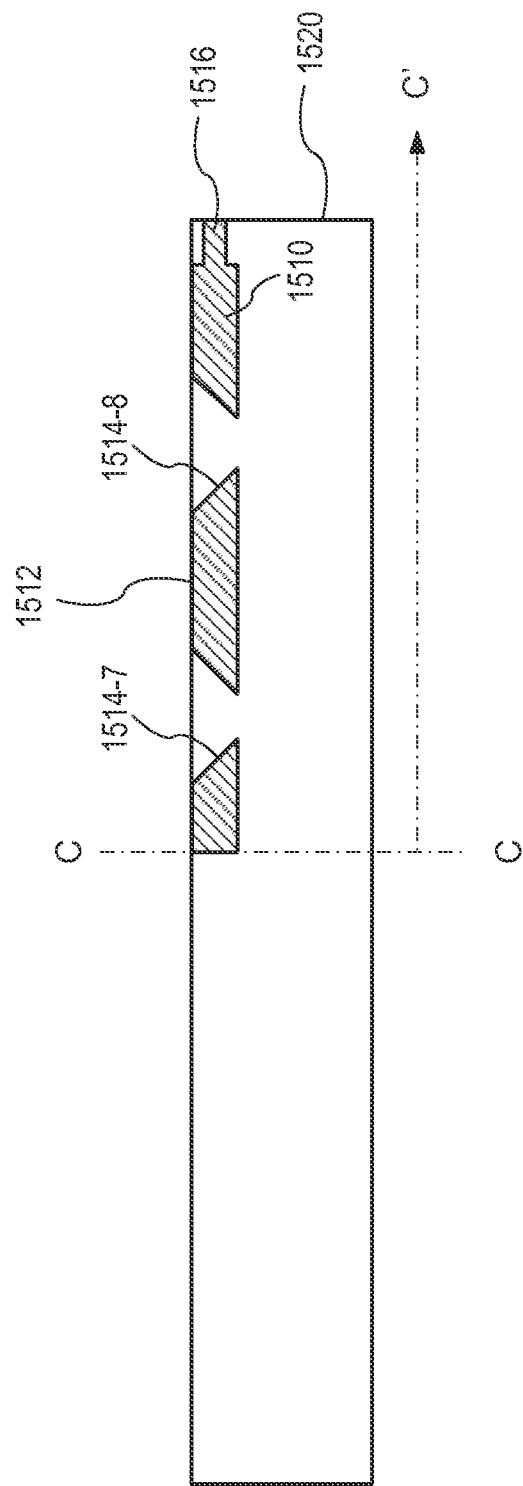
FIG. 11B is a partial cross-sectional view of an exemplary array slide in accordance with some embodiments.
Figure 12B:
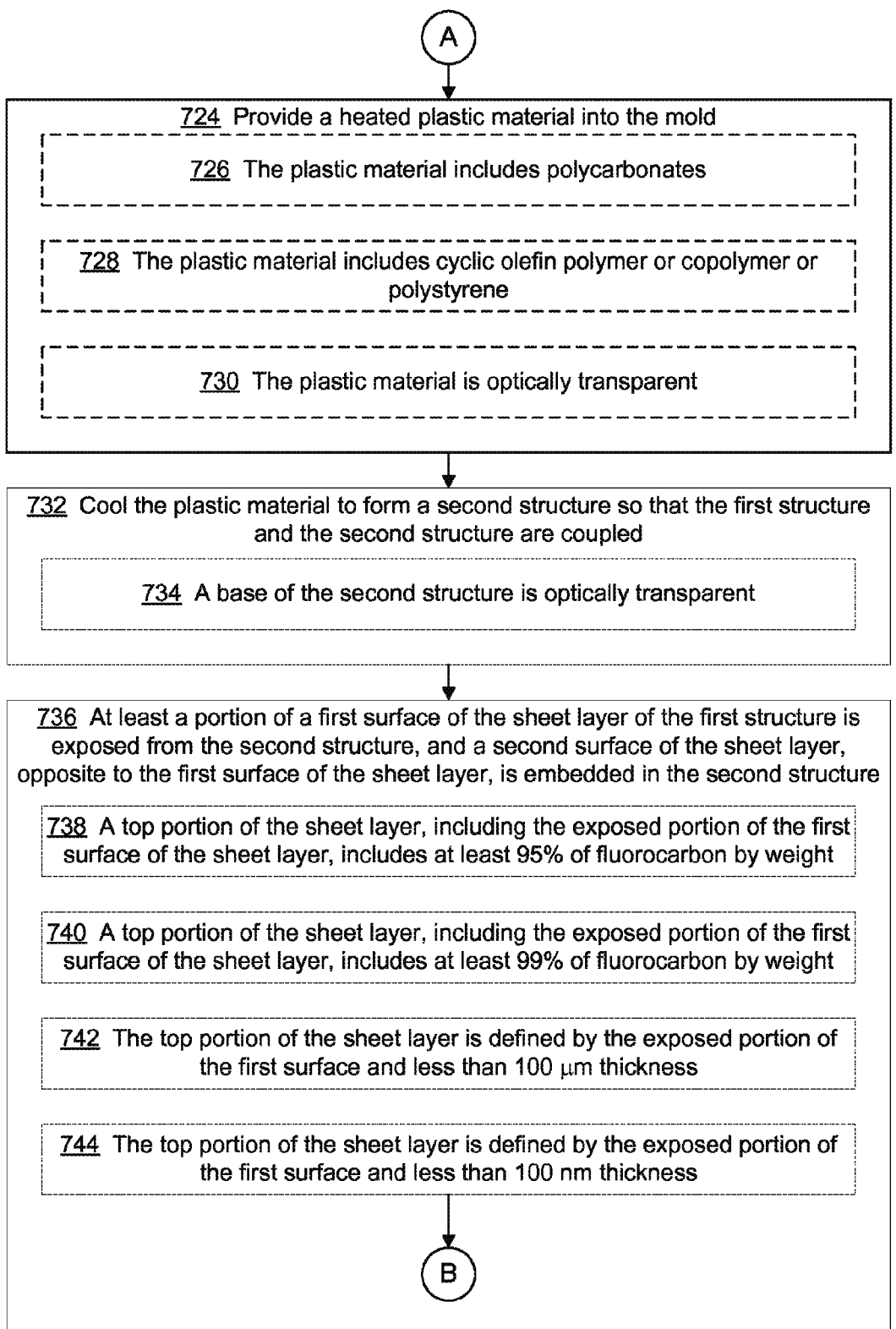

FIG. 11B is a partial cross-sectional view of the exemplary array slide 1500 in accordance with some embodiments. The partial cross-sectional view shown in FIG. 11B has one or more characteristics of the partial cross-sectional view shown in FIG. 11B. The descriptions of such characteristics are not repeated for brevity.

The first structure 1510 includes one or more connectors 1516. In FIG. 11B, at least one of the connectors 1416 is positioned so that its top surface is positioned below the top surface of the second structure 1520 (e.g., the top surface of the connectors 1416 is embedded in the second structure 1520). This reduces the peeling (i.e., separation) of the first structure 1510 from the second structure 1520.

FIG. 11B also illustrates that one or more sides of the first structure 1510 are angled. For example, the sides of the through holes 1514-7 and 1514-8 are angled. As shown in FIG. 11B, a cross-sectional view of the sheet layer 1512 includes a trapezoidal shape. As a result, the top surface of the sheet layer 1512 has a smaller area than the bottom surface of the sheet layer 1512. This further reduces the peeling (i.e., separation) of the first structure 1510 from the second structure 1520.

Although FIG. 11B illustrates the angled sides of the first structure 1510 have having straight lines, in some embodiments, the sides of the first structure 1510 have curves (e.g., concave or convex).

Although FIGS. 11A-11B illustrate embodiments that implement both the connectors and the angled sides, it is possible to implement only one of two features. For example, as illustrated in FIGS. 10A-10C, the connectors may be implemented without the implementing angled sides. Alternatively, the angled sides may be implemented without implementing the connectors.

FIGS. 12A-12D are flow charts representing a method 700 of making an array slide in accordance with some embodiments.

The method includes (702) providing a first structure in a mold (e.g., FIG. 9A). The first structure includes a sheet layer with a plurality of discrete through holes (e.g., FIG. 8C).

In some embodiments, the sheet layer includes (704) at least 50% of fluorocarbon by weight. In some embodiments, the sheet layer includes (706) at least 90% of fluorocarbon by weight. In some embodiments, the sheet layer includes (708) at least 95% of fluorocarbon by weight. In some embodiments, the sheet layer includes (710) at least 99% of fluorocarbon by weight.

In some embodiments, the sheet layer includes (712) at least 90% of polytetrafluoroethylene by weight. In some embodiments, the sheet layer includes (714) at least 95% of polytetrafluoroethylene by weight. In some embodiments, the sheet layer includes (716) at least 99% of polytetrafluoroethylene by weight.

In some embodiments, the method includes (718) pressing the first structure against a first surface of a mold prior to providing the heated plastic material (e.g., FIGS. 9A-9B).

In some embodiments, pressing the first structure against the first surface of the mold includes (720) pressing the first surface of the sheet layer against the first surface of the mold with a plurality of pins at least on the second surface of the sheet layer (e.g., FIG. 9B).

In some embodiments, the method includes (722) providing vacuum suction on the first surface of the sheet layer (e.g., FIG. 9A).

The method includes (724) providing a heated plastic material into the mold (e.g., FIG. 9C).

In some embodiments, the plastic material includes (726) polycarbonates. In some embodiments, the plastic material includes polystyrene.

In some embodiments, the plastic material includes (728) cyclic olefin polymer or copolymer or polystyrene.

In some embodiments, the plastic material is (730) optically transparent. In some embodiments, the plastic material is optically transparent for a wavelength range selected from the group consisting of: 250-900 nm, 35-850 nm, 400-800 m, 450-800 nm, and 500-800 nm.

The method includes (732) cooling the plastic material to form a second structure so that the first structure and the second structure are coupled (e.g., FIGS. 9C-9D).

In some embodiments, a base of the second structure is (734) optically transparent. A base of the second structure includes one or more portions of the second structure located below the plurality of discrete through holes defined by the first structure. In some embodiments, the base is optically transparent for a wavelength range selected from the group consisting of: 250-900 nm, 35-850 nm, 400-800 m, 450-800 nm, and 500-800 nm.

At least a portion of a first surface of the sheet layer of the first structure is exposed (736) from the second structure, and a second surface of the sheet layer, opposite to the first surface of the sheet layer, is embedded in the second structure (e.g., FIGS. 8B, 10B, and 11B).

In some embodiments, a top portion of the sheet layer, including the exposed portion of the first surface of the sheet layer, includes (738) at least 95% of fluorocarbon by weight. In some embodiments, a top portion of the sheet layer, including the exposed portion of the first surface of the sheet layer, includes (740) at least 99% of fluorocarbon by weight.

In some embodiments, the top portion of the sheet layer is defined (742) by the exposed portion of the first surface and less than 1 μm thickness.

In some embodiments, the top portion of the sheet layer is defined (744) by the exposed portion of the first surface and less than 100 nm thickness.

In some embodiments, at least 90% of the exposed portion of the first surface is covered (746) by fluorocarbon. In some embodiments, at least 95% of the exposed portion of the first surface is covered (748) by fluorocarbon. In some embodiments, at least 99% of the exposed portion of the first surface is covered (750) by fluorocarbon.

In some embodiments, at least 90% of the exposed portion of the first surface is covered (752) by polytetrafluoroethylene. In some embodiments, at least 95% of the exposed portion of the first surface is covered (754) by polytetrafluoroethylene. In some embodiments, at least 99% of the exposed portion of the first surface is covered (756) by polytetrafluoroethylene.

In some embodiments, the exposed portion of the first surface is characterized (758) by advancing and receding contact angles, for a liquid selected from a group including water, ethanol, and isopropanol, that are similar to advancing and receding contact angles, for the selected liquid, on polytetrafluoroethylene.

In some embodiments, the second structure includes (760) a plurality of holding locations. The method includes aligning the first structure and the second structure so that the plurality of discrete through holes defined in the sheet layer of the first structure is offset from the plurality of holding locations in the second structure.

In some embodiments, the mold is configured (762) so that a top surface of the sheet layer of the first structure is aligned with a top surface of a base layer of the second structure (e.g., FIG. 5A).

In some embodiments, the mold is configured (764) so that a top surface of the sheet layer of the first structure is above a top surface of a base layer of the second structure (e.g., FIG. 5C). In some embodiments, the mold is configured (766) so that a top surface of the sheet layer of the first structure is below a top surface of a base layer of the second structure (e.g., FIG. 5B). In some embodiments, the first surface of the mold has (768) one or more of: a plurality of indentations and a plurality of protrusions, corresponding to the plurality of discrete through holes defined in the sheet layer.

In some embodiments, at least a portion of the first surface of the sheet layer is embedded (770) in the second structure. For example, the second structure covers along a periphery of discrete through holes defined by the sheet layer over the first surface of the sheet layer. In some embodiments, a plurality of portions of the first surface of the sheet layer is embedded in the second structure.

In some embodiments, the first structure includes (772) one or more connectors coupled to one or more sides of the sheet layer (e.g., FIGS. 10A-10C and FIG. 11B). In some embodiments, the one or more connectors are embedded (774) in the second structure (e.g., FIG. 11B).

In some embodiments, at least a portion of the sides of the sheet layer is angled (776) (e.g., FIG. 11B). In some embodiments, the sides, other than the inner walls of the discrete through holes, of the sheet layer are angled. In some embodiments, an inner wall of at least one discrete through hole of the sheet layer is angled (778) (e.g., FIG. 11B).

In some embodiments, the second surface of the sheet layer has a larger area than the first surface of the sheet layer (780) (e.g., FIG. 11B)

In some embodiments, the method includes (782) coating a portion of the second structure with oil. In some embodiments, the method includes coating (784) a portion of the first surface of the sheet layer of the first structure with the oil. In some embodiments, the oil is selected (786) from the group consisting of mineral oil, silicone oil, a hydrocarbon compound, a hydroperfluorocarbon compound and a perfluorocarbon compound.

Methods for Using the Array Slides

In some embodiments, a method for using an array slide includes providing the array slide, and providing one or more biological and/or chemical samples for processing.

In some embodiments, a method for using an array slide includes placing the array slide in a reservoir. The method includes storing a liquid medium in the reservoir of the device so that the first surface of the sheet layer is covered by the liquid medium, and dispensing respective liquid droplets on respective locations on the base layer. The respective locations correspond to locations of the plurality of discrete through holes defined in the sheet layer, and the respective liquid droplets are immiscible with the liquid medium.

In some embodiments, a method includes processing a sample (e.g., cells, particles or beads conjugated with target molecules, etc.) by placing a plurality of droplets on respective regions of the second structure that are not covered by the first structure. Respective droplets include a sample for processing. The method also includes adding one or more biological and/or chemical reagents to the respective droplets.

In some embodiments, a method includes washing a sample. Methods for washing a sample are described in more detail below with respect to FIGS. 13 to 18.

Figure 13:
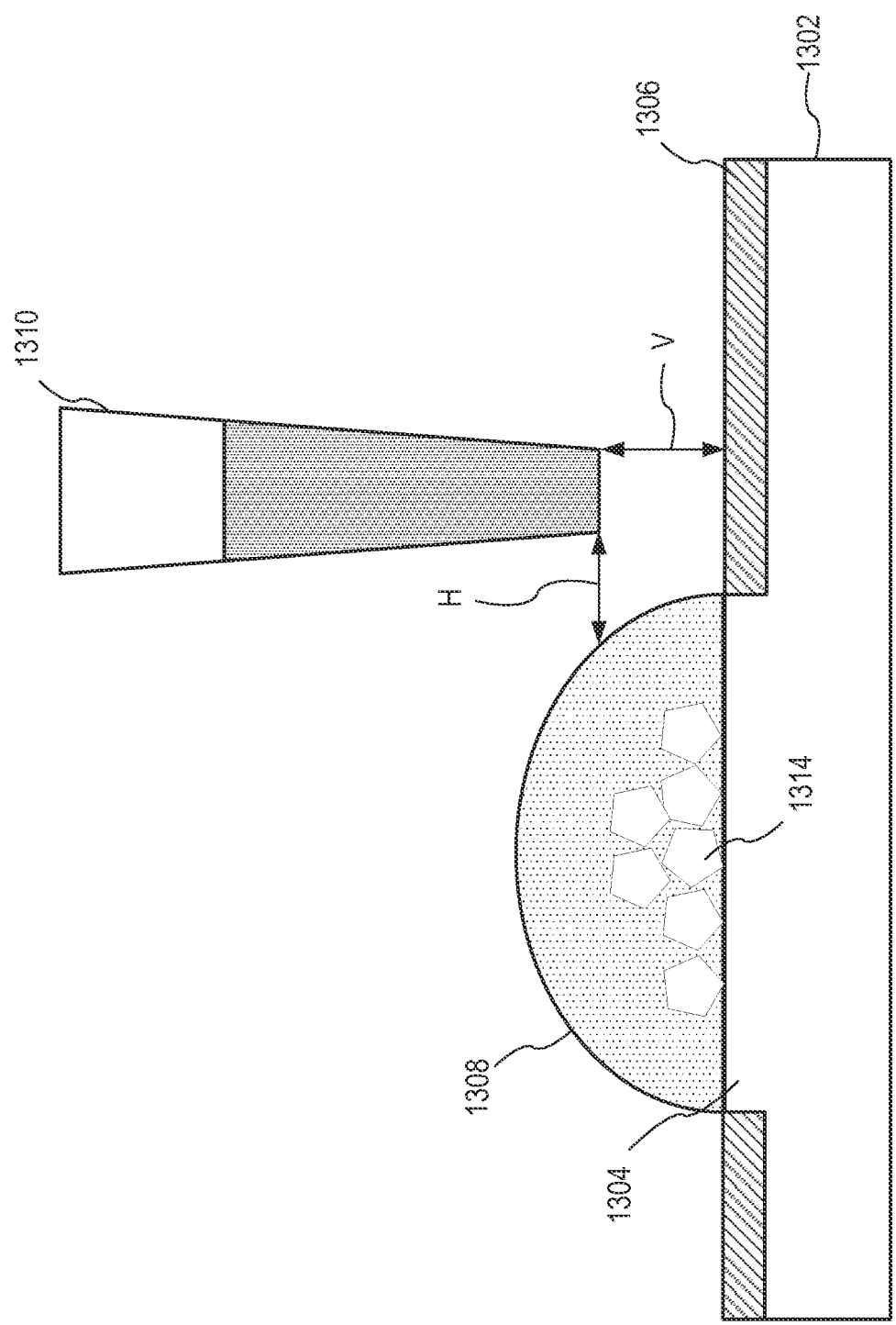
FIG. 13 is a partial cross-sectional view of an exemplary array slide in accordance with some embodiments.

FIG. 13 is a partial cross-sectional view of an exemplary array slide in accordance with some embodiments.

FIG. 13 illustrates a slide 1302 covered with a hydrophobic layer 1306 so that a portion 1304 of the slide 1302 is exposed. The exposed portion 1304 of the slide 1302 typically includes a hydrophilic area. In FIG. 13, a sample droplet 1308 that contains a sample solution (e.g., a solution that includes a plurality of cells, particles, and/or beads 1314) is located on the exposed portion 1304 of the slide 1302. For washing the plurality of cells, particles, and/or beads 1314 in the sample solution, a pipette tip 1310 is placed to add a wash solution to the sample solution, thereby mixing the wash solution and the sample solution, followed by removing a portion of the mixed solution. In some embodiments, it is desirable to remove the portion of the mixed solution while maintaining a significant portion (e.g., more than 75%, 90%, or 95%) of the plurality of cells, particles, and/or beads 1314. In some embodiments, it is desirable to remove the portion of the mixed solution without removing any of the plurality of cells, particles, and/or beads 1314.

When a wash solution is dispensed from the pipette tip 1310, the wash solution forms a wash droplet (e.g., a droplet that includes the wash solution, not shown). Due to the surface tension of the sample droplet 1308 and the wash droplet, merging the sample droplet 1308 and the wash droplet frequently agitates the plurality of cells, particles, and/or beads 1314 in the sample droplet 1308. For example, in some cases, suspension cells that have settled down to the bottom of the sample droplet 1308 are agitated and float around in the sample droplet 1308 when the sample droplet 1308 merges with the wash droplet. In another example, in some cases, adherent cells and/or weakly adherent cells that have adhered to the hydrophilic area in the exposed portion 1304 break free from the hydrophilic area and float around in the sample droplet 1308 when the sample droplet 1308 merges with the wash droplet.

As used herein, the term "adherent cells" is used interchangeably with "anchorage-dependent cells," which refers to cells requiring a solid substratum (e.g., the solid glass or plastic surface of a culture dish or micro-carrier beads), for growth and proliferation. Anchorage-dependent cells typically do not grow well in suspension cultures or semi-solid soft agar. Exemplary adherent cells are liver or liver-derived cells including primary hepatocytes and liver epithelial cells, epithelial cells in general, endothelial cells in general, neuronal cells, mesenchymal cells, pancreatic cells, skeletal muscle cells, cardiomyocytes, carcinoma-derived cells, bone marrow cells, islets of Langerhans, adrenal medulla cells, osteoblasts, osteoclasts, T-lymphocytes, neurons, glial cells, ganglion cells, retinal cells, and myoblast cells. Stem cells can also be used; examples are mesenchymal stem cells, neuronal stem cells, induced pluripotent stem cells, hematopoietic stem cells, mouse embryonic stem cells, and human embryonic stem cells. Many other examples exist and will be readily apparent to those of skill in the art.

As used herein, the term "suspension cells" is used interchangeably with "anchorage independent cells," which refers to cells that grow or proliferate independent of attachment to a solid substratum (e.g., cells that do not require attachment to a solid substratum for growth or proliferation). Exemplary suspension cultures are derived from cells of the blood system because these cells are also suspended in plasma in vitro (e.g. lymphocytes). In some embodiments, suspension cells include semi-adherent cells (e.g., weakly adherent cells) and non-adherent cells.

It has been found that by placing the pipette tip 1310 in accordance with predefined proximity criteria and dispensing a wash solution in accordance with predefined dispensing criteria, the agitation of the plurality of cells 1314 in the sample droplet 1308 is reduced. In FIG. 13, the pipette tip 1310 is located at a distance H from the sample droplet 1308, and a distance V from a top surface of the slide 1302 or the hydrophobic layer 1306.

In one example, for a sample droplet with 8-12 µl sample solution that is located on a hydrophilic area that has 3.5 mm diameter, a pipette tip located 2 mm or less from the sample droplet and 2 mm or less from a top surface of the slide 1302 (or a hydrophobic layer on the slide 1302) is found to reduce agitation of cells 1314 in the sample droplet during washing. In some cases, the pipette tip is located 500 µm or less inside the sample droplet. In some cases, a washing solution is dispensed at a rate of 10 µl/sec or less. In particular, for a sample droplet with 8-12 µl sample solution that is located on a hydrophilic area that has a 3.5 mm diameter, a pipette tip located 250 µm from the sample droplet and 700 µm from the top surface of the slide 1302 (or a hydrophobic layer on the slide 1302) is found to reduce agitation of cells 1314 in the sample droplet during washing. The reduction in agitation of cells 1314 in the sample droplet during washing is observed based on a number of cells 1314 retained on the hydrophilic area after the washing.

Figure 18:
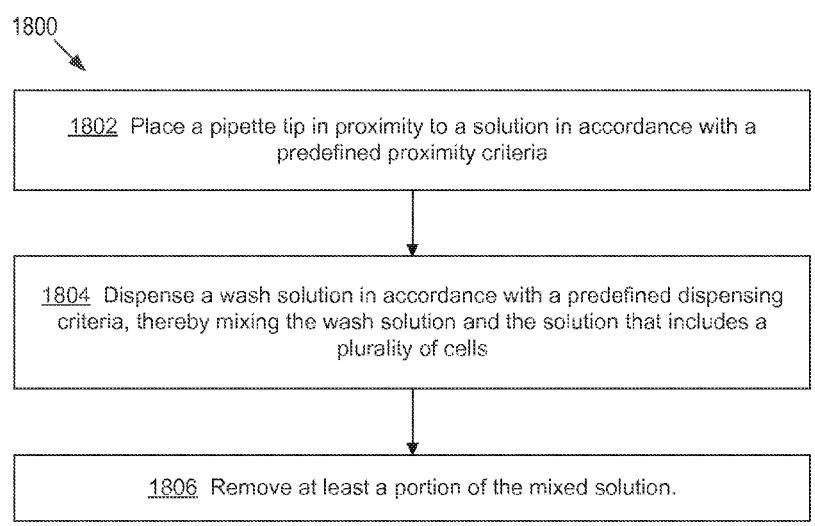
FIG. 18 is a flow chart representing a method for washing a sample in accordance with some embodiments.

FIG. 18 is a flow chart representing a method 1800 for washing a plurality of cells in accordance with some embodiments.

The method 1800 includes (1802) placing a pipette tip in proximity to a solution (e.g., a pipette tip 1310 in proximity to a sample solution in a sample droplet 1308 in FIG. 13) in accordance with predefined proximity criteria.

In some embodiments, the predefined proximity criteria includes that the pipette tip is located at a predefined distance (e.g., a horizontal distance) from the solution (e.g., 2 mm or less, 1 mm or less, 500 µm or less, and 250 µm or less). In some embodiments, the predefined proximity criteria includes that the pipette tip is located 500 µm or less inside the solution.

In some embodiments, the predefined proximity criteria includes that the pipette tip is located at a predefined distance (e.g., a vertical distance) from a hydrophilic area on which the solution is located. For example, the predefined proximity criteria may include that the pipette tip is located 2 mm or less, 1 mm or less, 700 µm or less, 500 µm or less, 250 µm or less, or 100 µm or less from the hydrophilic area.

The method 1800 includes (1804) dispensing a wash solution in accordance with predefined dispensing criteria. In some embodiments, dispensing the wash solution includes mixing the wash solution and the solution that includes a plurality of cells (e.g., a sample solution).

In some embodiments, the predefined dispensing criteria includes that the wash solution is dispensed at a predefined dispensing rate (e.g., 10 µl/sec or less, 5 µl/sec or less, 2 µl/sec or less, 1 µl/sec or less, and 0.1 µl/sec or less).

The method 1800 includes (1806) removing at least a portion of the mixed solution (e.g., a mixture of the wash solution and the sample solution that includes the plurality of cells). In some embodiments, the method includes removing at least a portion of the mixed solution at a predefined aspiration rate (e.g., 10 µl/sec or less, 5 µl/sec or less, 2 µl/sec or less, 1 µl/sec or less, and 0.1 µl/sec or less). In some embodiments, removing at least a portion of the mixed solution includes removing at least a portion of the mixed solution without removing a sample (e.g., cells) in the mixed solution. In some embodiments, removing at least a portion of the mixed solution includes removing at least a portion of the mixed solution without removing more than a predefined amount of the sample (e.g., cells) in the mixed solution (e.g., 1%, 5%, 10%, or 20%).

Array Slides and Plates with Secondary Areas

It has been found that using a plate or slide that includes primary areas and associated secondary areas further improves the methods of washing a sample in a sample solution.

Figure 14A:
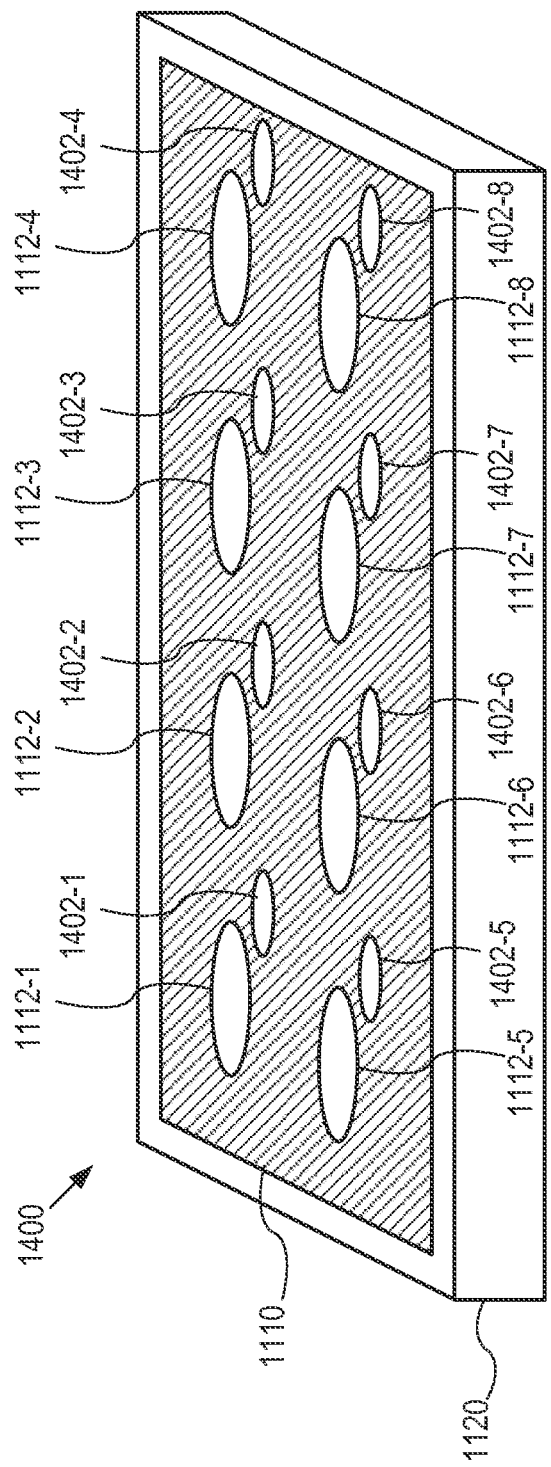
FIG. 14A is a perspective view of an exemplary array slide in accordance with some embodiments.

FIG. 14A is a perspective view of an exemplary array slide 1400 in accordance with some embodiments. The array slide 1400 shown in FIG. 14A is similar to the array slide 1100 shown in FIG. 7. Thus, the similar details of the first structure 1110, the second structure 1120, and the plurality of discrete through holes 1112 are not repeated for brevity. In FIG. 14A, secondary through holes (e.g., 1402-1 through 1402-8) are located adjacent to respective through holes (e.g., 1112-1 through 1112-8). In particular, a respective secondary through hole (e.g., 1402-1) is located adjacent to a respective "primary" through hole (e.g., 1112-1).

As used herein, for a plate or slide that includes a component (e.g., a first structure) with primary through holes and secondary through holes, a primary through hole defines a primary area on a second component (e.g., a second structure) and a secondary through hole defines a secondary area on the second component (e.g., the second structure) During use, a sample solution is located on the primary area and a wash solution is dispended on, or a mixture of the wash solution and the sample solution is removed from, the secondary area. However, in some embodiments, a primary area and a secondary area are defined without using a primary through hole and a secondary through hole. In some embodiments, the primary area and the secondary area are formed by treating a hydrophobic surface (e.g., chemically and/or physically). For example, in some embodiments, primary and secondary areas are formed by chemically treating a hydrophobic surface to form hydrophilic areas. In some embodiments, primary and secondary areas are formed by physically treating a hydrophobic surface to form hydrophilic areas. In some embodiments, primary and secondary areas are formed by chemically treating a hydrophilic surface to form one or more hydrophobic areas surrounding the hydrophilic primary and secondary areas. In some embodiments, primary and secondary areas are formed by physically treating a hydrophilic surface to form one or more hydrophobic areas surrounding the hydrophilic primary and secondary areas. In another example, the primary area and the secondary area are formed by applying a hydrophobic coating on a remaining area of a hydrophilic surface.

In some embodiments, the respective primary area is larger than a respective secondary of the one or more secondary areas adjacent to the respective primary area.

In some embodiments, a respective secondary area is deemed to be adjacent to a respective primary area when the secondary area is closer to the respective primary area than any primary area other than the respective primary area.

Although FIG. 14A shows that a single secondary through hole (e.g., 1402-1) is located adjacent to a respective primary through hole (e.g., 1112-1), in some embodiments, multiple secondary through holes are located adjacent to a respective primary through hole (e.g., FIGS. 15I-15L).

Figure 14B:
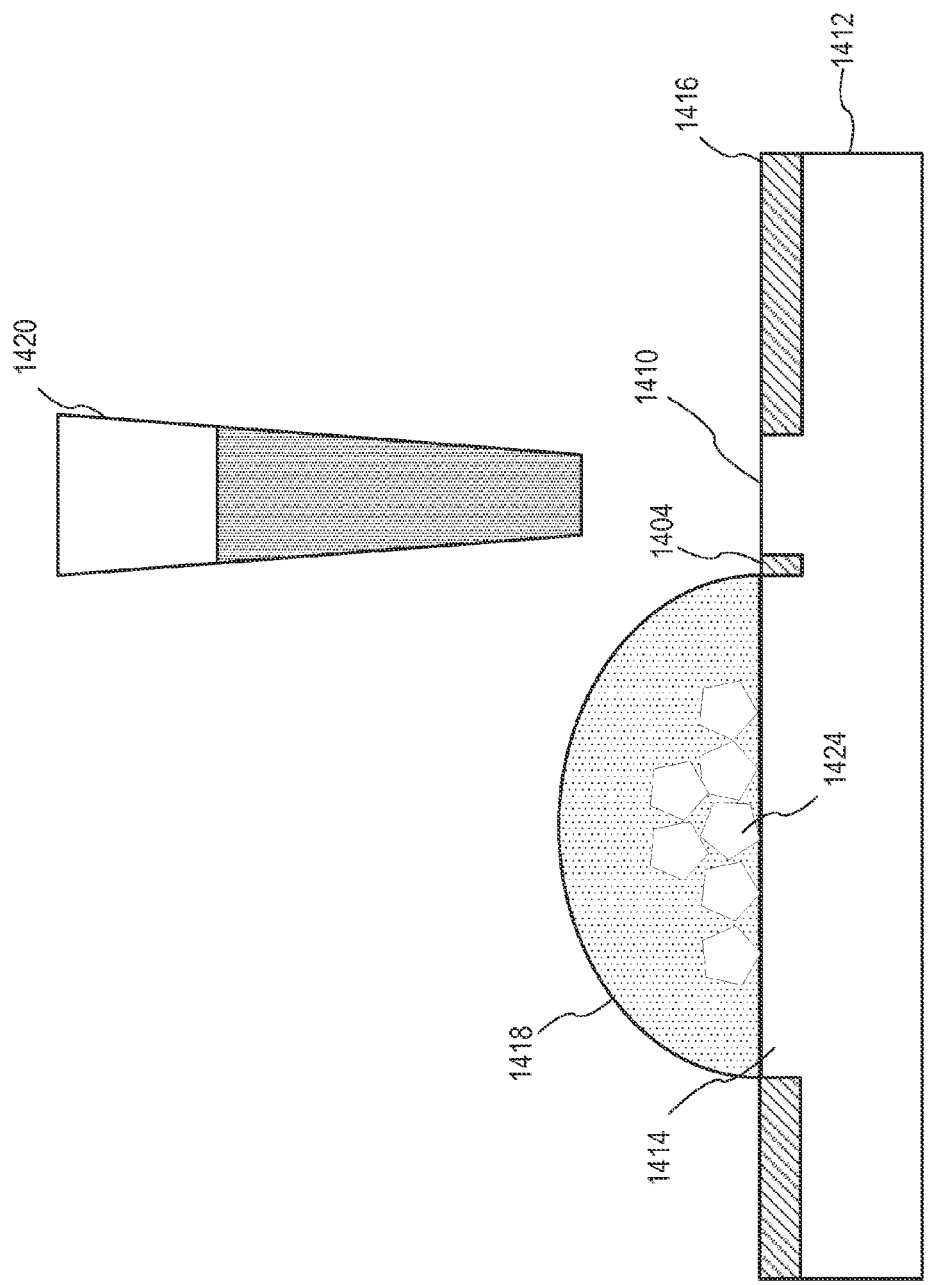

FIG. 14B is a partial cross-sectional view of an exemplary array slide 1400 in accordance with some embodiments.

FIG. 14B illustrates a slide 1412 covered with a hydrophobic layer 1416 so that a portion 1414 of the slide 1412 is exposed. The exposed portion 1414 of the slide 1412 typically includes a hydrophilic area. In FIG. 14B, a sample droplet 1418 that contains a sample solution (e.g., a solution that includes a plurality of cells, particles, and/or beads 1424) is located on the exposed portion 1414 of the slide 1412. In FIG. 14B, the slide 1412 also defines a secondary area 1410 configured to receive a wash solution. FIG. 14B shows that the secondary area 1410 is separated from the exposed portion 1414 (which serves as a primary area) by a hydrophobic element 1404. For washing the plurality of cells, particles, and/or beads 1424 in the sample solution, a pipette tip 1420 is placed to add a wash solution to the sample solution, thereby mixing the wash solution and the sample solution, followed by removing a portion of the mixed solution. The washing method is described in detail with respect to FIGS. 13 and 17-18, and thus is not repeated herein.

FIG. 14C illustrates a slide 1432 covered with a hydrophobic layer 1416 so that a portion 1434 of the slide 1412 is exposed. The exposed portion 1414 of the slide 1412 typically includes a hydrophilic area. In FIG. 14C, the exposed portion 1414 includes a primary area and a secondary area connected to the primary area (e.g., see FIGS. 15B-15H).

Figure 14D:
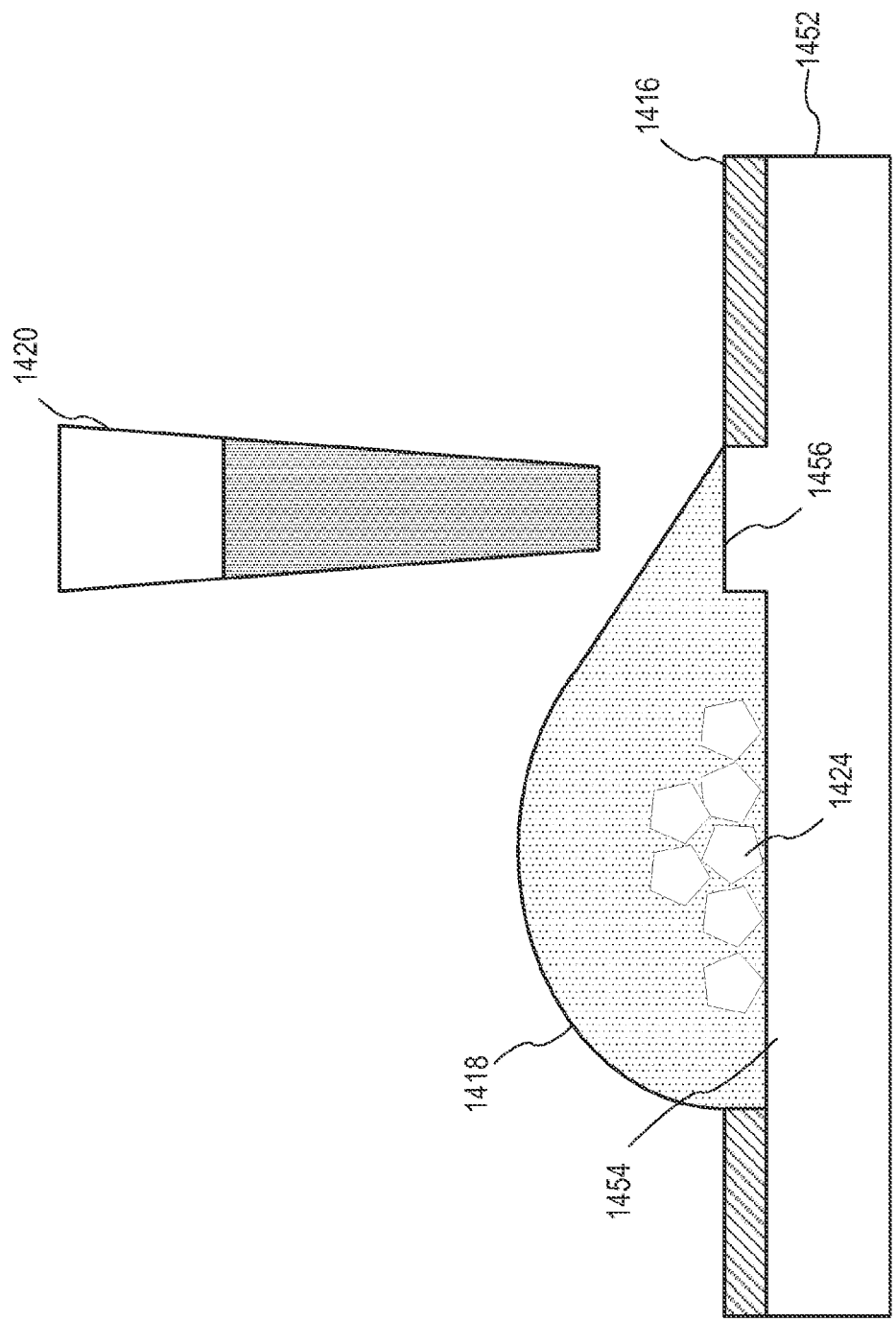

FIG. 14D illustrates a slide 1452 covered with a hydrophobic layer 1416 so that a primary area 1454 and a secondary area 1456 of the slide 1452 are exposed. The primary area 1454 and the secondary area 1456 are typically hydrophilic areas.

In some embodiments, the primary area 1454 and the secondary area 1456 are located on different planes. For example, in some embodiments, as shown in FIG. 14D, the primary area 1454 is indented from the secondary area 1456 (e.g., the primary area 1454 is positioned lower than the secondary area 1456). It has been found that the indented primary area is especially effective at retaining cells, particles, and/or beads 1424 during washing. In some embodiments, the primary area 1454 is indented from the secondary area 1456 by at least 10 μm (e.g., a vertical distance between the primary area 1454 and the secondary area 1456 is at least 10 μm). In some embodiments, the primary area 1454 is indented from the secondary area 1456 by at least 20 μm (e.g., a vertical distance between the primary area 1454 and the secondary area 1456 is at least 20 μm). In some embodiments, the primary area 1454 is indented from the secondary area 1456 by 2 mm or less (e.g., a vertical distance between the primary area 1454 and the secondary area 1456 is 2 mm or less). In some embodiments, the primary area 1454 is indented from the secondary area 1456 by 500 μm or less (e.g., a vertical distance between the primary area 1454 and the secondary area 1456 is 500 μm or less). In some embodiments, the primary area 1454 is indented from the secondary area 1456 by 10 μm or more and 2 mm or less, by 20 μm or more and 500 μm or less, by 100 μm or more and 500 μm or less, or by 250 μm or more and 500 μm or less (e.g., a vertical distance between the primary area 1454 and the secondary area 1456 is between 10 μm and 2 mm, between 20 μm and 500 μm, between 100 μm and 500 μm, or between 250 μm and 500 μm.

In some embodiments, the primary area 1454 is surrounded by a background area (e.g., hydrophobic element 1404, FIG. 14B) and indented from the background area (e.g., the primary area 1454 is positioned lower than the background area). In some embodiments, the primary area 1454 is indented from the background area by at least 10 μm (e.g., a vertical distance between the primary area 1454 and the background area is at least 10 μm). In some embodiments, the primary area 1454 is indented from the background area by at least 20 μm (e.g., a vertical distance between the primary area 1454 and the background area is at least 20 μm). In some embodiments, the primary area 1454 is indented from the background area by 2 mm or less (e.g., a vertical distance between the primary area 1454 and the background area is 2 mm or less). In some embodiments, the primary area 1454 is indented from the background area by 500 μm or less (e.g., a vertical distance between the primary area 1454 and the background area is 500 μm or less). In some embodiments, the primary area 1454 is indented from the background area by 10 μm or more and 2 mm or less, by 20 μm or more and 500 μm or less, by 100 μm or more and 500 μm or less, or by 250 μm or more and 500 μm or less (e.g., a vertical distance between the primary area 1454 and the background area is between 10 μm and 2 mm, between 20 μm and 500 μm, between 100 μm and 500 μm, or between 250 μm and 500 μm.

In some other embodiments, the secondary area 1456 is indented from the primary area 1454 (e.g., the primary area 1454 is positioned higher than the secondary area 1456) (not shown).

In some embodiments, the indented primary area 1454 has a depth that is less than 50% of a width of the primary area (e.g., a circular primary area with a 6 mm diameter has less than 3 mm depth). In some embodiments, the indented primary area 1454 has a depth that is less than 10% of a width of the primary area. In some embodiments, the indented primary area 1454 has a depth that is less than 5% of a width of the primary area. In some embodiments, the indented primary area 1454 has a depth that is less than 3% of a width of the primary area. In some embodiments, the indented primary area 1454 has a depth that is less than 1% of a width of the primary area.

FIGS. 15A-15L are partial top views of exemplary array plates (or array slides) in accordance with some embodiments.

Figure 15A:
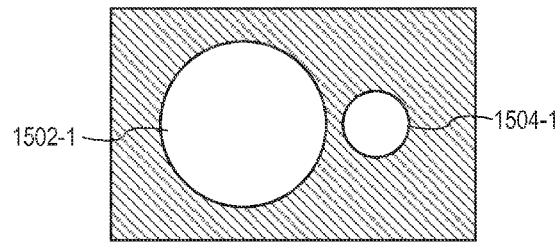
FIGS. 15A-15L are partial top views of exemplary array plates in accordance with some embodiments.

In FIG. 15A, a primary through hole (e.g., 1502-1) has a first shape of a first circle and a secondary through hole (e.g., 1504-1) has a second shape of a second circle. As shown in FIG. 15A, in some embodiments, the first shape is distinct from the second shape (e.g., the first circle has a diameter distinct from a diameter of the second circle). The primary through hole and the secondary through hole in FIG. 15A are separated. In addition, a primary area defined by the primary through hole and a secondary area defined by the secondary through hole are separated.

Figure 15B:
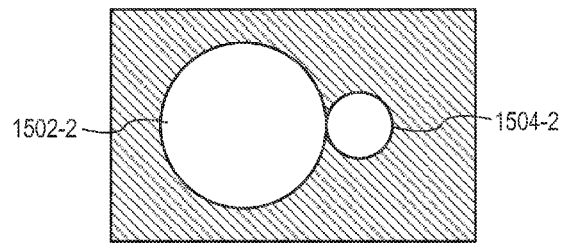

FIG. 15B illustrates a primary through hole (e.g., 1502-2) having a first shape of a first circle and a secondary through hole (e.g., 1504-2) having a second shape of a second circle. In some embodiments, as shown in FIG. 15B, the primary through hole and the secondary through hole are in contact with each other. However, the primary through hole and the secondary through hole in FIG. 15B do not overlap.

Figure 15C:
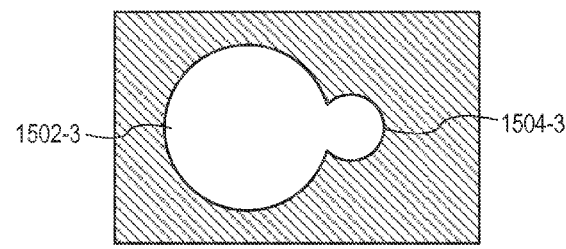

FIG. 15C illustrates a primary through hole (e.g., 1502-3) having a first shape of a first circle and a secondary through hole (e.g., 1504-3) having a second shape of a second circle.

In some embodiments, as shown in FIG. 15C, a portion of the primary through hole and a portion of the secondary through hole in FIG. 15C overlap. In FIG. 15C, the primary through hole includes a portion that does not overlap with the secondary through hole. Similarly, as shown in FIG. 15C, the secondary through hole includes a portion that does not overlap with the primary through hole.

Although the primary through holes and the secondary through holes in FIGS. 15A-15C are illustrated as having circular shapes, the shapes of the primary through holes and the secondary through holes are not limited to circles.

Figure 15D:
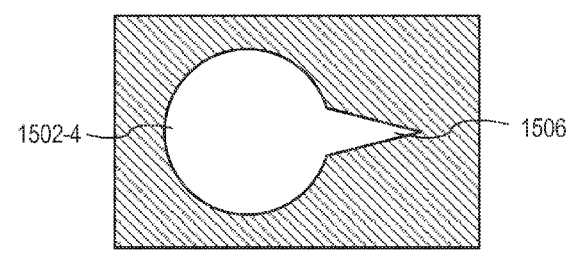

FIG. 15D illustrates a primary through hole (e.g., 1502-4) having a shape of a circle and a secondary through hole (e.g., 1506) having a shape of a triangle. In some embodiments, as shown in FIG. 15D, a portion of the primary through hole and a portion of the secondary through hole overlap. In some other embodiments, the primary through hole and the secondary through hole are separated.

Figure 15E:
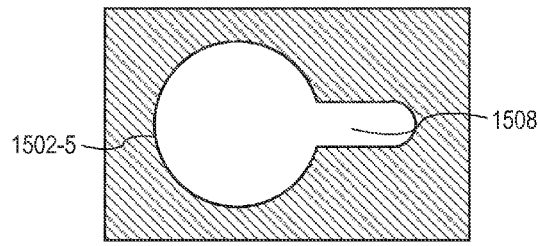

FIG. 15E illustrates a primary through hole (e.g., 1502-5) having a shape of a circle and a secondary through hole (e.g., 1508) having a shape of a rectangle. In some embodiments, as shown in FIG. 15E, one end of the rectangle, opposite from the primary through hole is rounded. In some other embodiments, the rectangle is not rounded. In some embodiments, as shown in FIG. 15E, a portion of the primary through hole and a portion of the secondary through hole overlap. In some other embodiments, the primary through hole and the secondary through hole are separated.

Figure 15F:
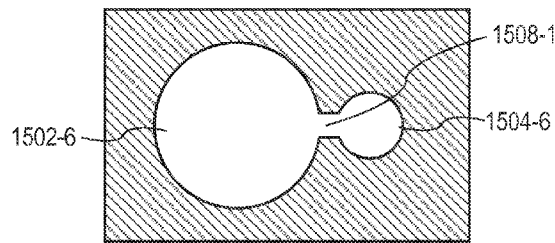
Figure 15G:
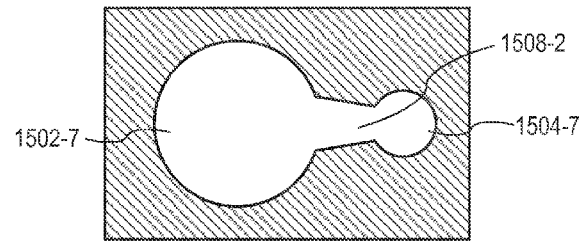
Figure 15H:
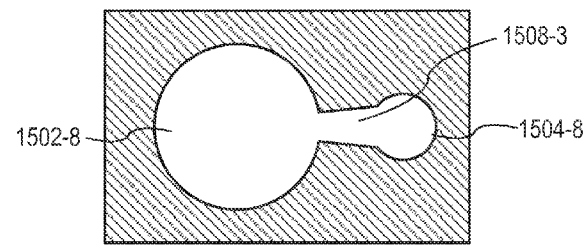
Figure 15I:
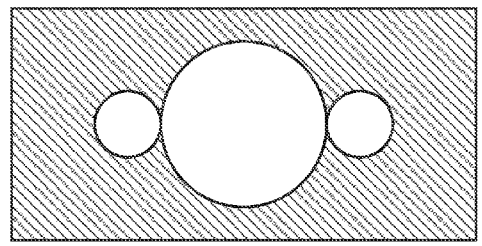
Figure 15J:
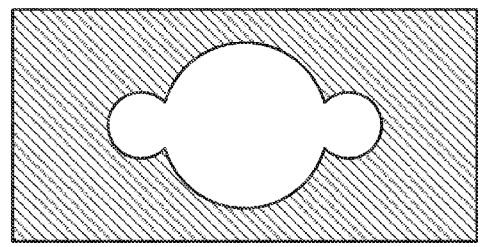
Figure 15K:
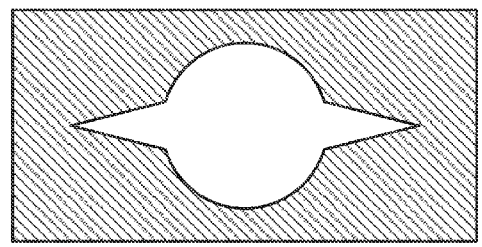

In some embodiments, as shown in FIGS. 15F-15H, a respective primary through hole is coupled with a respective secondary through hole through a channel.

FIG. 15F illustrates that a respective primary through hole (e.g., 1502-6) is coupled with a respective secondary through hole (e.g., 1504-6) through a channel (e.g., 1508-1). In some embodiments, as shown in FIG. 15G, the channel (e.g., 1508-1) has a uniform width.

In other embodiments, the channel has a non-uniform width. For example, in some embodiments, as shown in FIG. 15G, channel 1508-2 has a first width adjacent to the respective primary through hole (e.g., 1502-7) and a second width adjacent to the respective secondary through hole (e.g., 1504-7), and the first width is wider than the second width. In some other embodiments, as shown in FIG. 15H, channel 1508-3 has a first width adjacent to the respective primary through hole (e.g., 1502-8) and a second width adjacent to the respective secondary through hole (e.g., 1504-8), and the first width is narrower than the second width.

FIGS. 15I-15L illustrate that multiple secondary through holes are coupled with a respective primary through hole. Although each of FIGS. 15I-15L shows two secondary through holes coupled with one primary through hole, in some embodiments, three or more (e.g., three, four, six, eight, etc.) secondary through holes are coupled with one primary through hole.

Figure 15L:
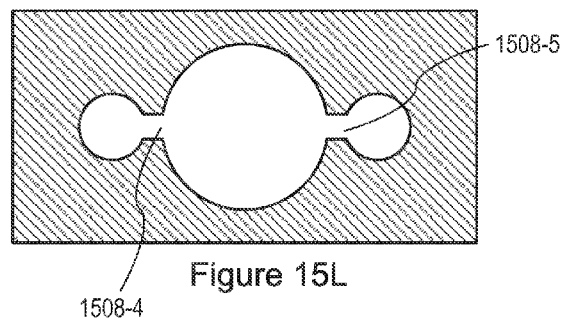

In some embodiments, a respective primary through hole is coupled with multiple secondary through holes through respective channels (e.g., 1508-4 and 1508-5 in FIG. 15L).

Although the array plates (or array slides) in FIGS. 15A-15L have been described with primary and secondary through holes, a person having ordinary skill in the art would understand that, in some embodiments, primary areas and secondary areas are arranged as shown in one of FIGS. 15A-15L, without using primary through holes and secondary through holes, as explained above with respect to FIG. 14A.

Figure 16A:
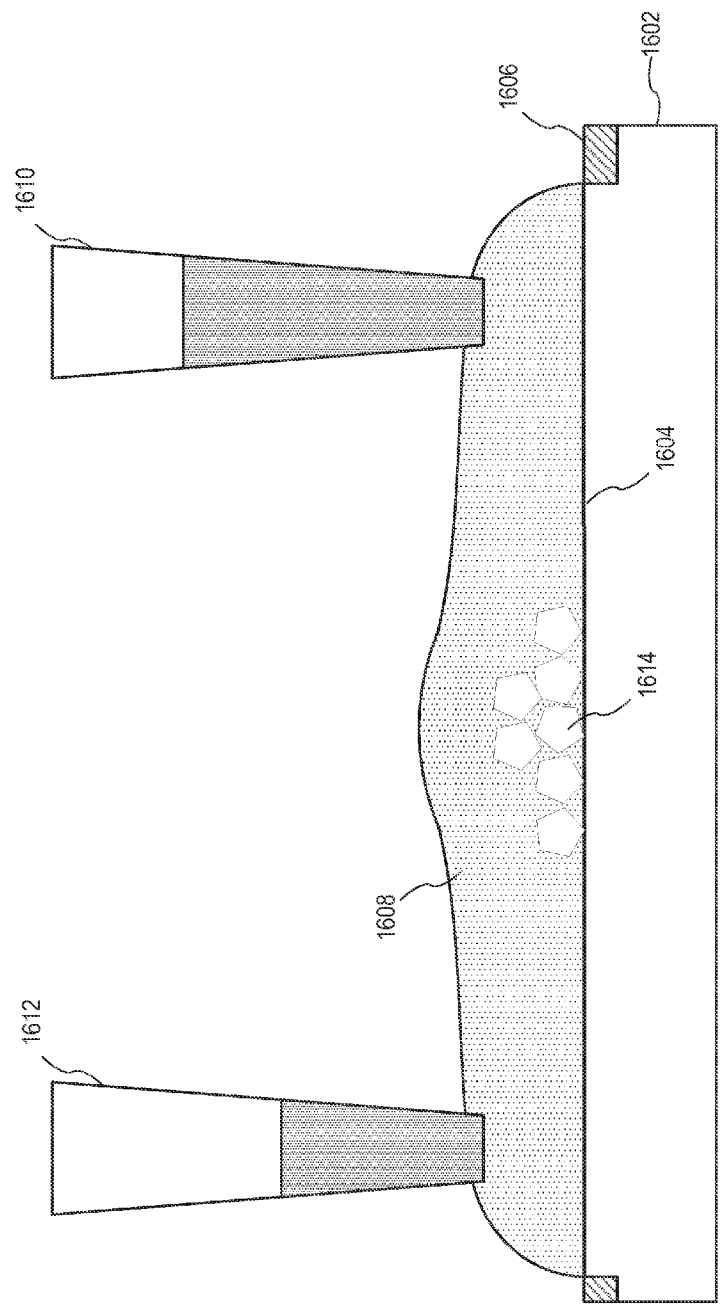
FIG. 16A is a partial cross-sectional view of an exemplary array slide in accordance with some embodiments.

FIG. 16A is a partial cross-sectional view of an exemplary array slide in accordance with some embodiments.

FIG. 16A illustrates a slide 1602 covered with a hydrophobic layer 1606 so that a portion 1604 of the slide 1602 is exposed. In FIG. 16A, a sample droplet 1608 that contains a sample solution (e.g., a solution that includes a plurality of cells 1614) is located on the exposed portion 1604 of the slide 1602. The details of the slide 1602, exposed portion 1604, and sample droplet 1608 are described above with respect to FIG. 13, and thus, are not repeated herein.

In some embodiments, as shown in FIG. 16A, multiple pipette tips (e.g., 1610 and 1612) are used. In some embodiments, a respective pipette tip is located above a respective secondary area. Multiple pipette tips can dispense the wash solution concurrently and/or remove the mixed solution concurrently, thereby enabling faster washing of cells in the sample solution than washing with a single pipette tip.

In some embodiments, a first pipette tip (e.g., 1610) is used for dispensing the wash solution and a second pipette tip (e.g., 1612) is used for removing a portion of the mixed solution while the wash solution is being dispensed from the first pipette tip, thereby enabling faster washing of cells in the sample solution than washing with a single pipette tip.

Figure 16B:
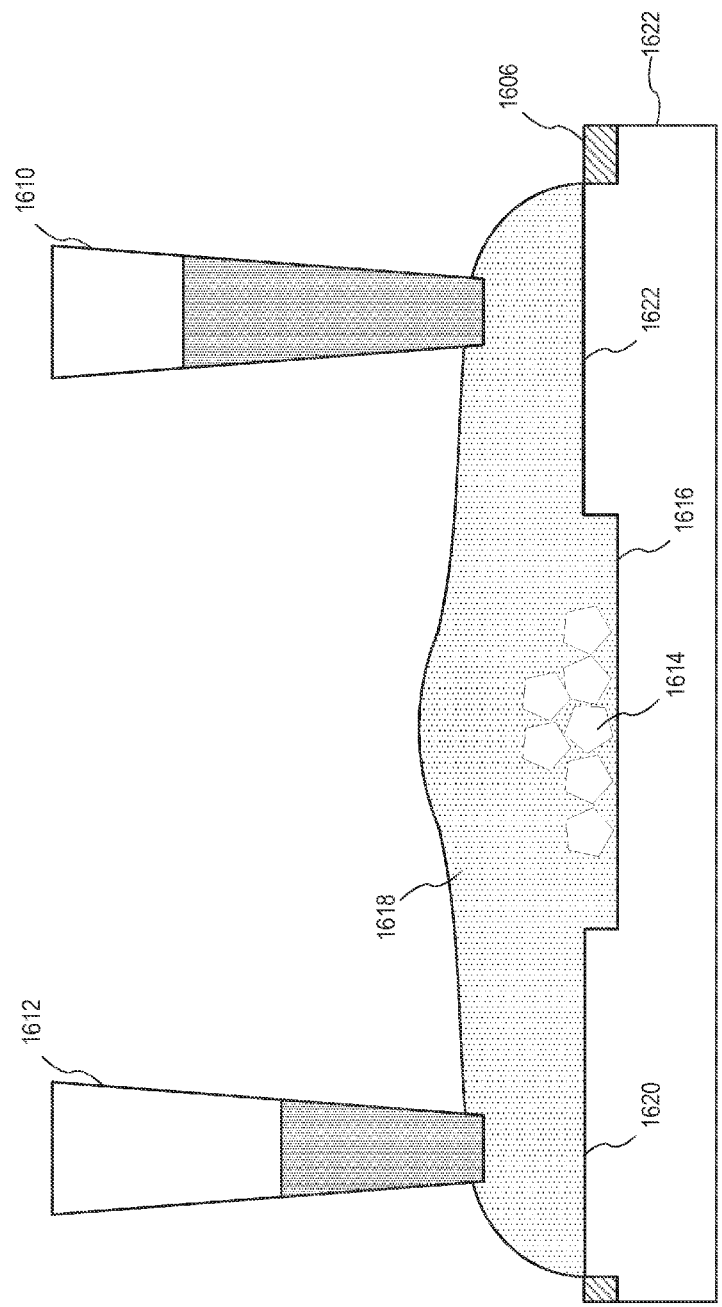
FIG. 16B is a partial cross-sectional view of an exemplary array slide in accordance with some embodiments.

FIG. 16B illustrates a slide 1622 covered with a hydrophobic layer 1606 so that a portion 1616 of the slide 1622 is exposed, which serves as a primary area. In addition, FIG. 16B shows that the slide 1622 has multiple secondary areas (e.g., 1620 and 1622) adjacent to the primary area (e.g., the exposed portion 1616). FIG. 16B shows that the primary area (e.g., the exposed portion 1616) is indented from a top surface of the secondary areas adjacent to the primary area (e.g., the exposed portion 1616). In FIG. 16B, a sample droplet 1618 that contains a sample solution (e.g., a solution that includes a plurality of cells 1614) is located at least on the exposed portion 1616 of the slide 1622. The characteristics of an indented primary area are described above with respect to FIG. 14D, and thus are not repeated herein.

Figure 17:
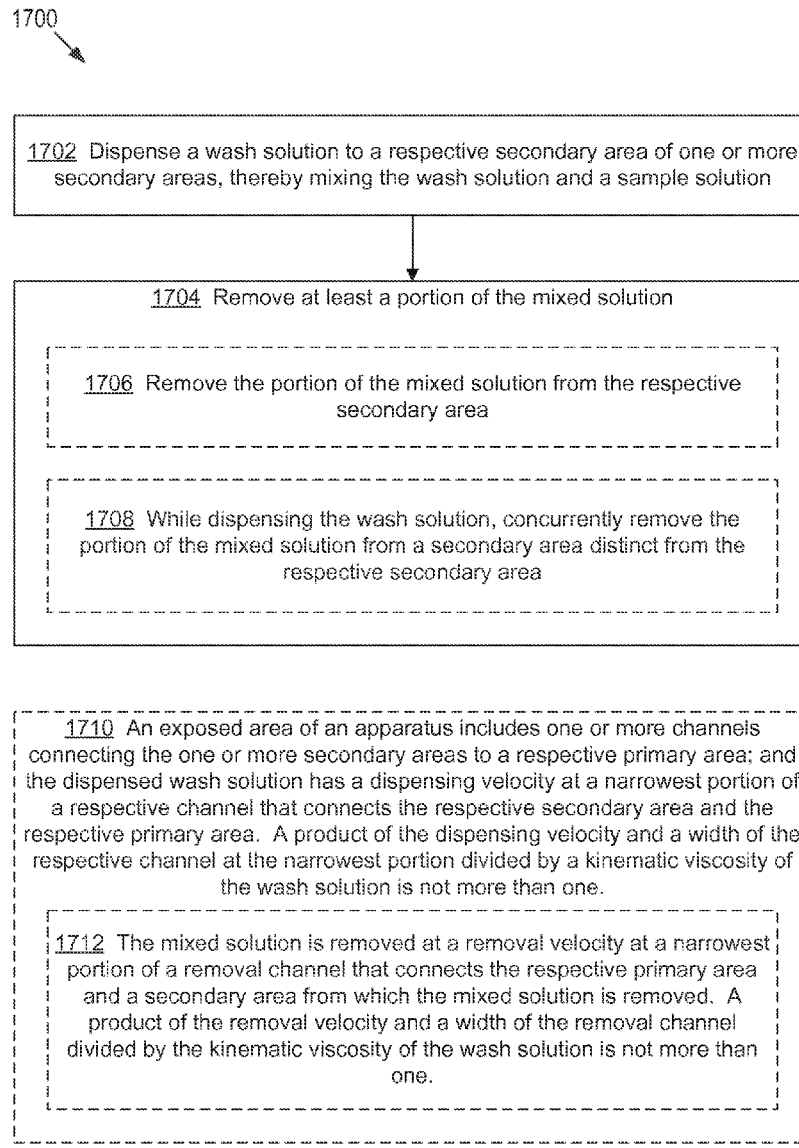
FIG. 17 is a flow chart representing a method for washing a sample in accordance with some embodiments.

FIG. 17 is a flow chart representing a method 1700 for washing sample solutions in accordance with some embodiments. In the method 1700, a respective primary area of a device is covered with a sample solution that includes a sample (e.g., cells, particles or beads conjugated with target molecules, etc.). In some embodiments, the method 1700 includes dispensing the sample solution onto the respective primary area.

The method 1700 includes (1702) dispensing a wash solution to a respective secondary area of one or more secondary areas. In some embodiments, dispensing the wash solution includes mixing the wash solution and the sample solution.

The method 1700 includes (1704) removing at least a portion of the mixed solution (e.g., a mixture of the wash solution and the sample solution).

In some embodiments, removing at least the portion of the mixed solution includes (1706) removing the portion of the mixed solution from the respective secondary area (e.g., a pipette tip is located above the secondary area and removes the mixed solution from the respective secondary area).

In some embodiments, removing at least the portion of the mixed solution includes removing the portion of the mixed solution without removing the sample in the mixed solution.

In some embodiments, removing at least the portion of the mixed solution includes removing at least a predefined portion (e.g., at least 80%, 90%, or 95%) of the mixed solution.

In some embodiments, the method 1700 includes (1708), while dispensing the wash solution, concurrently removing the portion of the mixed solution from a secondary area distinct from the respective secondary area. For example, as shown in FIG. 16A, while the first pipette tip 1610 dispenses the wash solution to the respective secondary area, the second pipette tip 1612 removes the portion of the mixed solution from another secondary area distinct from the respective secondary area.

In some embodiments, an exposed area of a device includes (1710) one or more channels connecting the one or more secondary areas to a respective primary area (e.g., channel 1508-1 in FIG. 15F, channel 1508-2 in FIG. 15G, channel 1508-3 in FIG. 15H, and channels in FIG. 15L). The dispensed wash solution has a dispensing velocity at a narrowest portion of a respective channel that connects the respective secondary area and the respective primary area. For example, in FIG. 15G, a narrowest portion of the channel 1508-2 is at a junction of the channel 1508-2 and the secondary through hole 1504-7. In FIG. 15H, a narrowest portion of the channel 1508-3 is at a junction of the channel 1508-3 and the primary through hole 1502-8. In some embodiments, a product of the dispensing velocity and a width of the respective channel at the narrowest portion divided by a kinematic viscosity of the wash solution is not more than one.

In some embodiments, the mixed solution is removed (1712) at a removal velocity at a narrowest portion of a removal channel that connects the respective primary area and a secondary area from which the mixed solution is removed. In some embodiments, the removal channel is the respective channel that connects the respective secondary area and the respective primary area. In some embodiments, the removal channel (e.g., 1508-4 in FIG. 15L) is distinct from the respective channel (e.g., 1508-5 in FIG. 15L) that connects the respective secondary area and the respective primary area. In some embodiments, a product of the removal velocity and a width of the removal channel divided by the kinematic viscosity of the wash solution is not more than one.

In some embodiments, dispensing the wash solution includes dropping one or more droplets of the wash solution onto the respective secondary area. Dropping one or more droplets of the wash solution directly onto the sample solution (e.g., a solution that includes a plurality of cells, particles, or beads) eliminates a contact between a pipette tip dispensing the wash solution and the sample solution, thereby preventing contamination of the pipette tip. However, dropping one or more droplets of the wash solution directly onto the solution that includes the plurality of cells agitates a sample in the sample solution. For example, when the sample solution includes a plurality of cells, dropping droplets of the wash solution directly on the sample solution causes at least some of the plurality of cells to float around the mixed solution. Thus, dropping one or more droplets of the wash solution directly onto the sample solution is not desirable. The array plates (or array slides) described herein address this problem by allowing one or more droplets of the wash solution to be dropped onto the respective secondary area so that the one or more droplets do not directly impact the sample solution. Instead, after the one or more droplets impinge on the respective secondary area, the one or more droplets merge with the sample solution, thereby reducing disruption to the sample.

In some embodiments, the primary area and the secondary area described above with respect to the method 1700 have characteristics of the primary area and the secondary area described above with respect to FIGS. 15A-15L (or the primary area defined by a primary through hole and a secondary area defined by a secondary through hole described above with respect to FIGS. 15A-15L). For example, the primary area and the secondary area may overlap as shown in FIG. 15C. For brevity, these details are not repeated.

A person having ordinary skill in the art would understand that the method 1700 is applicable to both array plates and array slides described herein.

In some embodiments, a method for adding a first solution to a second solution that includes a sample is performed. In this method, a respective primary area of an array plate is covered with the second solution. The method includes dropping one or more droplets of the solution to a respective secondary area, thereby mixing the first solution and the second solution. As explained above with respect to the method 1700, this reduces a contamination of the pipette tip that dispenses the first solution without agitating the sample in the second solution.

In some embodiments, a washer system includes a device holder for holding a respective device that comprises any of the above-described devices. The wash system also includes one or more dispensers configured to dispense a wash solution to the respective device; and one or more actuators for positioning a respective dispenser above the respective secondary area of the respective device held in the device holder.

In some embodiments, one or more aspirators configured to remove at least a portion of a solution located on the respective device; and one or more actuators for positioning a respective aspirator above a secondary area, distinct from the respective secondary area, of the respective device held in the device holder.

In some embodiments, one or more droplets are located on the respective device. The washer system includes one or more sensors to locate a meniscus of a respective droplet on the respective device. The one or more actuators are configured to position the respective dispenser so that at least a tip of the respective dispenser is located within the respective droplet while dispensing at least a portion of the wash solution.

In some embodiments, the respective dispenser is positioned above the respective secondary area and the respective aspirator is positioned above the secondary area distinct from the respective secondary area.

In some embodiments, a washer system includes a holder module configured to retain a device with primary areas and secondary areas, wherein a respective secondary area is located adjacent to a respective primary area. Respective sample solutions are positioned at least on respective primary areas. The device also includes a dispenser module configured to dispense a wash solution using a first set of a plurality of pipette tips. In some embodiments, the dispenser module is configured to concurrently dispense the wash solution using the first set of a plurality of pipette tips. The dispenser module is also configured to position the first set of a plurality of pipette tips above respective secondary areas while dispensing the wash solution using the first set of a plurality of pipette tips. In some embodiments, the dispenser module is not configured to position any of the first set of a plurality of pipette tips above any of the primary areas while dispensing the wash solution using the first set of a plurality of pipette tips. This configuration enables dispensing the wash solution onto two or more secondary areas without dispensing the wash solution directly onto any of the primary areas.

In some embodiments, the washer system further includes a removal module configured to remove mixed solutions using a second set of a plurality of pipette tips. A respective mixed solution includes a mixture of a respective sample solution and the wash solution. In some embodiments, the removal module is configured to concurrently remove the mixed solutions using the second set of a plurality of pipette tips. The removal module is also configured to position the second set of a plurality of pipette tips above particular secondary areas while removing the mixed solutions using the second set of a plurality of pipette tips. In some embodiments, the removal module is not configured to position any of the second set of a plurality of pipette tips above any of the primary areas while removing the mixed solutions using the second set of a plurality of pipette tips. This configuration enables removing the mixed solutions from two or more secondary areas without removing the mixed solutions directly from any of the primary areas.

As used herein, a pipette tip is deemed to be positioned above a particular area (e.g., a primary area or a secondary area) when the pipette tip is positioned directly above the particular area. For example, a vertical projection of the pipette tip onto the device is included in the particular area. That the pipette tip is located at a height above the particular area is not sufficient. For example, in FIG. 13, the pipette tip 1310 is positioned above the hydrophobic layer 1306, but the pipette tip 1310 is not positioned above the exposed portion 1304.

In some embodiments, the dispenser module and the removal module are integrated. In some other embodiments, the dispenser module and the removal module are separate modules. In some embodiments, the dispenser module includes a plurality of dispensers. In some embodiments, the removal module includes a plurality of aspirators. In some embodiments, the dispenser module is coupled with a reservoir that includes the wash solution. In some embodiments, the removal module is coupled with a waste reservoir that is configured to receive at least some of the mixed solutions.

In some embodiments it is desirable to accurately control a volume of a solution (e.g., a wash solution, a mixed solution, etc.) remaining on the array plate after aspirating the solution. A distance between an array plate and an aspiration channel is critical in controlling the volume of the remaining on the array plate after aspirating the solution. In some embodiments, the washer system includes spring-loaded pins, a respective pin including an aspiration channel at a fixed distance from a tip of the respective pin. This facilitates positioning the aspiration channel at the fixed distance from the surface of the array plate. In operation, in some embodiments, a plurality of spring-loaded pins is positioned to contact the surface of secondary wells of an array plate. After the plurality of spring-loaded pins is positioned to contact the surface of secondary wells of the array plate, a solution may be aspirated through aspiration channels located at the fixed distance from the tip of the spring-loaded pins. This facilitates that the solution is aspirated from the fixed height from the surface of secondary wells. In some embodiments, a second solution (e.g., a second wash solution) is dispensed from one or more spring-loaded pins while the one or more spring-loaded pins are positioned to contact the surface of secondary wells of an array plate. This facilitates that the second solution is dispensed from the fixed height from the surface of secondary wells.

Figure 19:
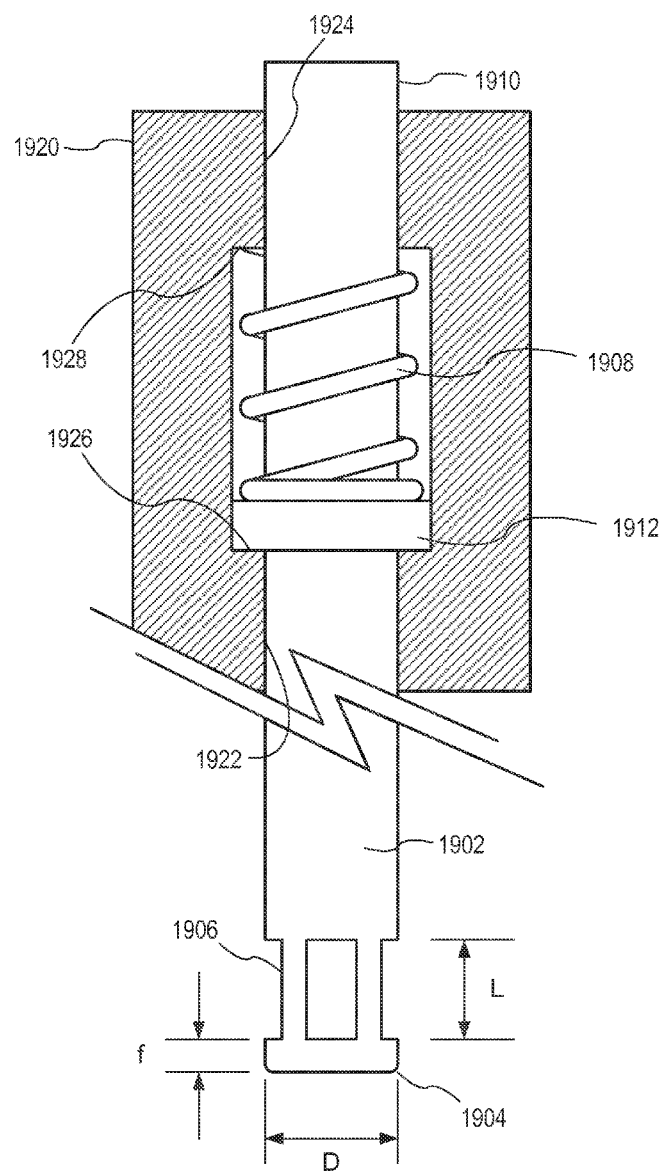
FIG. 19 illustrates a spring-loaded pin in a pin holder in accordance with some embodiments.

FIG. 19 illustrates a spring-loaded pin 1902 in a pin holder 1920 in accordance with some embodiments. In some embodiments, the pin 1902 has a tubular shape defined by a diameter D. In some embodiments, the diameter D is 100 µm or more. In some embodiments, the diameter D is 5 mm or less. In some embodiments, the diameter D is between 500 µm and 1 mm. In some embodiments, the diameter D is 750 µm. In some embodiments, the diameter D is an outer diameter of the pin 1902. In some embodiments, the diameter D is an inner diameter of the pin 1902.

As shown in FIG. 19, the pin 1902 has one or more channels 1906 at a fixed distance f from a tip 1904 of the pin 1902. In some embodiments, the fixed distance f is 10 µm or more. In some embodiments, the fixed distance f is 1 mm or less. In some embodiments, the fixed distance f is between 50 µm and 200 µm. In some embodiments, the fixed distance f is 100 µm. In some embodiments, the pin 1902 has four channels 1906 along the circumference of the pin 1902. Alternatively, the pin 1902 may have any other number of channels 1906 (e.g., one, two, three, five, six, etc.).

In some embodiments, the channel 1906 defines a rectangular hole as shown in FIG. 19. Alternatively, the channel 1906 may define a hole of any other shape (e.g., a circle, ellipse, oval, slit, etc.). In some embodiments, the channel 1906 is defined by a characteristic length L. In some embodiments, the characteristic length L is a height of the channel 1906. In some embodiments, the characteristic length L is 10 µm or more. In some embodiments, the characteristic length L is 3 mm or less. In some embodiments, the characteristic length L is between 100 µm and 1 mm. In some embodiments, the characteristic length L is between 200 µm and 300 µm. In some embodiments, the characteristic length L is determined in accordance with the speed of a solution aspirated or dispensed through the channel 1906 so that turbulence is not generated during the aspiration or dispensing of the solution. A person having ordinary skill in the art would understand that the channel 1906 may be used for aspiration of solutions, dispensing solutions, or both.

In some embodiments, an end 1910 of the pin 1902, located on the opposite end from the tip 1904, is coupled with the dispenser module. For example, a solution from the dispenser module is provided to the end 1910 of the pin 1902 and dispensed through one or more channels 1906. In some embodiments, the dispenser module includes the pin 1902. In some embodiments, the end 1910 is coupled with the removal module. For example, a solution surrounding the tip 1904 is aspirated through one or more channels 1906 and removed through the end 1910 of the pin 1902 to the removal module. In some embodiments, the pin 1902 is integrated with the removal module.

In some embodiments, the pin 1902 includes an indentation 1912. In some embodiments, the indentation 1912 of the pin 1902 is used to apply a spring force from a spring 1908 onto the pin 1902. In some embodiments, the indentation 1912 is used to limit a movement of the pin 1902 in conjunction with a stop 1926.

FIG. 19 also illustrates a cross-sectional view of a pin holder 1920 in accordance with some embodiments. In some embodiments, the pin 1902 is at least partially enclosed in a pin holder 1920 as shown in FIG. 19 (e.g., at least the tip 1904 is located outside the pin holder 1920). In some embodiments, the pin holder 1920 includes a stop 1926. The stop 1926 is used to limit a movement of the indentation 1912, which in turn limits the movement of the pin 1902. In some embodiments, the pin holder 1920 includes a spring support 1928. The spring support 1928 is used to support spring 1908. When the indentation 1912 moves up, the spring 1908 is compressed between the spring support 1928 and the indentation 1912. In some embodiments, the pin holder 1920 includes one or more pin supports 1922 and 1924. The one or more pin supports 1922 and 1924 support the pin 1902. For example, when the tip 1904 of the pin 1902 is pressed against a surface (e.g., a surface of an array plate), the one or more pin supports 1922 and 1924 provide lateral forces to maintain the pin 1902 in a vertical orientation while the pin 1902 moves vertically. When the tip 1904 of the pin 1902 is no longer in contact with the surface (e.g., either by moving up the pin holder 1920 and the pin 1902 coupled with the pin holder 1920 or by moving down the surface), the spring force applied by the spring 1908 pushes the indentation 1912 of the pin 1902 downward until the indentation 1912 contacts the stop 1926.

In some embodiments, the washer system is configured to tilt an array plate. In some embodiments, the washer system is configured to tilt the array plate (e.g., up to 60 degree) for draining oil on the array plate. Upon tilting, the oil is collected at one side of the array plate. The washer system aspirates the collected oil from the one side of the array plate, where the oil is collected. In some embodiments, after aspirating the collected oil, the washer system maintains the array plate for a predefined period of time. In some embodiments, the oil is volatile. During the predefined period of time, at least a portion of the remaining oil on the array plate evaporates. In some embodiments, either after aspirating the collected oil or after maintaining the array plate for the predefined period of time, the washer system dispenses oil to the array plate.

Various aspects and characteristics of the methods of using the array plates described above are applicable to array slides (e.g., adding one or more solutions to one or more liquid droplets of the respective liquid droplets, performing an immunoassay, and washing a respective liquid droplets), and vice versa. Because these aspects and characteristics are described above, they are not repeated herein for brevity.

It is well known to a person having ordinary skill in the art that array slides and plates can be used in many other biological and chemical reactions. Therefore, such details and specific examples are omitted for brevity.

The foregoing description, for purpose of explanation, has been described with reference to specific embodiments. However, the illustrative discussions above are not intended to be exhaustive or to limit the embodiments to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method comprising:
providing a device that includes a plurality of primary areas and a plurality of secondary areas, wherein:
one or more secondary areas of the plurality of secondary areas are distinct and separate from a respective primary area and adjacent to the respective primary area;
the plurality of primary areas and the plurality of secondary areas are hydrophilic areas surrounded collectively by hydrophobic areas; and
the respective primary area is covered with a first solution; and
dispensing a second solution, distinct from the first solution, to a respective secondary area of the one or more secondary areas adjacent to the respective primary area, thereby causing the second solution on the respective secondary area to merge with the first solution on the respective primary area and form a mixed solution that includes the first solution and the second solution, wherein:
the respective primary area is connected to the respective secondary area with a first channel;
dispensing the second solution to the respective secondary area includes causing the second solution to flow from the respective secondary area toward the respective primary area via the first channel; and
the second solution has a first velocity at a narrowest portion of the first channel, a product of the first velocity and a width of the first channel at the narrowest portion divided by a kinematic viscosity of the second solution being not more than one.

2. The method of claim 1, including:
removing at least a portion of the mixed solution.

3. The method of claim 1, wherein dispensing the second solution includes dropping one or more droplets of the second solution to the respective secondary area.

4. The method of claim 1, including:
repeating dispensing the second solution to the respective secondary area and removing at least a portion of the mixed solution.

5. The method of claim 1, wherein the first solution is a sample solution that includes a sample and the second solution is a wash solution.

6. The method of claim 1, including:
removing at least a portion of the mixed solution from the respective secondary area.

7. The method of claim 1, wherein:
the device includes an additional secondary area, distinct from the respective secondary area, of the one or more secondary areas adjacent to the respective primary area;
prior to dispensing the second solution, the additional secondary area is covered with the first solution;
dispensing the second solution causes the additional secondary area to be covered with the mixed solution; and
the method further includes, while dispensing the second solution, concurrently removing at least a portion of the mixed solution from the additional secondary area.

8. The method of claim 1, wherein:
the device includes an additional secondary area, distinct from the respective secondary area, of the one or more secondary areas adjacent to the respective primary area;
the respective primary area is connected to the additional secondary area with a second channel that is distinct from the first channel;
dispensing the second solution causes the additional secondary area to be covered with the mixed solution;
the method further includes removing the mixed solution from the additional secondary area so that the mixed solution has a second velocity at a narrowest portion of the second channel, a product of the second velocity and a width of the second channel divided by the kinematic viscosity of the mixed solution being not more than one.

9. The method of claim 1, further including:
removing the mixed solution from the respective secondary area, wherein the mixed solution has a third velocity at the narrowest portion of the first channel, a product of the third velocity and the width of the first channel at the narrowest portion divided by a kinematic viscosity of the mixed solution being not more than one.

10. The method of claim 1, wherein the respective primary area is indented from an adjacent hydrophobic area.

11. The method of claim 10, wherein the respective primary area is indented from the adjacent hydrophobic area by a first distance and the respective secondary area is indented from the adjacent hydrophobic area by a second distance that is distinct from the first distance.

12. The method of claim 10, wherein the respective secondary area is not indented from the adjacent hydrophobic area.

13. The method of claim 1, wherein dispensing the second solution includes:
   placing a pipette tip containing the second solution in proximity to the first solution so that a droplet of the second solution dispensed from the pipette tip contacts the first solution; and
   dispensing the second solution from the pipette tip, thereby causing the droplet of the second solution dispensed from the pipette tip to contact the first solution and causing the first solution and the second solution to mix.

14. The method of claim 1, wherein the respective primary area and the respective secondary area have distinct sizes.

\* \* \* \* \*